(12) United States Patent
Margolin et al.

(10) Patent No.: US 9,687,420 B2
(45) Date of Patent: *Jun. 27, 2017

(54) METHODS, COMPOSITIONS, AND DEVICES FOR SUPPLYING DIETARY FATTY ACID NEEDS

(71) Applicant: Alcresta Therapeutics, Inc., Newton, MA (US)

(72) Inventors: Alexey L. Margolin, Newton, MA (US); Robert Gallotto, Newton, MA (US); Bhami Shenoy, South Grafton, MA (US)

(73) Assignee: Alcresta Therapeutics, Inc., Newton, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/240,596

(22) Filed: Aug. 18, 2016

(65) Prior Publication Data

US 2017/0027822 A1    Feb. 2, 2017

Related U.S. Application Data

(63) Continuation of application No. 14/378,856, filed as application No. PCT/US2013/026063 on Feb. 14, 2013.

(Continued)

(51) Int. Cl.
    *A61K 9/00*     (2006.01)
    *A61J 15/00*    (2006.01)
    (Continued)

(52) U.S. Cl.
    CPC .......... *A61J 15/0092* (2013.01); *A23D 7/011* (2013.01); *A23D 7/013* (2013.01); *A23D 9/013* (2013.01);
    (Continued)

(58) Field of Classification Search
    CPC .... A61K 9/0029; A61K 38/465; A23D 7/013; B65D 1/02
    See application file for complete search history.

(56) References Cited

U.S. PATENT DOCUMENTS

4,629,742 A   12/1986  Brady et al.
4,944,944 A    7/1990  Tang et al.
(Continued)

FOREIGN PATENT DOCUMENTS

CN   101573048 A   11/2004
CN   101068565 A   11/2007
(Continued)

OTHER PUBLICATIONS

Abbott Laboratories (2009) "ProSure® Therapeutic Nutrition for People with Cancer" Product Monograph (48 pages).

(Continued)

*Primary Examiner* — Nathan Bowers
(74) *Attorney, Agent, or Firm* — Bookoff McAndrews, PLLC

(57) ABSTRACT

Nutritional formulas comprising long-chain polyunsaturated fatty acids (LC-PUFAs) are provided, along with methods and devices for preparing and/or administering nutritional formulas. In some embodiments, a percentage of the LC-PUFAs in the nutritional formula are in the form of monoglycerides and/or free fatty acids. In some embodiments, the nutritional formulas do not comprise added lipase. Also provided are methods for providing nutrition to a subject, methods for improving fat absorption, methods for improving cognitive ability, methods for preventing chronic lung disease, and methods for reducing the length of time a patient requires total parenteral nutrition.

24 Claims, 41 Drawing Sheets

Related U.S. Application Data

(60) Provisional application No. 61/600,207, filed on Feb. 17, 2012, provisional application No. 61/719,173, filed on Oct. 26, 2012.

(51) Int. Cl.

| | | |
|---|---|---|
| A23D 7/01 | (2006.01) | |
| A23D 9/013 | (2006.01) | |
| A61K 31/202 | (2006.01) | |
| A61K 38/46 | (2006.01) | |
| B65D 1/02 | (2006.01) | |
| B65D 41/02 | (2006.01) | |
| B65D 81/32 | (2006.01) | |
| B65D 85/72 | (2006.01) | |
| A23K 20/158 | (2016.01) | |
| A23L 29/00 | (2016.01) | |
| A23L 33/00 | (2016.01) | |
| A23L 33/115 | (2016.01) | |
| A23L 33/12 | (2016.01) | |
| A23K 50/30 | (2016.01) | |

(52) U.S. Cl.
CPC ............ *A23K 20/158* (2016.05); *A23K 50/30* (2016.05); *A23L 29/06* (2016.08); *A23L 33/115* (2016.08); *A23L 33/12* (2016.08); *A23L 33/40* (2016.08); *A61J 15/0003* (2013.01); *A61J 15/0026* (2013.01); *A61K 9/0029* (2013.01); *A61K 31/202* (2013.01); *A61K 38/465* (2013.01); *B65D 1/02* (2013.01); *B65D 41/02* (2013.01); *B65D 81/32* (2013.01); *B65D 85/72* (2013.01); *C12Y 301/00* (2013.01); *A23V 2002/00* (2013.01); *C12Y 301/01* (2013.01)

(56) References Cited

U.S. PATENT DOCUMENTS

| | | |
|---|---|---|
| 5,902,617 A | 5/1999 | Pabst |
| 6,346,216 B1 | 2/2002 | Kent |
| 6,541,606 B2 | 4/2003 | Margolin et al. |
| 6,635,222 B2 | 10/2003 | Kent |
| 6,749,851 B2 | 6/2004 | Mann et al. |
| 8,361,763 B2 | 1/2013 | Dayton et al. |
| 8,404,470 B2 | 3/2013 | Thum et al. |
| 8,754,126 B2 | 6/2014 | Lai et al. |
| 8,877,812 B2 | 11/2014 | Lai et al. |
| 2005/0129830 A1 | 6/2005 | Koike et al. |
| 2006/0121017 A1 | 6/2006 | Margolin et al. |
| 2009/0123634 A1* | 5/2009 | Klemann ............... A23L 33/30 426/607 |
| 2010/0075900 A1 | 3/2010 | Zwijsen et al. |
| 2010/0239559 A1 | 9/2010 | Freedman et al. |
| 2010/0304357 A1 | 12/2010 | Meyers et al. |
| 2011/0150944 A1 | 6/2011 | Rozen et al. |
| 2012/0172434 A1 | 7/2012 | Lai et al. |
| 2012/0279939 A1 | 11/2012 | Lee et al. |
| 2014/0249224 A1 | 9/2014 | Lai et al. |
| 2015/0140161 A1 | 5/2015 | Lai et al. |
| 2015/0246102 A1 | 9/2015 | Margolin |

FOREIGN PATENT DOCUMENTS

| | | |
|---|---|---|
| DE | 2935546 A1 | 3/1981 |
| JP | 1-231848 A | 9/1989 |
| JP | 11-502450 A | 3/1999 |
| JP | 2004-248671 A | 9/2004 |
| JP | 2005-272307 A | 10/2005 |
| JP | 2007-524674 A | 8/2007 |
| JP | 2007-526943 A | 9/2007 |
| JP | 2009/544780 A | 12/2009 |
| WO | WO 97/23190 | 7/1997 |
| WO | WO 2004/052115 A1 | 6/2004 |
| WO | WO 2005/072306 A2 | 8/2005 |
| WO | WO 2005/084129 A | 9/2005 |
| WO | WO 2006/044529 A | 4/2006 |
| WO | WO 2006/092622 A1 | 9/2006 |
| WO | WO 2008/054192 A1 | 5/2008 |
| WO | WO 2008/054208 A2 | 5/2008 |
| WO | WO 2011/092299 A | 8/2011 |

OTHER PUBLICATIONS

Anderson and Ma (2009) "Are all n-3 polyunsaturated fatty acids created equal?" *Lipids Health Dis.* 8:33, doi:10.1186/1476-511X-8-33 [online], published Aug. 10, 2009 (20 pages).

Arterburn et al. (2006) "Distribution, interconversion, and dose response of n-3 fatty acids in humans" *Am. J. Clin. Nutr.*, 83(suppl.):1467S-76S.

Balanzá-Martinez et al. (2011) "Therapeutic use of omega-3 fatty acids in bipolar disorder" *Expert Rev. Neurother.*, 11(7):1029-47.

Bansi at al. (2000) "Fibrosing colonopathy in an adult owing to over use of pancreatic enzyme supplements" *Gut*, 46(2):283-85.

Basri et al. (1994) "Immobilization of hydrophobic lipase derivatives on to organic polymer beads" *J. Chem. Tech. Biotechnol.*, 59(1):37-44.

Bengmark and Jeppsson (1995) "Gastrointestinal surface protection and mucosa reconditioning" *JPEN J. Parenter Enteral Nutr.*, 19(5):410-5.

Bhushan et al. (2008) "Immobilization of Lipase by Entrapment in Ca-alginate Beads" *J. Bioactive Compatible Polymers*, 23(6):552-62.

Birch et al. (2010) "The DIAMOND (DHA Intake and Measurement of Neural Development) Study: A double-masked, randomized controlled clinical trial of the maturation of infant visual acuity as a function of the dietary level of docosahexaenoic acid" *Am. J. Clin. Nutr.* 91(4):848-59.

Birch et al. (2010) "The impact of early nutrition on incidence of allergic manifestations and common respiratory illnesses in children" *J. Pediatr.*, 158(6):902-6.

Bolsover et al. *Cell Biology: A Short Course.* 3rd Ed., John Wiley & Sons, Inc., 2011: p. 39.

Borowitz et al. (1995) "Use of pancreatic enzyme supplements for patients with cystic fibrosis in the context of fibrosing colonopathy" *J. Pediatr.*, 127(5):681-84.

Brenna et al. (2009) "α-Linolenic acid supplementation and conversion to n-3 long-chain polyunsaturated fatty acids in humans" *Prostaglandins Leukot. Essent. Fatty Acids.* 80(2-3):85-91.

Burgess et al. (2000) "Long-chain polyunsaturated fatty acids in children with attention-deficit hyperactivity disorder" *Am. J. Clin. Nutr.*, 71(suppl.):327S-30S.

Calder (2009) "Fatty acids and immune function: relevance to inflammatory bowel diseases" *Int. Rev. Immunol.*, 28(6):506-34.

Chiou et al. (2007) "Immobilization of Lipase to Chitosan Beads using a Natural Cross-Linker" *Prep. Biochem. Biotechnol.*, 37(3):265-75.

Chung et al. (2008) "Fish oil supplementation of control and (n-3) fatty acid-deficient male rats enhances reference and working memory performance and increases brain regional docosahexaenoic acid levels" *J. Nutr.* 138(6):1165-71.

Clandinin et al. (1994) "Relationship between fatty acid accretion, membrane composition, and biologic functions" *J. Pediatr.*, 125:S25-32.

Damerla et al. (2008) "Pancreatic Enzyme Supplementation in Pancreaetic Cancer" *J. Support. Oncol.*, 6:393-6.

Davidson et al. (2004) "Weight stabilization is associated with improved survival duration and quality of life in unrespectable pancreatic cancer" *Clinical Nutrition*, 23:239-47.

Elnashar "The Art of Immobilization using Biopolymers, Biomaterials and Nanobiotechnology" Chapter 1 in *Biotechnology of Biopolymers.* Prof. Magdy Elnashar (Ed.), InTech. 2011: pp. 3-32.

Emi et al. (1994) "Lipoprotein lipase immobilization onto copoly(ethylene/acrylic acid) fiber", *Eur. Polymer J.*, 30(5):589-95.

(56) References Cited

OTHER PUBLICATIONS

Empey et al. (1991) "Fish oil-enriched diet is mucosal protective against acetic acid-induced colitis in rats" *Canadian J. Physiol. Pharma.*, 69(4):480-7.

European Patent Application No. 13749880.4, by Alcresta, Inc.: Extended European Search Report and Opinion, dated Aug. 25, 2015 (9 pages).

Fan et al. (2004) "Dietary docosahexaenoic acid suppresses T cell protein kinase C theta lipid raft recruitment and IL-2 production" *J. Immunol.*, 173:6151-60.

Fernández-Lorente et al. (2010) "Hydrolysis of Fish Oil by Lipases Immobilized Inside Porous Supports" *J. Am. Oil Chem. Soc.*, doi:10.1007/s11746-10-1728-1 [online], published Dec. 14, 2010 (8 pages).

Fernández-Lorente et al. (2011) "Release of Omega-3 Fatty Acids by the Hydrolysis of Fish Oil Catalyzed by Lipases Immobilized on Hydrophobic Supports" *J. Am. Oil Chem. Soc.*, 88:1173-78.

Forsyth et al. (1999) "A randomized controlled study of the effect of long chain polyunsaturated fatty acid supplementation on stool hardness during formula feeding" *Arch. Dis. Child*, 81:253-6.

Gadek et al. (1999) "Effect of enteral feeding with elcosapentaenoic acid, gamma-linolenic acid, and antioxidants in patients with acute respiratory distress syndrome" *Grit. Care Med.*, 27(8):1409-20.

Graham (1977) "Enzyme replacement therapy of exocrine pancreatic insufficiency in man. Relations between in vitro enzyme activities and in vivo potency in commercial pancreatic extracts" *N. Engl. J. Med.*, 296(23):1314-17.

Greenberger et al. (1966) "Absorption of Medium and Long Chain Triglycerides: Factors Influencing Their Hydrolysis and Transport" *J. Clin. Invest.*, 45(2):217-27.

Gunnlaugsdottir et al. (1998) "Alcoholysis and Glyceride Synthesis with Immobilized Lipase on Controlled-Pore Glass of Varying Hydrophobicity in Supercritical Carbon Dioxide" *Enzyme and Microbial. Tech.*, 22:360-367.

Gustafsson, H. (2012) "Enzyme Immobilization in Mesoporous Silica" Thesis for the Degree of Licentiate of Engineering, Department of Chemical and Biological Engineering, Chalmers University of Technology; Göteborg, Sweden.

Herzig et al. (2011) "Fecal pancreatic elastase-1 levels in older individuals without known gastrointestinal diseases or diabetes mellitus" *BMC Geriatrics*, 11:4, doi:10.1186/1471-2318-11-4 [online], published Jan. 25, 2011 (5 pages).

Horrocks et al. (1999) "Health benefits of docosahexaenoic acid (DHA)" *Pharmacological Res.* 40(3):211-25.

Hudert et al. (2006) "Transgenic mice rich in endogenous omega-3 fatty acids are protected from colitis" *PNAS*, 103(30):11276-11281.

Innis (2003) "Perinatal biochemistry and physiology of long-chain polyunsaturated fatty acids" *J. Pediatr.*, 143:S1-S8.

International Search Report and Written Opinion mailed May 9, 2013, in International Patent Application No. PCT/US2013/026053 (Alcresta, Inc.) (10 pages).

ISSFAL (International Society for the Study of Fatty Acids and Lipids) (Jul. 2, 2014) "Omega-3 Fats May Reduce Risk of Gastrointestinal Diseases" Press Release [online]. Retrieved from: http://www.issfal.org/news/articles/2014/07/02/omega-3-fats-may-reduce-risk-of-gastrointestional-diseases (2 pages).

Jensen et al. (1983) "Determination of lipase specificity" *Lipids*, 18(3):239-52.

Jensen at al. (1985) "Specificity of Human Milk Bile Salt-Stimulated Lipase" *J. Pediatr. Gastroentrol. Nutr.*, 4:580-2.

Jensen et al. (1986) "Absorption of individual fatty acids from long chain or medium chain triglycerides in very small infants" *Am. J. Clin. Nutr.*, 43:745-51.

Jicha and Markesbery (2010) "Omega-3 fatty acids: potential role in the management of early Alzheimer's disease" *Clin. Interv. Aging*, 5:45-61.

Kalivianakis et al. (1999) "Fat malabsorption in cystic fibrosis patients receiving enzyme replacement therapy is due to impaired intestinal uptake of long-chain fatty acids" *Am. J. Clin. Nutr.*, 69:127-34.

Koletzo et al. (2008) "The roles of long-chain polyunsaturated fatty acids in pregnancy, lactation and infancy: review of current knowledge and consensus recommendations" *J. Perinat. Med.*, 36(1):5-14.

Kris-Etherton et al. (2002) "Fish consumption, fish oil, omega-3 fatty acids, and cardiovascular disease" *Circulation*, 106:2747-57.

Lapillone et al. (2009) "Reevaluation of the DHA requirement for the premature infant" *Prostaglandins, Leukotrines and Essential Fatty Acids*, 81:143-50.

Last "Lipase and the Fat Metabolism" *Lipase—The Universal Remedy* [online], http://www.health-science-spirit.com/lipase/html, accessed Jul. 24, 2012 (8 pages).

Lauritzen et al. (2001) "The essentiality of long chain n-3 fatty acids in relation to development and function of the brain and retina" *Prog. Lipid Res.*, 40:1-94.

Lie et al. (1991) "Hydrolysis and esterification with immobilized lipase on hydrophobic and hydrophilic zeolites" *J. Chem. Tech. Biotechnol*, 50:549-53.

Logan et al. (2004) "Omega-3 fatty acids and major depression: A primer for the mental health professional" *Lipids Health Dis.*, 3:25, doi:10.1186/1476-511X-3-25 [online]: published Nov. 9, 2004 (8 pages).

Malone (2005) "Enteral Formula Selection: A Review of Selected Product Categories" *Pract. Gastr.*, 29(6):44-74 (19 pages total).

Mañe et al. (2009) "Partial Replacement of Dietary (n-6) Fatty Acids with Medium-Chain Triglycerides Decreases the Incidence of Spontaneous Colitis in Interleukin-10-Deficient Mice" *J. Nutr.*, 139:603-10.

Martek Press Release (May 4, 2010), "Study Published in Alzheimer's & Dementia: The Journal of the Alzheimer's Association Shows Algal DHA Improved Memory and Learning in Healthy Adults Age 55 and Older" [online]. Downloaded from: http://www.prweb.com/releases/MIDAS/DHA/prweb3955084.htm on Jan. 9, 2015 (2 pages).

Martin et al. (2011) "Decreased Postnatal Docosahexaenoic and Arachidonic Acid Blood Levels in Premature Infants are Associated with Neonatal Morbidities" *J. Pediatr.*, 159(5):743-49.

Martinez et al. (1992) "Tissue levels of polyunsaturated fatty acids during early human development" *J. Pediatr.*, 120:S129-S138.

McCann et al. (2005) "Is docosahexaenoic acid, an n-3 long-chain polyunsaturated fatty acid, required for development of normal brain function? An overview of evidence from cognitive and behavioral tests in humans and animals" *Am. J. Clin. Nutr.*, 82:281-95.

McDaniel et al. (2011) "Fish oil supplementation alters levels of lipid mediators of inflammation in microenvironment of acute human wounds" *Wound Repair Regen.*, 19(2):189-200.

McNamara et al. (2008) "Deficits in docosahexaenoic acid associated elevations in the metabolism of arachidonic acid and saturated fatty acids in the postmortem orbitofrontal cortex of patients with bipolar disorder" *Psychiatry Res.*, 160(3):285-99.

McNamara et al. (2010) "Docosahexaenoic acid supplementation increases prefrontal cortex activation during sustained attention in healthy boys: a placebo-controlled, dose-ranging, functional magnetic resonance imaging study" *Am. J. Nutr.*, 91:1060-67.

McNamara et al. (2010) "Selective deficits in erythrocyte docosahexaenoic acid composition in adult patients with bipolar disorder and major depressive disorder" *J. Affect. Disord.*, 126(1-2):303-11.

Milligan and Bazinet (2008) "Evolutionary modifications of human milk composition: evidence from long-chain polyunsaturated fatty acid composition of anthropoid milks" *J. Human Evol.*, 55:1086-95.

Mu (2008) "Bioavailability of omega-3 long-chain polyunsaturated fatty acids from foods" *AgroFOOD Industry Hi Tech Supplement*, 19(4):24-6.

Murty et al. (2002) "Hydrolysis of Oils by Using Immobilized Lipase Enzyme: A Review" *Biotechnol. Bioprocess Eng.*, 7:57-66.

Nestle (2011) "Gerber® Infant Formulas Nutrient Comparison Chart" (8 pages).

Nieto et al. (1999) "Synthesis of structured triacylglycerols containing medium-chain and long-chain fatty acids by interesterification with a stereospecific lipase from Mucor mieher" *Grases y Aceites*, 50(3):199-202.

(56) References Cited

OTHER PUBLICATIONS

Oh et al. (2010) "GPR120 is an omega-3 fatty acid receptor mediating potent anti-inflammatory and insulin-sensitizing effects" *Cell.* 142(5):687-98.

Oksman et al. (2006) "Impact of different saturated fatty acid, polyunsaturated fatty acid and cholesterol containing diets or beta-amyloid accumulation in APP/PS1 transgenic mice" *Neurobiol. Dis.,* 23(3):563-72.

Peretti et al. (2005) "Mechanisms of lipid malabsorption in Cystic Fibrosis: the impact of essential fatty acids deficiency" *Nutrition & Metabolism,* 2:11, doi:10.1186/1743-7075-2-11 [online]; published May 3, 2005 (18 pages).

Pérez et al. (2011) "A Novel Halophilic Lipase, LipBL, Showing High Efficiency in the Production of Elcosapentaenoic Acid (EPA)" *PLoS ONE,* 6(8):e23325, doi:10.1371/journal.pone.0023325 [online], published Aug. 10, 2011 (11 pages).

Pontes-Arruda et al. (2006) "Effects of enteral feeding with elcosapentaenoic acid, y-linolenic acid, and antioxidants in mechanically ventilated patients with severe sepsis and septic shock" *Crit. Care Med.,* 34(9):2325-33.

Reisbick et al., (1997) "Visual attention in infant monkeys: effects of dietary fatty acids and age" *Dev. Psychol.,* 33(3):387-95.

Ren et al. (2011) "Facile, high efficiency immobilization of lipase enzyme on magnetic iron oxide nanoparticles via a biomimetic coating" *BMC Biotechnol.,* 11:63, doi: 10.1186/1472-6750-11-63 [online], published Jun. 8, 2011 (8 pages).

Ruthig and Meckling-Gill (1999) "Both (n-3) and (n-6) fatty acids stimulate wound healing in the rat intestinal epithelial cell line, IEC-6" *J. Nutr.,* 129:1791-98.

Sanderson et al. (1997) "Dietary fish oil diminishes the antigen presentation activity of rat dendritic cells" *J. Leukoc. Biol.,* 62:771-7.

Sangiovanni and Chew (2005) "The role of omega-3 long-chain polyunsaturated fatty acids in health and disease of the retina" *Progr. Retinal Eye Res.,* 24:87-138.

Sarkadi-Nagy et al. (2004) "Formula feeding potentiates docosahexaenoic and arachidonic acid biosynthesis in term and preterm baboon neonates" *J. Lipid Res.,* 45:71-80.

Scheltens et al. (2012) "Efficacy of Souvenaid in Mild Alzheimer's Disease: Results from a Randomized Controlled Trial" *J. Alzheimer's Dis.,* 31:225-36.

Stark and Holmberg (1989) "Covalent immobilization of lipase in organic solvents" *Biotechnol. Bioeng.,* 34(7):942-50.

Stoll et al. (1999) "Omega 3 Fatty Acids in Bipolar Disorder. A Preliminary Double-blind, Placebo-Controlled Trial" *Arch. Gen. Psychiatry,* 56(5):407-12.

Toyo Denka Kogyo Co., Ltd. (Date unknown) "New Inorganic Carriers for Immobilization of Enzymes Toyonite" (12 pages).

Ville et al. (2002) "Physiological study of pH stability and sensitivity to pepsin of human gastric lipase" *Digestion,* 65:73-81.

Yuhas et al. (2006) "Human milk fatty acid composition from nine countries varies most in DHA" *Lipids,* 41(9):851-58.

\* cited by examiner

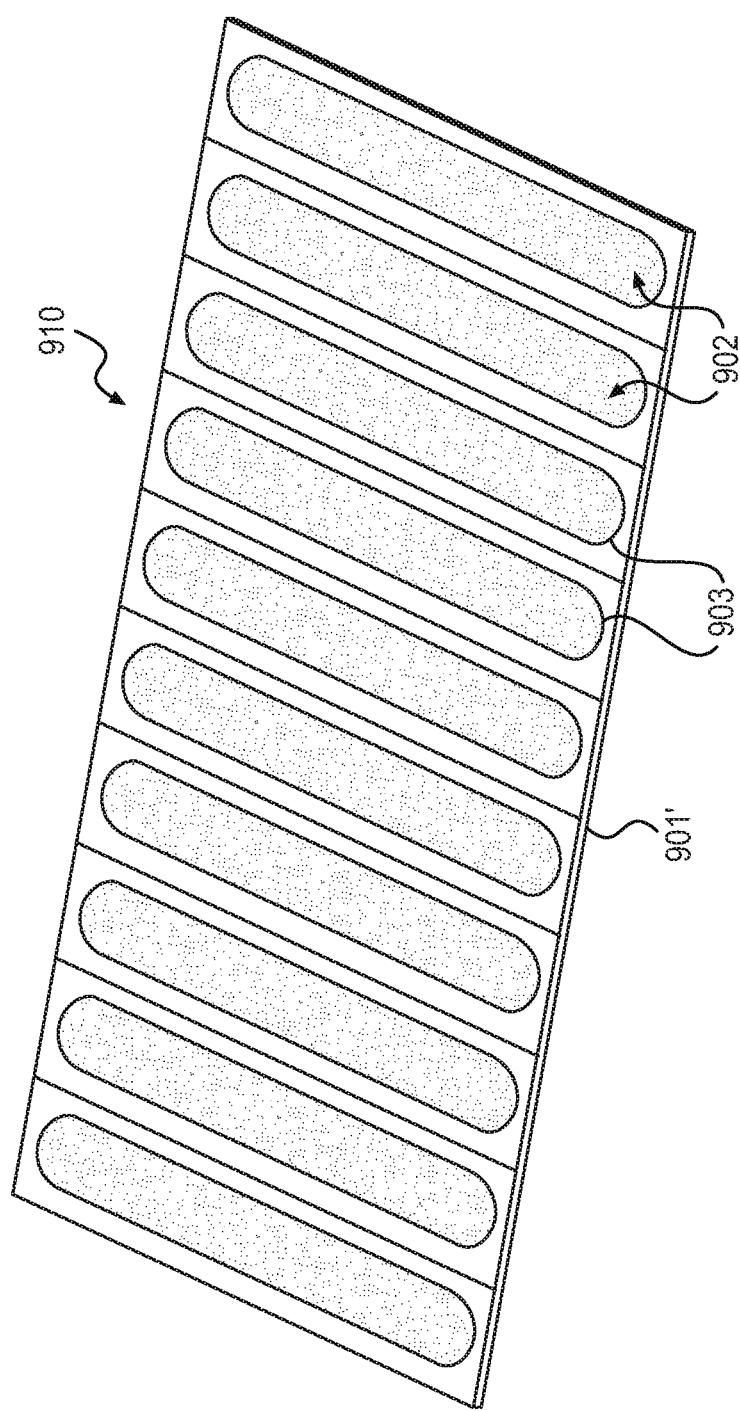

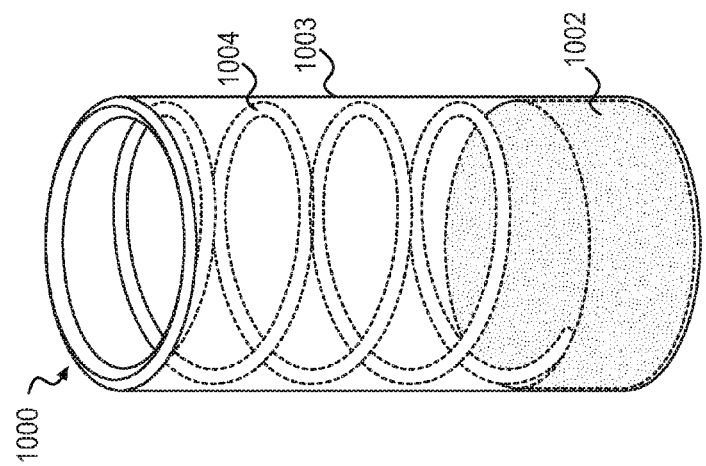
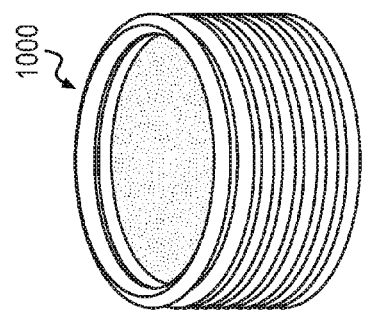
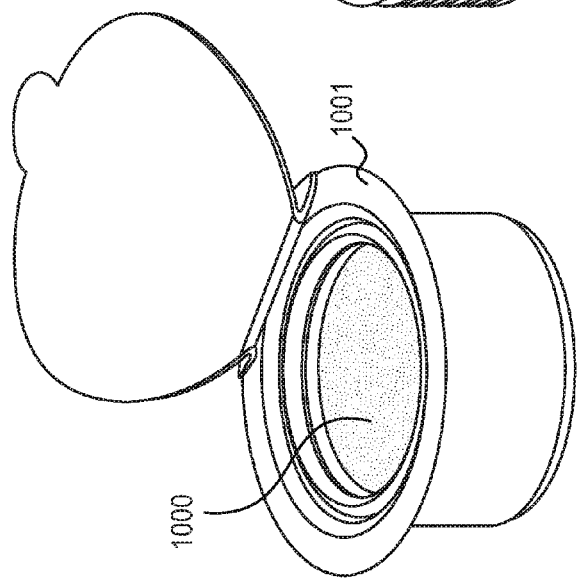
FIG. 10C
FIG. 10B
FIG. 10A

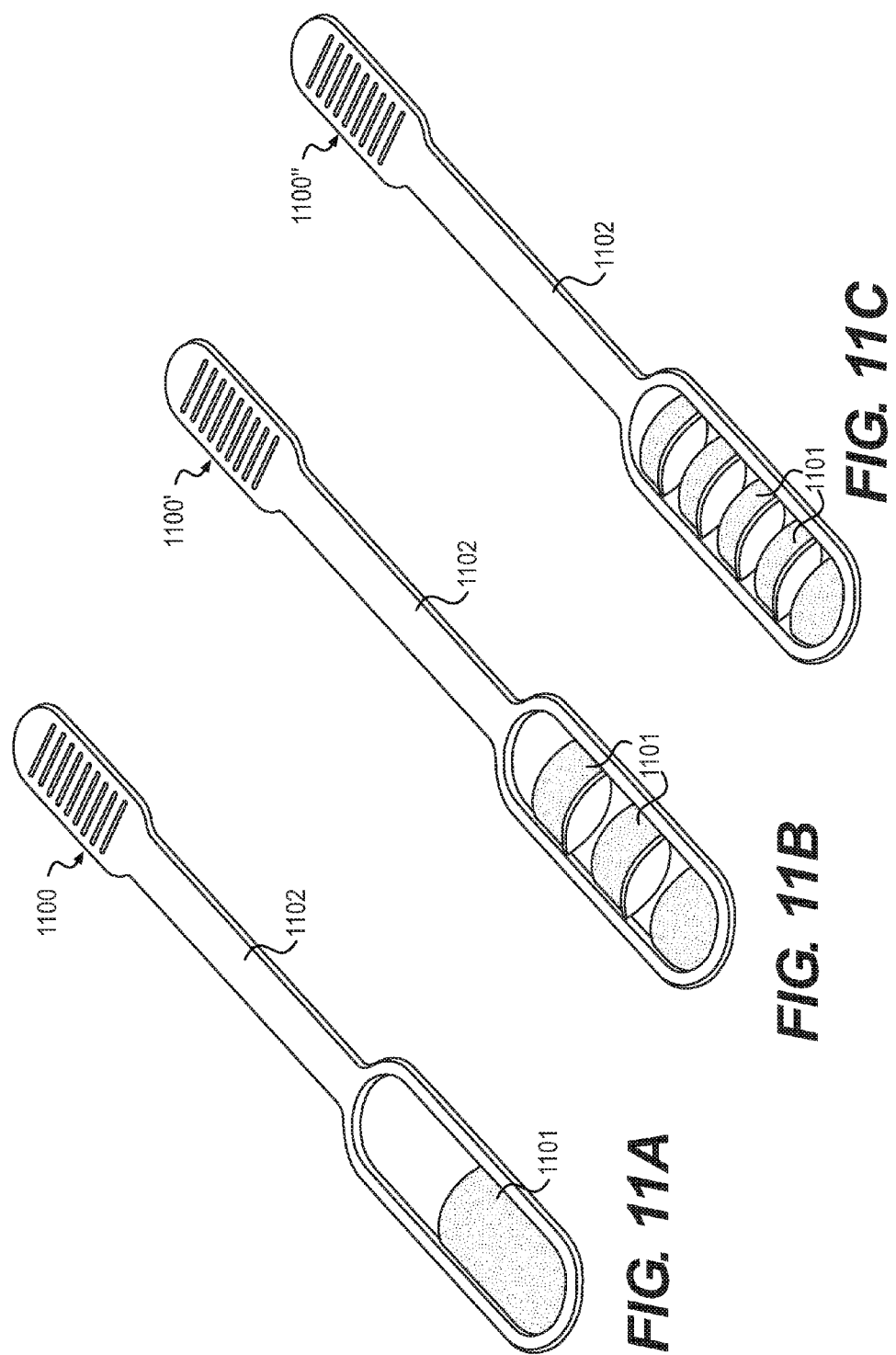

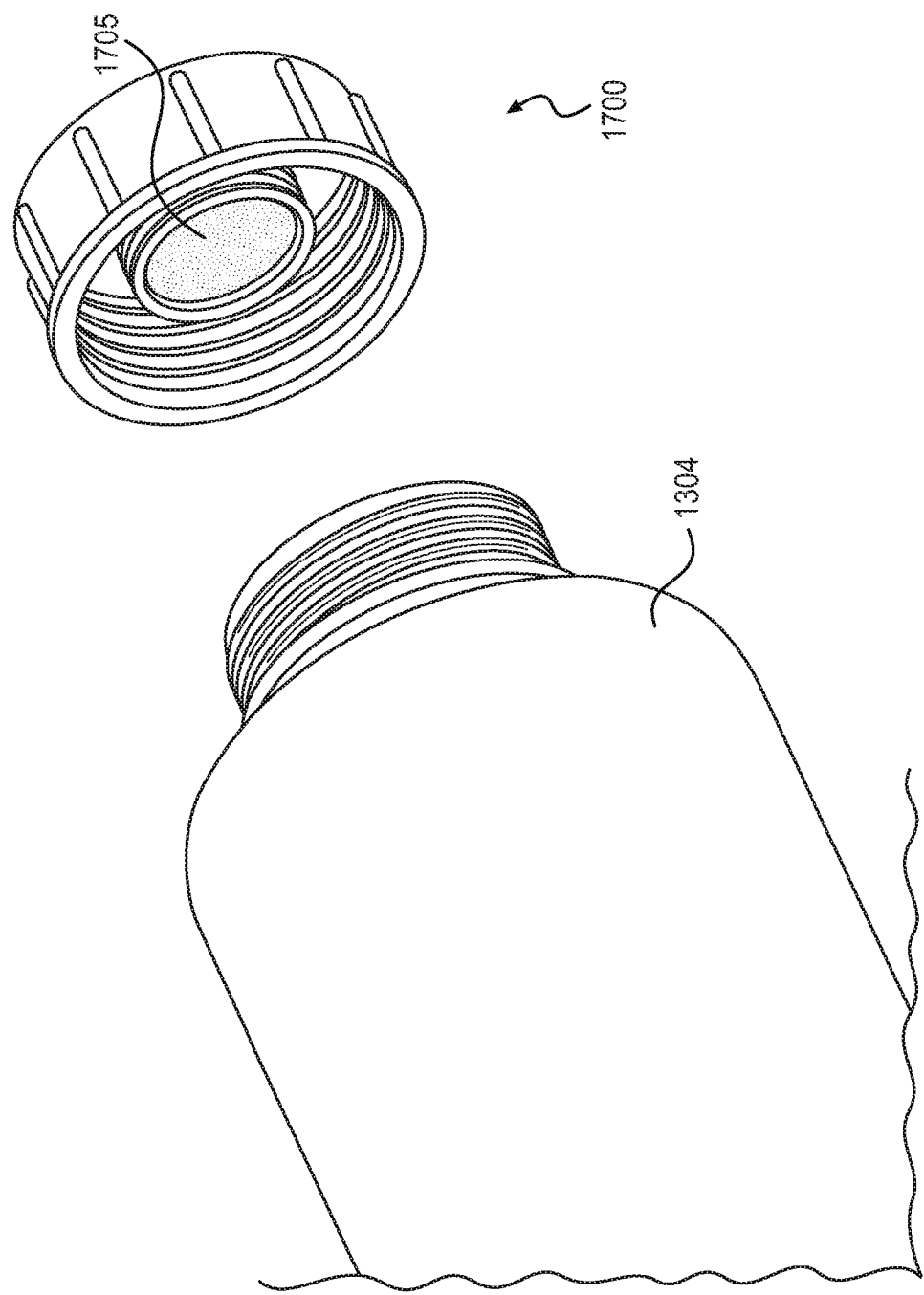

METHODS, COMPOSITIONS, AND DEVICES FOR SUPPLYING DIETARY FATTY ACID NEEDS

The application is a continuation of U.S. patent application Ser. No. 14/378,856, filed Aug. 14, 2014, which is a U.S. national phase entry under 35 U.S.C. §371 from International Application No. PCT/US2013/026063, filed Feb. 14, 2013, which claims priority under 35 U.S.C. §119 to U.S. Provisional Application No. 61/600,207, which was filed on Feb. 17, 2012 and to Provisional Application No. 61/719,173, which was filed on Oct. 26, 2012. All of these applications are incorporated herein by reference in their entireties.

Long-chain fatty acids are critical to human health and development. Long-chain fatty acids that are consumed in the diet are primarily in the form of triglycerides (TGs), in which three long-chain fatty acids are bound to a glycerol molecule via ester linkages. Absorption of long-chain triglycerides first requires the enzymatic action of lipases, (e.g. pancreatic lipase), which digest triglycerides through hydrolysis, breaking them down into monoglycerides and further into free fatty acids. Once available, these monoglycerides and free fatty acids are absorbed by endothelial cells in the small intestine, where they undergo reesterification, followed by transport to the liver and ultimately to tissues in the body for various physiological purposes. D. Kasper et al., *Harrison's Principles of Internal Medicine* 16th Ed. (2004). While medium chain triglycerides can be absorbed across the intestinal lumen, long-chain triglycerides cannot, therefore, pancreatic lipase is essential for proper long-chain fatty acid hydrolysis and absorption. C. Jensen et al., Am. J. Clin. Nutr. 43:745-751 (1986). However, some people are unable to adequately breakdown long-chain triglycerides, e.g., patients suffering from compromised pancreatic output, malabsorption or pancreatic insufficiency, and as a result, may suffer from absorption of fatty acids that is inadequate to maintain health.

Commercially available lipase supplements may be added to the diet to improve hydrolysis of long-chain triglycerides. However, for a number of reasons, lipase supplements will not necessarily solve the problem of poor fatty acid absorption in all people suffering from reduced ability to break down long chain triglycerides or otherwise in need of receiving elemental fatty acids. For example, most commercial lipase supplements are made from animal pancreatic lipase, which is known to have significantly reduced stability below pH 7. See, e.g., US2010/0239559; D. Kasper et al., *Harrison's Principles of Internal Medicine* 16th Ed. (2004). By the time such lipases pass through the stomach, significant amounts are likely to have been inactivated. Further, not all lipases work to the same degree for hydrolysis of a given long-chain fatty acid, indicating lipase specificity is an important consideration. R. Jensen et al., *Lipids* 18(3):239-252 (1983). And in some populations with pancreatic insufficiency, nutritional formulas are tightly regulated, such as in pre-term infants or in patients in intensive care units. For these controlled populations, it may not be desirable or feasible to supplement already-approved formulas with additional ingredients. Moreover, although many fatty acid supplemented formulas may contain medium-chain triglycerides, there is a distinct medical benefit to dietary intake of long-chain fatty acids. Thus, there is a need for improved methods of enhancing hydrolysis of long-chain triglycerides.

Proper hydrolysis of long-chain polyunsaturated triglycerides (TG-LCPUFA) is particularly important for several reasons. Long-chain polyunsaturated fatty acids (LC-PUFAs) are critical for neural and retinal development. Moreover, some are considered "essential fatty acids," meaning that humans cannot synthesize them and must obtain them from dietary sources. The principal dietary source for n-3 LC-PUFAs docosahexaenoic acid (DHA) and eicosapentaenoic acid (EPA) is their precursor, alpha-linolenic acid (ALA), which is an essential fatty acid. Endogenous enzymes, however, are highly inefficient at converting ALA to DHA and EPA. According to an official statement by the International Society for the Study of Fatty Acids and Lipids (ISSFAL), the conversion of ALA to DHA is about 1% in infants and considerably lower in adults. Brenna et al., *Prostaglandins Leukot Essent Fatty Acids,* 80(2-3):85-91 (2009). Thus, although DHA and EPA are not essential fatty acids per se, dietary sources of DHA and EPA are important. The principal dietary source for the n-6 LC-PUFA arachidonic acid (ARA or AA) is linoleic acid (LA), which is an essential fatty acid.

Embodiments of the invention solve these various problems by (i) providing lipases that are surprisingly more efficient than others at hydrolyzing certain long-chain triglycerides and esters, such as, e.g., long-chain polyunsaturated triglycerides and esters (ii) providing a nutritional formula, such as, e.g., a medical nutritional formula or an infant formula, comprising pre-hydrolyzed components (i.e., monoglycerides and/or free fatty acids) of LC-PUFA triglycerides, LC-PUFA fatty acid esters, and/or other long-chain triglycerides or long-chain fatty acid esters, (iii) providing methods of producing such nutritional formula, including methods in which a formula containing LC-PUFA triglycerides, LC-PUFA fatty acid esters, and/or other long-chain triglycerides or long-chain fatty acid esters is temporarily exposed to lipase and (iv) providing devices designed to provide nutritional formulas comprising monoglycerides and/or free fatty acids, e.g., LC-PUFA triglycerides and/or LC-PUFA fatty acid esters. In embodiments in which the formula is temporarily exposed to the lipase and the lipase is removed or separated from the formula prior to ingestion, the invention provides the advantage of ensuring breakdown of LC-PUFA triglycerides, LC-PUFA fatty acid esters, and/or other long-chain triglycerides or long-chain fatty acid esters without requiring ingestion of exogenous lipase.

Accordingly, some embodiments of the invention provide a nutritional formula. In some embodiments, the nutritional formula comprises LC-PUFAs. In some embodiments, more than 2% of the total LC-PUFAs are in the form of monoglycerides and free fatty acids, i.e. less than 98% of the total LC-PUFAs are in triglyceride or ester form. In some embodiments, the LC-PUFA monoglycerides and free fatty acids comprise more than 2.5%, more than 3%, more than 4%, more than 5%, more than 6%, more than 7%, more than 8%, more than 10%, more than 12%, more than 15%, more than 20%, more than 25%, more than 30%, more than 40%, more than 50%, or more than 75% of the total LC-PUFAs in a nutritional formula. In certain embodiments, the ratio of LC-PUFA monoglycerides and free fatty acids to triglycerides and esters is at least 0.08:1, at least 0.09:1, at least 0.1:1, at least 0.25:1, at least 0.5:1, at least 1:1, at least 2:1, at least 3:1, at least 4:1, at least 5:1, at least 8:1, at least 10:1, or at least 20:1.

In certain embodiments, the nutritional formula is formulated for administration to premature infants. Other nutritional formulas encompassed by the invention are formulated for infants, toddlers, children, or adults who have a reduced ability to hydrolyze LC-PUFA triglycerides, LC-PUFA fatty acid esters, and/or other long-chain triglycerides or long-chain fatty acid esters, or who simply need additional elemental dietary LC-PUFAs and/or other long-chain fatty acids. In some embodiments, a nutritional formula of the invention is for a subject who is less than 1 year old. In some embodiments, the subject is between 1 and 4 years old. In some embodiments, the subject is between 1 and 6 years old.

In certain embodiments, the nutritional formula of the invention is a medical nutritional formula, i.e., a formula that is formulated to be consumed or administered orally or enterally under medical supervision, such as those distributed through hospitals or pharmacies under a prescription. Typically, a medical nutritional formula is formulated for dietary management of a specific medical disorder, disease, or abnormal condition, for which there are distinctive nutritional requirements. A medical nutritional formula must have "Generally Recognized As Safe" status and comply with FDA regulations that pertain to labeling, product claims, and manufacturing.

In some embodiments, the nutritional formula does not contain added lipase. In other embodiments, the nutritional formula contains a lipase. In some embodiments, the lipase is selected from *Chromobacterium viscosum, Pseudomonas fluorescens, Burcholderia cepacia*, and *Rhizopus oryzae* lipases.

In some embodiments, the nutritional formula comprises EPA, DHA, ARA, LA, and/or ALA.

Because free polyunsaturated fatty acids are unstable and rapidly degrade, the invention also provides convenient and effective methods of preparing the nutritional formulas of the invention shortly before ingestion by a subject. In certain embodiments, the method comprises exposing a liquid nutritional composition comprising LC-PUFA triglycerides, LC-PUFA fatty acid esters, and/or other long-chain triglycerides and/or esters of long-chain fatty acids to a lipase prior to ingestion by a person in need of additional dietary LC-PUFAs and/or other long-chain fatty acids. In some embodiments, the liquid nutritional composition is exposed to lipase for at least one minute, at least 2 minutes, at least 3 minutes, at least 5 minutes, at least 8 minutes, at least 10 minutes, at least 15 minutes, at least 30 minutes, at least 45 minutes, or at least 60 minutes prior to ingestion. In some embodiments, the liquid nutritional composition is exposed to lipase for no more than one minute, no more than 2 minutes, no more than 3 minutes, no more than 5 minutes, no more than 8 minutes, no more than 10 minutes, no more than 15 minutes, no more than 30 minutes, no more than 45 minutes, or no more than 60 minutes prior to ingestion. In some embodiments, the liquid nutritional composition is exposed to lipase for no more than 24 hours. In certain embodiments, the lipase is selected from *Chromobacterium viscosum, Pseudomonas fluorescens, Burcholderia cepacia*, and *Rhizopus oryzae* lipases. In certain embodiments, the lipase may be removed from the nutritional formula prior to ingestion. In other embodiments, the liquid nutritional composition comprising LC-PUFA triglycerides, LC-PUFA fatty acid esters, and/or other long-chain triglycerides and/or esters is exposed to lipase immobilized to a solid support prior to ingestion. In some embodiments, the lipase is immobilized to the solid support by covalent binding, ionic binding, or crosslinking. In certain embodiments, the immobilized lipase is encapsulated within or attached to a permeable membrane.

Another aspect of the invention is a method of providing nutrition to a subject in need of dietary LC-PUFAs and/or other long-chain fatty acids, such as people suffering from a reduced ability to break down long-chain triglycerides or long-chain fatty acid esters in the gut, people suffering from pancreatic insufficiency, people suffering from malnutrition, and people who have been receiving total parenteral nutrition, by administering a formula of the invention. In some embodiments, the subject is a premature infant. In other embodiments, the subject is a term infant or toddler. In certain embodiments, the subject is over the age of 50, over the age of 60, or over the age of 70. In some embodiments, the subject is suffering from pancreatic insufficiency. In other embodiments, the formula is administered through a feeding tube. In some embodiments, the nutritional formula of the invention are administered to improve cognitive ability in a person of any age, to prevent chronic lung disease in a pre-term infant, to enhance the neurological development of a pre-term infant, or to treat or prevent a number of other conditions associated with improvement from increased intake of long-chain fatty acids, such as, e.g., EPA, DHA, ARA, LA, and ALA. Such conditions include but are not limited to Alzheimer's disease, bipolar disorder, depression, sepsis, acute respiratory stress, wound healing, cancer, cardiovascular disease, stroke, Parkinson's disease, schizophrenia, diabetes, multiple sclerosis, malnutrition, impaired GI function, and chronic inflammatory diseases such as rheumatoid arthritis, systemic lupus erythematosus, and inflammatory bowel disease.

Another embodiment of the invention provides a method for reducing the time a patient needs total parenteral nutrition by administering a nutritional formula of the invention. As a result, such patients are exposed to a reduced risk of gut atrophy and other complications associated with extended (more than 24 hours) total parenteral nutrition. Such methods may be used to shorten the recovery time of patients suffering from impaired GI function, such as, e.g., malabsorption, short bowel syndrome, IBD, pancreatic insufficiency, malnutrition before or after surgery, chemo- or radiotherapy, or other causes of malnutrition, cancer, wounds, and pressure ulcers. Such patients may receive the nutritional formula of the invention via nasogastric tube. This feeding method may be advantageous in situations where the patient suffers from altered gut motility, impaired pancreatic enzyme secretion due to Systemic Inflammatory Response Syndrome, or other conditions that result in impaired cleavage and absorption of LC-PUFA triglycerides, LC-PUFA fatty acid esters, and/or other long-chain triglycerides or esters of long-chain fatty acids. In an alternate embodiment, where it is advantageous to bypass the stomach, the nutritional formula of the invention may be administered by nasojejunal tube. Other types of feeding apparatus may also be used to deliver the formulas of the invention.

Since healthy subjects may also benefit from increased absorption of LC-PUFAs, e.g., by reducing the risk of cardiovascular disease. Accordingly, in some embodiments, the invention provides methods of improving fat absorption in a healthy subject, comprising feeding to the subject a nutritional formula of the invention.

The invention further provides devices for preparing the nutritional formulas of the invention. In some embodiments, the device comprises a chamber containing at least one lipase, wherein the chamber is capable of holding a liquid nutritional composition so that it is exposed to the lipase. In some embodiments, the lipase in the container is immobilized to the inner surface of the container. In other embodiments, the lipase is immobilized to a support within the chamber. In some embodiments, the device comprises a chamber consisting of a permeable membrane and comprising immobilized lipase within the chamber, such that the liquid nutritional composition may flow through the permeable membrane and come in contact with the lipase, but the lipase cannot pass through the permeable membrane. In some embodiments, the lipase contained within the chamber of a device of the invention is a microbial lipase. In some embodiments, the lipase is selected from bacterial lipases. In some embodiments, the lipase is selected from *Chromobacterium viscosum* lipase, *Pseudomonas fluorescens* lipase, *Burcholderia cepacia* lipase, and *Rhizopus oryzae* lipase. In some embodiments, the lipase is selected from Chromobacterium *viscosum* lipase, *Pseudomonas fluorescens* lipase, and *Rhizopus oryzae* lipase. In some embodiments, the lipase is *Rhizopus oryzae* lipase.

BRIEF DESCRIPTION OF THE DRAWINGS

FIG. 9B illustrates a device for treating formula, according to certain embodiments.

FIG. 10A illustrates a device for treating formula, according to certain embodiments.

FIG. 10B illustrates a device for treating formula, according to certain embodiments.

FIG. 10C illustrates a device for treating formula, according to certain embodiments.

FIG. 11A illustrates a device for treating formula, according to certain embodiments.

FIG. 11B illustrates a device for treating formula, according to certain embodiments.

FIG. 11C illustrates a device for treating formula, according to certain embodiments.

FIG. 17A illustrates a device for treating formula, according to certain embodiments.

LONG-CHAIN POLYUNSATURATED FATTY ACIDS

Figure 1:
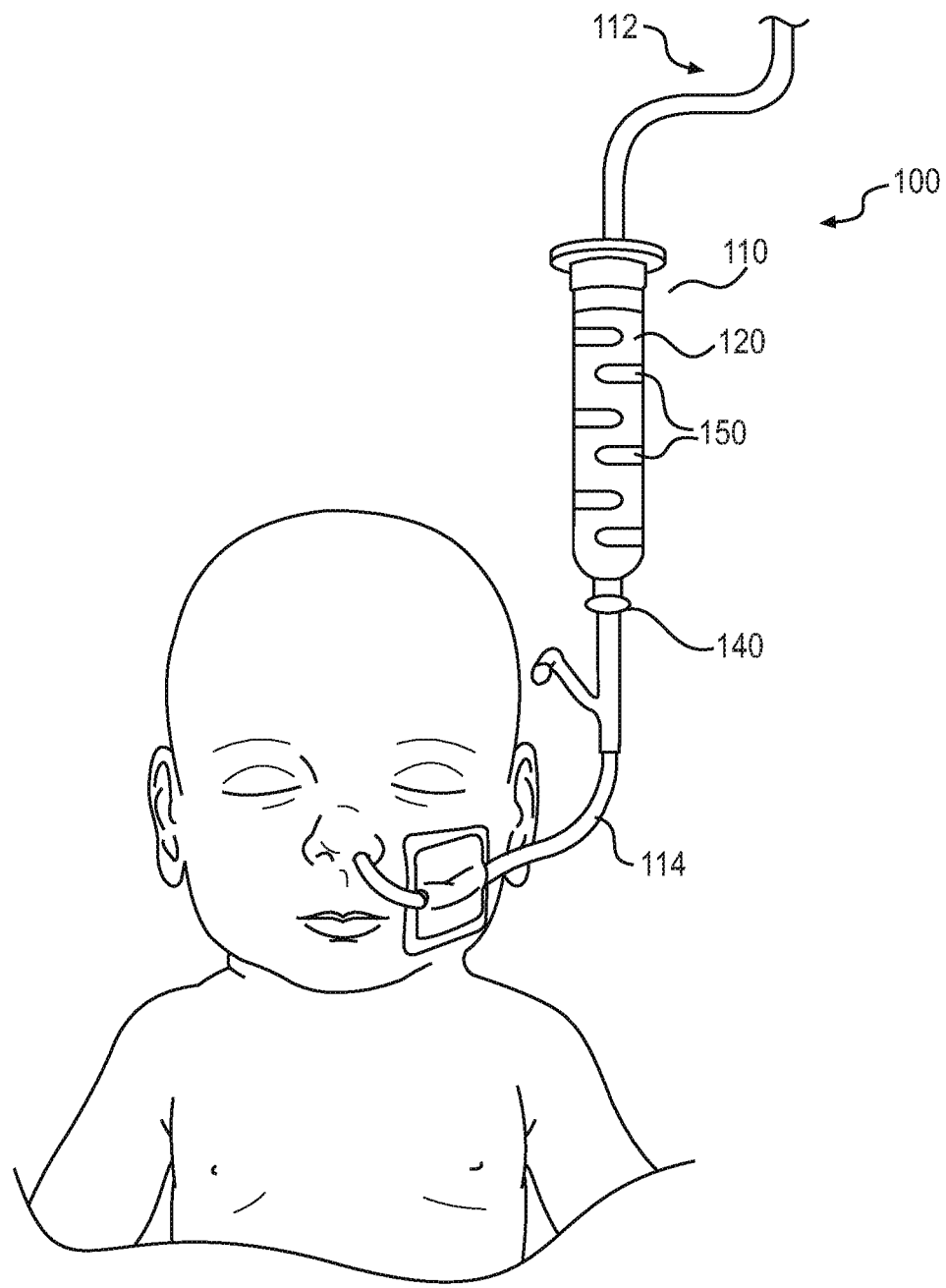
FIG. 1 illustrates a device and method for providing nutrition to an infant, according to certain embodiments.

Long-chain polyunsaturated fatty acids (LC-PUFAs) are hydrocarbon chains containing two or more double bonds. Depending on the position of the first double bond relative to the methyl terminus, an LC-PUFA can be classified as an omega-3 (n-3) or omega-6 (n-6) fatty acid. ALA and LA are parent fatty acids of the n-3 and n-6 PUFA families, respectively. They are considered "essential fatty acids," meaning that humans cannot synthesize them, but rather, must obtain them through diet. This is because mammals lack the ability to introduce double bonds in fatty acids beyond carbon 9 and 10. Blosover et al. *Cell Biology: A Short Course*, John Wiley & Sons, Inc. at 39 (2011). However, humans can make additional long-chain PUFAs starting with ALA and LA.

Both ALA and LA are metabolized to generate other long-chain PUFAs through a series of desaturation and elogation steps. For example, ALA is metabolized to EPA and ultimately DHA. LA is metabolized to ARA, an n-6 fatty acid. Conversion of ALA to DHA and EPA and LA to ARA however, is relatively inefficient. L. Arterburn et al., *Am. J. Clin. Nutr.* 83(suppl):1467S-1476S (2006). Studies have estimated the conversion of ALA to DHA in humans is less than 5%. B. Anderson and D. Ma, *Lipids Health Dis.* 8:33 (2009). The liver contains the most active tissue for converting ALA to DHA and LA to ARA, and therefore plays a key role in providing DHA and ARA to less active tissues or organs, such as the brain. M. Martinez et al., *J. Pediatr.* 120:S129-S138 (1992). Alternatively, these LC-PUFAs can be consumed directly from the diet. DHA and EPA are found in fish, walnuts, and flaxseed oil, whereas ARA is available from animal fat sources, corn oil, soybean oil and sunflower seed oil.

n-3 Fatty Acids

The n-3 fatty acid DHA is critical to neural and retinal development and function. It is the main long-chain PUFA in the neural membrane and is essential for brain function, building of brain circuits, and nerve impulse transmission. As an integral membrane component, DHA contributes to membrane fluidity which is important for maintaining synaptic structures, neurotransmission, and synaptic plasticity. G. Jicha et al., *Clin. Intent. Aging* 5:45-61 (2010). DHA also influences signaling events essential to neuron differentiation and survival, and has effects on the levels and metabolism of neurotransmitters and eicosanoids. The majority of DHA accumulation in the brain occurs at the beginning of the $3^{rd}$ trimester throughout the second year of life. It has been demonstrated that in rodents and primates, an inadequate supply of n-3 PUFA during this period results in impaired learning capacity and neurotransmission. M. Martinez et al., *J. Pediatr.* 120:S129-S138 (1992). Supplementation of DHA in rats that were previously restricted to a DHA-deficient diet rescues performance in memory and learning tasks. W. Chung et al., *J. Nutr.* 138(6):1165-1171 (2008). And in a study of healthy adolescent boys, 8 weeks of DHA supplementation significantly increased functional activation in the dorsolateral prefrontal cortex during performance of an activation task compared to placebo. R. McNamara et al., *Am. J. Nutr.* 91:1060-7 (2010). Thus, DHA is considered important not only in development, but in the maintenance of neuronal function.

DHA is also highly concentrated in the retina and has important effects on photoreceptor differentiation and activation of the visual pigment rhodopsin. H. Lauritzen et al., *Prog. Lipid Res.* 40:1-94 (2001); M. Clandinin et al., *J. Pediatr.* 125:S25-32 (1994). An inadequate supply of DHA early in the development of primates and rodents results in abnormal retinal physiology and reduced visual acuity. M. Reisbick et al., *Dev. Psychol.* 33:387-395 (1997); J. McCann et al., *Am. J. Clin. Nutr.* 82:281-295 (2005). Similarly, in humans, infants fed formula without DHA for the first twelve months of life have been shown to have lower visual acuity than infants fed DHA-supplemented formula. E. Birch et al., *Am. J. Clin. Nutr.* 91(4):848-859 (2010). DHA deficiencies have also been associated with fetal alcohol syndrome, attention deficit hyperactivity disorder, cystic fibrosis, phenylketonuria, unipolar depression, aggressive hostility, and adrenoleukodystrophy. A. Horrocks et al., *Pharmacological Res.* 40(3):211-225 (1999).

The benefits of increased intake of DHA and other n-3 fatty acids have been described for various diseases, including for example, Alzheimer's disease (AD), bipolar disorder (BP), depression, including major depressive disorder (MDD) and post-partem depression, sepsis, acute respiratory stress, wound healing, cancer, cardiovascular disease, stroke, Parkinson's disease, schizophrenia, diabetes, multiple sclerosis, and chronic inflammatory diseases such as rheumatoid arthritis, systemic lupus erythematosus, and inflammatory bowel disease.

For example, clinical trials with AD patients have demonstrated that DHA provides a therapeutic benefit. For a review of studies evaluating the effect of DHA in AD, see G. Jicha and W. Markesbery, *Clin. Interv. Aging* 5:45-61 (2010). Data from in vitro assays, cell culture systems, and murine models of AD support a direct role for n-3 PUFAs in amyloid processing in the brain. And in amyloid-producing transgenic models of AD, supplementation with DHA results in lower levels of $\alpha\beta$. M. Oksman et al., *Neurobiol. Dis.* 23(3):563-572 (2006). In addition to positive clinical trial data in patients with AD, a large study in healthy elderly people with mild memory complaints showed that subjects administered DHA performed better on learning and memory tests after six months compared to those receiving placebo. (Martek Press Release, May 4, 2010). Thus, DHA may also play a beneficial role in preventing AD.

Therapeutic use of DHA has also been investigated in patients with BP and MDD. For a review on DHA in BP, see V. Balencia-Martinez et al., *Expert. Rev. Neurother.* 11(7): 1029-1047 (2011). Due to the difficulties in assessing DHA levels in brain tissue from human patients, the fatty acid composition in erythrocyte membranes from blood samples has been evaluated and was found to contain significantly less DHA in patients with BP and MDD than in healthy controls. R. McNamara et al., *J. Affect. Disord.* 126(1-2): 303-311 (2010). In a post-mortem study, the fatty acid composition of the orbitofrontal cortex had significantly lower levels of DHA in BP patients compared to normal controls. R. McNamara et al., *Psychiatry Res.* 160(3):285-299 (2008). And in a 4-month, double-blind, placebo-controlled study, BP patients receiving n-3 fatty acids had a significantly longer period of remission than the placebo group. A. Stoll et al., *Arch. Gen. Psychiatry* 56(5):407-412

(1999). These studies implicate DHA as therapeutically beneficial in BD and MDD, particularly due to its mood-stabilizing effects.

DHA has also been shown to benefit patients suffering from other forms of depression. For a review, see A. Logan et al., *Lipids Health Dis.* 3:25-32 (2004). A number of studies have found decreased n-3 levels in the blood of patients with depression. Similarly, an increase in plasma DHA was associated with a reduction in women reporting symptoms of post-partem depression. Some placebo-controlled studies have found n-3 treatment improves depressive systems. For a review on the relationship between n-3 levels and depression, see A. Logan et al., *Lipids Health Dis.* 3:25-32 (2004).

In sepsis, an enteral diet enriched with EPA, γ-linolenic acid, and antioxidants improved hospital outcomes and reduced mortality in patients with severe sepsis or septic shock requiring mechanical ventilation. A. Pontes-Arruda et al., *Crit. Care Med.* 34(9):2325-2333 (2006). Similar benefits in ventilator-free days, ICU-free days, reduced new organ dysfunctions, and a decreased mortality rate have been reported in patients with acute respiratory stress fed a diet enriched long-chain PUFAs and antioxidants. J. Gadek et al. *Crit. Care Med.* 27(8):1409-1420 (1999).

N-3 fatty acids are also reported to have beneficial effects in wound healing. Through altering the lipid microenvironement, n-3 fatty acids enhance the reconstitution of epithelial cells and may also help to reduce inflammation. D. Ruthig and K. Meckling-Gill, *J. Nutr.* 129:1791-1798 (1999); J. McDaniel et al. *Wound Repair Regen.* 19(2):189-200 (2011).

EPA and DHA have shown protective effects in cancers, such as prostate and breast cancer. The beneficial effects may be due to anti-inflammatory properties, as well as mechanisms that decrease proliferation and promote apoptosis, such as through downregulation of NF-κB. For a discussion on n-3 fatty acids in cancer, see B. Anderson and D. Ma, *Lipids Health Dis.* 8:33 (2009).

N-3 fatty acids have been associated with beneficial effects in patients with cardiovascular disease and in reducing the risk of cardiovascular disease in healthy people. Similar positive effects have been reported in stroke. Accordingly, the American Heart Association, as well as other health agencies, has issued recommendations for increased intake of n-3 fatty acids in the diet. P. Kris-Etherton et al. *Circulation* 106:2747-2757 (2002). Possible mechanisms for the observed effects of n-3 fatty acids on cardiovascular health include hypotriglyceridemic effects, hypotensive effects, reduction in platelet aggregation, and stabilizing effects on the myocardium itself.

The benefit of n-3 fatty acids in some conditions may be attributed to broad anti-inflammatory effects. EPA and DHA give rise to resolvins, which are anti-inflammatory mediators with inflammation-resolving and immunomodulatory functions. For example, EPA and DHA exhibit inhibitory effects on leukocyte chemotaxis and alter the production of inflammatory cytokines through reducing activation of NF-κB in immune cells. P. Calder, *Int. Rev. Immunol.* 28:506-534 (2009). In general, n-3 PUFAs are associated with reduced pro-inflammatory T cell responses. When n-3 fatty acids are increased in animal diets, the T cell membrane microdomain composition in lipid rafts is altered, resulting in decreased NF-κB activation, IL-2 production, and cellular proliferation. Specifically, n-3 PUFAs affect the distribution and partitioning of the earliest signaling mediators of T-cell activation, such as protein kinase C. Y. Fan et al., *J. Immunol.* 173:6151-6160 (2004). N-3 fatty acids have also been shown to reduce MHC class II expression on dendritic cells, effectively decreasing antigen presentation to T cells, whereas n-6 fatty acids are associated with increased antigen presentation activity. Sanderson et al., *J. Leukoc. Biol.* 62:771-777 (1997). In a monocyte cell line and in intraperitoneal macrophages, DHA and EPA have anti-inflammatory properties mediated through a G protein-coupled receptor 120 (GPR120). As a result, these fatty acids display antidiabetic effects in vivo via suppressing macrophage-induced tissue inflammation. D. Oh et al., *Cell* 142(5):687-698 (2010). The various immunomodulatory functions of n-3 PUFAs indicate they may be influential in many human diseases.

n-6 Fatty Acids

Like n-3 fatty acids, n-6 fatty acids, such as ARA, play a crucial role in neural development and brain function, with ARA accumulation occurring in the brain during pre- and post-natal development. B. Koletzo et al., *J. Perinat. Med.* 36(1):5-14 (2008). N-6 fatty acids are generally important for normal development and immunity, and also stimulate skin and hair growth, maintain bone health, regulate metabolism, and maintain the reproductive system.

Long-Chain PUFA Supplements

For over a decade, health agencies have recommended the consumption of n-3 fatty acids in the diet due to their health benefits. DHA and EPA are commercially available as triglycerides or in esterified form in nutritional supplements or prescription products (e.g., LOVAZA®, OMACOR®, and Vascepa™). DHA supplements may be derived from fish oil, or from vegetarian sources such as flaxseed oil or algae. Supplements may be powder, liquid beverage, or tube-feeding formulas.

Infant formula is subject to the Federal Food, Drug, and Cosmetic Act, which defines infant formula as "a food which purports to be or is represented for special dietary use solely as a food for infants by reasons of its simulation of human milk or its suitability as a complete or partial substitute for human milk." The FDA defines infants as people not more than 12 months old. 21 CFR 105.3(e). The main n-3 fatty acid in human milk is DHA, averaging 7-8 mg/dL (ranging from 0.17% to 1.0% of total fatty acids). R. Yuhas et al., *Lipids* 41(9):851-858 (2006). The amount of DHA in human milk is mostly a reflection of maternal DHA intake.

Commercially available TG-LCPUFA-supplemented infant formulas include Enfamil formulas, such as Enfamil LIPIL® and Enfamil PREMIUM®, Baboo, Earth's Best Organic, Nestle formulas, such as Nestle Gerber GOOD START® and Nestle NAN®, Nutricia formulas such as NEOCATE® and APTAMIL®, Parent's Choice Organic, Pfizer's SMA GOLD®, Similac formulas, such as Similac ADVANCE®, Similac EARLY SHIELD®, and ISOMIL®, and Ultra Bright Beginnings. Other infant formulas may also be supplemented with TG-LCPUFA. TG-LCPUFA-supplemented formulas may be milk-based or soy-based, and may be organic. In the U.S., TG-LCPUFA-supplemented infant formula accounts for approximately 90% of product sales (Mead Johnson Nutrition).

TG-LCPUFA may also be added to follow-on formulas and drinks for toddlers, elderly, and other people needing nutritional support or dietary supplementation with long-chain fatty acids. Examples of such a product include ENSURE®, PEDIASURE®, CARNATION®, BOOST®, CERELAC®, and SOUVENAID®. In addition, specialized formulas that are supplemented with TG-LCPUFA or esters of LC-PUFAs may be used in connection with the methods and devices of the invention in patients requiring tube feeding. For example, enteral formulas are commonly used in pre-term infants, patients with renal failure, gastrointestinal diseases or conditions causing impaired GI function, bowel resection, fat malabsorption, malnutrition, pancreatitis, hyperglycemia/diabetes, liver failure, acute and chronic pulmonary disease, or an immunocompromised state. For a review of commercially available enteral formulas, see A. Malone, *Pract. Gastr.* 29(6):44-74 (2005). Nutritional formulas may be standard, elemental, or specialized based on a patient's disease or condition. Commonly used standard formulas include, for example, ISOCAL®, NUTREN 1.0®, NUTREN 1.5®, NUTREN 2.0®, OSOMLITE 1.0®, OSMOLITE 1.2®, FIBERSOURCE 1.2®, JEVITY 1.2®, JEVITY 1.5®, PROBALANCE®, ISOSOURCE 1.5®, DELIVER 2.0®, NOVOSOURCE 2.0®, and TWOCAL HN®. Elemental formulas may contain macronutrient sources including polymeric and hydrolyzed formulas and may be fiber enhanced. Disease specific formulas include, for example, renal formulas such as MAGNACAL RENAL®, NEPRO®, NOVASOURCE RENAL®, SUPLENA®, and NUTRI-RENAL®.

Gastrointestinal (GI) formulas may used for the nutritional management of patients with impaired GI function including in patients with severe protein or fat malabsorption, extensive bowel resection, cystic fibrosis, cerebral palsy, short bowel syndrome, IBD, pancreatitis, Crohn's disease, diarrhea, GI fistula, Celiac disease, malabsorption syndromes, trauma/surgery, radiation enteritis, intestinal failure, chylothorax. These formulas are also used for early post-operative feeding, trophic feeding, total parenteral nutrition (TPN) alternative, and dual feeding with TPN. GI formulas include, for example, PEPTAMEN®, which is made up of 70% medium-chain triglycerides to decrease the potential for fat malabsorption and 30% long-chain triglycerides, VIVONEX PLUS®, and VIVONEX PEDIATRIC®.

Unfortunately, for people suffering from impaired ability to hydrolyze long-chain triglycerides or esters of long-chain fatty acids, such as, e.g., those with compromised pancreatic output or those suffering from pancreatic insufficiency, even supplementing such formulas with DHA, EPA, and other n-3 fatty acids may not be enough to realize the benefits associated with these compounds. Long-chain triglycerides or fatty acid esters must be metabolized to monoglycerides and/or free fatty acids in order to be properly absorbed in the gut. The invention provides methods of utilizing existing commercially available long-chain PUFA supplements or newly designed formulas supplemented with long-chain PUFAs to provide ready to use formulas containing significantly higher concentrations of long-chain monoglycerides and/or free fatty acids. In some embodiments, the methods will be particularly effective at providing long-chain monoglycerides and/or free fatty acids produced from DHA, EPA, and ARA triglycerides or esterified DHA, EPA, and ARA so that the formula will provide the maximum benefit associated with these critical fatty acids to people who otherwise would not be able to hydrolyze and absorb them.

Reduced Ability to Hydrolyze Long-Chain Triglycerides and Fatty Acid Esters

Pancreatic insufficiency is one of the conditions that leads to a reduced ability to hydrolyze long-chain triglycerides. Pancreatic insufficiency is characterized by insufficient production of exocrine pancreatic enzymes, including pancreatic lipase. Pancreatic insufficiency may occur naturally during various stages of human life. For example, the secretion of pancreatic lipase begins at low levels at around 30 weeks gestation and remains low during the first year of life. Therefore, infants, and especially pre-term infants, may experience pancreatic insufficiency. As a result, if they are not breast feeding, these infants are susceptible to poor fatty acid hydrolysis and absorption, and are deprived of the benefits associated with ingestion of DHA, EPA, and other LC-PUFAs.

On the other end of the spectrum, otherwise healthy elderly may also experience pancreatic insufficiency or other reduced ability to hydrolyze LC-PUFA triglycerides or esterified LC-PUFAs due to changes in the pancreas that occur as part of the natural aging process. These changes may include atrophy, fibrosis, sclerosis, or lipomatosis of the pancreas. As a result, the elderly may experience symptoms of maldigestion including malnutrition, steatorrhoea, diarrhea, abdominal pain and weight loss because of reduced exocrine pancreatic enzyme secretion. K. Herzig et al., *BMC Geriatrics* 11:4-8 (2011).

Pancreatic insufficiency or other reduced ability to hydrolyze LC-PUFA triglycerides or esterified LC-PUFAs may also result from disease or trauma. For example, pancreatitis is a condition of inflammation in the pancreas which results in pancreatic insufficiency. Pancreatitis may be either acute or chronic, and includes pancreatitis caused by alcoholism, idiopathic chronic pancreatitis, hereditary pancreatitis, traumatic pancreatitis, acute necrotizing pancreatitis, and autoimmune pancreatitis. Cystic fibrosis is also a cause pancreatic insufficiency, particularly in children and adolescents. Disorders that result in a decrease in intraduodenal pH, such as gastrinoma (Zollinger-Ellison syndrome), can inactivate lipase and cause pancreatic insufficiency. Pancreatic insufficiencies can also be caused by surgeries of the gastrointestinal tract in which portions of the stomach or pancreas are removed, pancreatic cancer, gastrointestinal diseases such as stomach ulcers, celiac disease, or Crohn's disease, or in autoimmune disorders such as systemic lupus erythematosus (SLE) or inflammatory bowel disease (IBD).

Other causes of a reduced ability to digest TG-LCPUFAs, esterified LC-PUFAs, and/or other long-chain triglycerides and fatty acid esters include, for example, irritable bowel syndrome, hypertriglyceridemia, malnutrition, including severe protein-calorie malnutrition, pancreatic and duodenal neoplasms, abdominal radiotherapy, hemochromatosis, primary sclerosing cholangitis, primary biliary cirrhosis, Shwachman's syndrome, trypsinogen deficiency, enterokinase deficiency, or an isolated deficiency of lipase. D. Kasper et al., *Harrison's Principles of Internal Medicine* 16$^{th}$ Ed. (2004). A reduced ability to digest long-chain triglycerides or esterified long-chain PUFAs may also result from bowel resection, cystic fibrosis, cerebral palsy, short bowel syndrome, IBD, pancreatitis, Crohn's disease, diarrhea, GI fistula, Celiac disease, malabsorption syndromes, trauma/surgery, particularly GI trauma or surgery, radiation enteritis, intestinal failure, chylothorax, cancer, particularly pancreatic or GI cancer, and/or wound healing. Although the exact cause is unknown, children with attention deficit hyperactivity disorder (ADHD) have also reduced levels of LC-PUFAs. Burgress et al., *Am. J. Clin. Nutri.* 71(suppl): 327S-30S (2000).

Cystic fibrosis (CF) patients, for example, have been shown to have reduced levels of LC-PUFAs. Peretti et al., *Nutrition & Metabolism* 2:11-28 (2005). CF patients receiving pancreatic enzyme replacement therapy frequently continue to suffer from fat malabsorption. Kalivianakis, *American Journal of Clinical Nutrition* 69:127-134 (1999). In some embodiments, the invention provides formulas and methods for improving absorption of fats, such as, e.g., LC-PUFAs, in CF patients. In some embodiments, the invention provides formulas and methods for inducing weight gain in CF patients While cachexia and weight loss are common in the advanced stages of many cancers due to the catabolic state of tissues, diversion of nutrients, and malabsorption in advanced stages, pancreatic cancer (PC) is unusual in that weight loss and malabsorption are present in 80%-90% of patients at the time of diagnosis. Malabsorption from exocrine deficiency largely accounts for weight loss and is due to loss of pancreatic parenchyma, blockage of the pancreatic duct preventing enzymes from reaching the gut, and surgical procedures. The common end result of all these mechanisms is steatorrhea and weight loss. Damerla et al., *J of Support Oncology* 6:393-396 (2008). Weight stabilization in PC is associated with improved survival and quality of life. Davidson et al., *Clinical Nutrition* 23, 239-247 (2004). In some embodiments, the invention provides formulas and methods for improving absorption of fats, such as, e.g., LC-PUFAs, in PC patients. In some embodiments, the invention provides formulas and methods for inducing weight gain in PC patients.

Some embodiments of the invention improve upon current treatment options for pancreatic insufficiency and other conditions that reduce the ability to hydrolyze TG-LCPUFAs, esterified LC-PUFAs, and/or other long-chain triglycerides and fatty acid esters. In a patient with reduced ability to hydrolyze TG-LCPUFAs, esterified LC-PUFAs, and/or other long-chain triglycerides and fatty acid esters, merely increasing consumption of these nutrients without improving hydrolysis can cause steatorrhea, abdominal pain, cramping, diarrhea, and other gastrointestinal complications. Pancreatic enzyme replacement therapy can also lead to complications. It has been observed that large amounts of pancreatic digestive enzymes can damage the large intestine resulting in fibrosing colonopathy. D. Bansi et al., *Gut* 46:283-285 (2000); D. Borowitz et al. *J. Pediatr.* 127:681-684 (1995). Another significant danger posed by lipase supplements is allergic reaction, as many commercial lipase supplements are derived from animal sources. Thus, embodiments of the invention that provide pre-hydrolyzed long-chain triglycerides or long-chain PUFA esters, with or without added lipase, will provide better and safer methods for treating pancreatic insufficiency or other reduced ability to digest long-chain triglycerides or esterified long-chain PUFAs.

While both n-3 and n-6 fatty acids are important during development, n-3 fatty acids are believed to be more critical than n-6 fatty acids later in life. In some subjects, particularly some adults, it may be desirable to increase the ratio of (DHA and EPA):ARA. In particular, cystic fibrosis patients may benefit from increasing the ratio of (DHA and EPA): ARA in their plasma. Unfortunately, currently available adult formulas generally have a low ratio of n-3:n-6 fatty acids. Moreover, in subjects with impaired hydrolysis of TG-LCPUFAs, simply increasing consumption of n-3 TG-LCPUFAs is unlikely to significantly improve the (DHA and EPA):ARA ratio in the subject, and the resulting increase in undigested TG-LCPUFAs could cause gastrointestinal problems.

Accordingly, some embodiments of the invention provide formulas and methods for increasing the ratio of (DHA and EPA):ARA in a subject, particularly in an adult subject. For example, some embodiments provide methods of preparing an adult formula in which a formula comprising n-3 triglycerides and/or esters is exposed to a lipase that hydrolyzes n-3 triglycerides and/or esters. In some embodiments, the prepared formula comprises a higher ratio of n-3:n-6 monoglycerides and/or free fatty acids, e.g., a higher ratio of free DHA and EPA to free ARA, than in the corresponding formula without lipase treatment. In some embodiments, the formula comprises more n-3 monoglycerides and/or free fatty acids than n-6 monoglycerides and/or free fatty acids, e.g., more free DHA and EPA than free ARA. In some embodiments, the formula is prepared by exposing it to a lipase that has higher activity toward n-3 triglycerides and/or esters than n-6 triglycerides and/or esters. In some embodiments, the enzyme is RO enzyme. The invention also provides a formula in which the ratio of n-3:n-6 free fatty acids and/or monoglycerides is higher than the ratio of n-3:n-6 fatty acids found in the subject's plasma, e.g., a formula in which the ratio of free DHA and EPA to free ARA is higher than in the subject's plasma. The invention also provide methods in which such a formula is administered to an adult subject. In some embodiments, the subject has cystic fibrosis.

Reduced Ability to Hydrolyze Long-Chain Fatty Acids in Pre-Term Infants

Long-chain PUFAs are critical in infants for normal nervous system and retinal development and are highly accumulated in the cell membranes of the brain and retina starting at 30 weeks gestation. C. Martin et al., *J. Pediatr.* 159(5):743-749 (2011); A. Lapillone et al., *Leukotrines Ess. Fatty Acids* 81:143-150 (2009); J. McCann et al., *Am. J. Clin. Nutr.* 82:281-295 (2005); M. Martinez et al., *J. Pediatr.* 120:S129-S138 (1992). Normally fatty acids, including DHA, EPA, and ARA, as well as the lipases needed to break these fatty acids down to monoglycerides and free fatty acids are provided to the fetus through the placenta and then to infants through breast milk. Pre-term infants are at a significantly higher risk for an inadequate supply of fatty acids due to the shortened gestation time followed by their dependence on external sources for fatty acids after birth. C. Martin et al., *J. Pediatr.* 159(5):743-749 (2011). Additionally, because pre-term infants do not produce sufficient levels of pancreatic lipase, they consequently have difficulty hydrolyzing any long-chain fatty acids that are provided in their formula.

It has been demonstrated that pre-mature infants have less DHA and lower DHA/ARA ratios in both the brain and retina compared to a full-term infant. M. Martinez et al., *J. Pediatr.* 120:S129-S138 (1992). Additionally, in a retrospective study of the fatty acid profile of pre-term infants, inadequate levels of long-chain PUFAs were associated with an increase of chronic lung disease and sepsis, possibly due to dysregulated immune response. C. Martin et al., *J. Pediatr.* 159(5):743-749 (2011). These studies and others suggest that, even with formulas supplemented with DHA and other long-chain triglycerides or long-chain fatty acid esters, ensuring adequate levels of long-chain PUFAs in pre-term infants is a significant and potentially unmet need. The formulas, methods, and devices of the invention will allow pre-term infants to receive sufficient amounts of long-chain fatty acids to recognize the associated medical benefits.

Reduced Ability to Hydrolyze Long-Chain Fatty Acids in Formula-Fed Infants

Infants fed formula that have not been supplemented with fatty acids may also experience deficits in long-chain PUFAs. The levels of long-chain PUFAs were found to decline in infants fed unsupplemented formula compared to infants fed breast milk. B. Koletzo et al., *J. Perinat. Med.* 36(1):5-14 (2008). Even infants fed breast milk can experience deficits in n-3 fatty acids as the amount of DHA in breast milk varies and is correlated with maternal dietary intake. A positive correlation between the amount of DHA in breast milk and visual and language development in breast-fed infants has been described. S. Innis, *J. Pediatr.*

143:S1-S8 (2003). Thus, a diet containing DHA is recommended for women that are breast-feeding. For formula-fed infants, all major formula manufacturers have introduced premium infant formulas with fats containing DHA and ARA. However, reports on the benefits of those DHA and ARA enriched formulas have been mixed. Some studies have shown significant advantages in cognitive development when infants received long-chain PUFA containing formula, while others have not. B. Koletzo et al., *J. Perinat. Med.* 36(1):5-14 (2008); E. Sarkadi-Nagy et al., *J. Lipid Res.* 45:71-80 (2004). Recently, infants fed Enfamil LIPIL® containing DHA and ARA during the first year of life experienced improved immune outcomes, including improved respiratory health, compared to infants fed the same formula without lipids. E. Birch et al., *J. Pediatr.* 156(6):902-906 (2010). Overall, however, the pre-clinical data to date has not shown consistent benefits of current long-chain PUFAs-supplemented formulas for infant development.

One explanation for the inconsistent results in these studies is that some infants are not able to absorb the necessary amount of critical fatty acids through the gut even when ingesting formula supplemented with long-chain triglycerides or long-chain fatty acid esters. This inability to absorb fatty acids may be due to the infants' low levels of endogenous pancreatic lipase. Because lipases are typically transferred to an infant through breast milk, formula-fed infants may not have sufficient levels of lipase to break down the long-chain PUFAs or PUFA esters to monoglycerides and/or free fatty acids, for absorption by the gut. As a result, infants fed LC-PUFA-supplemented formula still have less absorption of LC-PUFAs compared to infants fed breast milk. Once again, there is a clear need to not simply provide fatty acid supplements, but to enable hydrolysis and absorption of these fatty acids.

Adding lipase to government regulated infant formulas (or e.g., medical nutritional formulas) could require significant development work to screen, stabilize and formulate a suitable lipase supplement. In unregulated formulas, without sufficient testing, issues involving lipase stability, lack of specificity, purity, and/or interference with other materials may result in the use of excess or potentially harmful levels of enzyme. Adding copious amounts of a new substance, beyond regulatory hurdles, also introduces another variable that could affect how well a person with reduced ability to hydrolyze long-chain triglycerides, particularly an infant, will tolerate a formula. This problem persists in formulas described, e.g., in U.S. Pat. No. 5,902,617 (Pabst) and U.S. Pat. No. 4,944,944 (Tang).

Embodiments of the invention solve these various problems by providing a nutritional formula that, as-fed, provides increased amounts of essential monoglycerides and free fatty acids that may be readily absorbed through the gut of an infant. As a result, formula-fed subjects can be provided with the benefits of DHA, EPA, and ARA. In some embodiments, the nutritional formula introduces no new ingredients except pre-hydrolyzed fats that are present in existing formulas. In certain embodiments, formula-fed babies are provided the fatty acid benefits obtained by breast-fed infants, without exposure to lipase supplements. In other embodiments, nutritional formula of the invention contains a highly specific lipase that allows for the use of a minimal amount of lipase added to infant formula to provide increased amounts of long-chain monoglycerides and free fatty acids, particularly DHA, EPA, and ARA.

In some embodiments, the nutritional formula leads to improved absorption of fatty acids. In some embodiments, a subject ingests the nutritional formula for 3 days, 5 days, 7, days, 10 days, 14 days, 30 days, 60 days, or more. In some embodiments, such ingestion of a nutritional formula of the invention reduces the total fat in the stool, and specifically can reduce the levels of DHA, ARA, and/or EPA in the stool. In some embodiments, this reduction is measured relative to the subject's stool composition prior to beginning to ingest the nutritional formula. In some embodiments, this reduction is measured relative to the stool composition of a subject fed a nutritional formula that has not been exposed to lipase prior to ingestion, such as a currently available nutritional formula. The levels of total fat, DHA, ARA, and/or EPA in the stool may be reduced by at least 10%, at least 20%, at least 30%, at least 40%, at least 50%, at least 60%, at least 70%, at least 80%, at least 90%, or more. In certain embodiments, the levels of total fat, DHA, ARA, and/or EPA in the stool are reduced by between 50 and 80%. In some embodiments, the level of total fat in the stool is reduced by at least 50%. In some embodiments, the level of at least one LC-PUFA (such as DHA, ARA, or EPA) in the stool is reduced by at least 50%. In some embodiments, the level of at least one LC-PUFA (such as DHA, ARA, or EPA) in the stool is reduced by at least 60%. In some embodiments, the levels of DHA, ARA, and EPA in the stool are each reduced by at least 50%. In some embodiments, the levels of DHA, ARA, and EPA in the stool are each reduced by at least 60%. In some embodiments, ingestion of the nutritional formula improves plasma, erythrocyte, and tissue accretion of fat levels, including levels of DHA and ARA. Tissues may include retina, heart, adipose, and kidney tissue. In some embodiments, ingestion of the nutritional formula increases the level of DHA, ARA, or both in the plasma, erythrocytes, or both. In some embodiments, ingestion of the nutritional formula increases the level of DHA, ARA, or both in the retina. In some embodiments, ingestion of the nutritional formula increases the level of DHA, ARA, or both in the heart. In some embodiments, ingestion of the nutritional formula increases the plasma level of triglycerides, cholesterol, HDL, and/or LDL. In some embodiments, ingestion of the nutritional formula increases the ratio of HDL to LDL in the subject's plasma.

In some embodiments, ingestion of the nutritional formula increases the plasma level of vitamin A and/or vitamin E. Without intending to be bound by theory, it is believed that this increase is due to the fact that vitamins A and E are typically provided as esters, which must be hydrolyzed. Exposure to lipase in various methods and compositions of the invention is believed to improve hydrolysis of these vitamin esters, leading to greater accumulation of vitamins A and E in the plasma.

In some embodiments, ingestion of the nutritional formula has beneficial effects without significantly increased accumulation of fat in the liver. Fatty liver disease (FLD) is characterized by increased accumulation of fat, especially triglycerides, in the liver cells. The condition is also associated with other diseases that influence fat metabolism. It is normal for the liver to contain some fat and by itself, this causes no symptoms. In some patients, fatty liver may be accompanied by hepatic inflammation and liver cell death (steatohepatitis). There is also an association with liver cancer (hepatocellular carcinoma). Insulin resistance, as well as increased consumption of carbohydrates and saturated fatty acids, and a low intake of fiber and omega-3 fatty acids, are all positively associated with the pathogenesis of FLD.

Causes of FLD include diet, medications, diseases, and medical conditions. Consumption of excess calories can cause FLD; the excess caloric intake overwhelms the liver's ability to metabolize fat in a normal fashion, which results in fat accumulation in the liver. A number of medications, including as tamoxifen, amiodarone injection, amiodarone oral, and methotrexate are associated with FLD. Fatty liver is also associated with type II diabetes, obesity, and high triglyceride levels in the blood, celiac disease, and Wilson's disease (abnormality of copper metabolism), rapid weight loss, and malnutrition.

Lipase

Pancreatic insufficiency and other conditions associated with reduced ability to hydrolyze long-chain triglycerides or long-chain fatty acid esters is currently treated with supplementary digestive enzymes, including pancreatic lipase. However, pancreatic enzymes, and particularly pancreatic lipase present in these supplements, are often sensitive to degradation by gastric acid and pepsin so that only a small fraction of the ingested enzymes reach the duodenum in active form. E. Ville et al., *Digestion* 65:73-81 (2001). Unfortunately, many of the acid protective coatings have potential safety concerns for infant populations or immune compromised patients since a significant portion of the delivered weight is the plastic coating. Moreover, although acid protective coatings have helped, some degree of malabsorption persists, causing patients with pancreatic insufficiency to require increasing doses of enzyme supplements. This persistence of fatty acid malabsorption of enterally coated enzymes may be due to the fact that the duodenum and upper jejunum in patients with pancreatic insufficiency are often acidic environments, so that the expected raise in pH is not achieved and the protective coating is not properly dissolved to release the enzyme. D. Graham, *New England J. Med.* 296(23):1314-1317 (1977). Both of these problems have been addressed by increasing the dose of lipase administered. Unfortunately, as previously noted, high doses of pancreatic enzyme supplement have been found to be associated with fibrosing colonopathy. Thus, some embodiments of the invention provide nutritional formulas that comprise higher percentages of long-chain monoglycerides and/or free fatty acids without containing added lipase. Some embodiments provide nutritional formulas that comprise an optimized dose of lipase, as described herein.

Lipases can be obtained from animal, plant, and many natural or genetically engineered microorganisms. Many, if not most, commercially available dietary lipase supplements are derived from animals and are particularly susceptible to degradation by digestive enzymes. A less frequently used alternative is microbial lipase, i.e., lipase produced in bacteria or fungus, such as, e.g., yeast. Microbial lipases retain activity over a wider pH range than animal or plant lipases, thus eliminating the need for enteric coated tablets. However, microbial enzymes tend to be degraded by trypsin in the small intestine, thereby reducing their availability to breakdown triglycerides and esters in the gut. In certain embodiments, the lipase used in the formulas, methods, or devices of the invention are bacterial lipases, fungal lipases, or both.

The specificity and kinetics of individual lipases can vary significantly. Specificity of lipases is controlled by the molecular properties of the enzyme, structure of the substrate and factors affecting binding of the enzyme to the substrate. Types of specificity include substrate specificity, i.e., a given lipase may be more active in breaking down a type of fatty acid than another lipase, and positional specificity, which involves preferential hydrolysis of ester bonds in positions 1 and/or 3 of the glycerol backbone of a triglyceride.

It has now been determined that lipase produced by *Chromobacterium viscosum*, *Pseudomonas fluorescens*, *Burcholderia cepacia*, and *Rhizopus oryzae* have greater specificity for DHA, EPA, and ARA than other lipases, such as lipase produced by *Candida rugosa*, *Rhizomucor miehei*, *Penicilium camemberti*, *Aspergillus niger*, and *Aspergilis oryzae*. As a result, lipase supplements, or lipase supplemented nutritional products comprising *Chromobacterium viscosum*, *Pseudomonas fluorescens*, *Burcholderia cepacia*, and/or *Rhizopus oryzae* will provide increased hydrolysis of TG-DHA, TG-EPA, and/or TG-ARA. Accordingly, one aspect of the invention provides lipase supplements or lipase supplemented nutritional products comprising Chromobacterium *viscosum* lipase, *Pseudomonas fluorescens* lipase, *Burcholderia cepacia* lipase, and/or *Rhizopus oryzae* lipase. In some embodiments, the lipase is *Chromobacterium viscosum* lipase, *Pseudomonas fluorescens* lipase, or *Rhizopus oryzae* lipase. In certain embodiments, the lipase is *Rhizopus oryzae* lipase.

Reference to the lipase of certain species, such as *Chromobacterium viscosum* lipase, *Pseudomonas fluorescens* lipase, *Burcholderia cepacia* lipase, and *Rhizopus oryzae* lipase, does not necessarily mean that the lipase was prepared directly from the native host species. For example, the same lipase could be produced recombinantly in another host cell.

Another aspect of the invention is a method of increasing the absorption of DHA, EPA, and/or ARA by administering one or more of *Chromobacterium viscosum*, *Pseudomonas fluorescens*, *Burcholderia cepacia*, and *Rhizopus oryzae* lipases, as a dietary supplement, or by pre-hydrolyzing a formula containing DHA, EPA, and/or ARA with one or more of these enzymes. In some embodiments, the lipase is Chromobacterium *viscosum* lipase, *Pseudomonas fluorescens* lipase, or *Rhizopus oryzae* lipase. An additional aspect of the invention provides lipases with specific activities for DHA, EPA, and/or ARA that are comparable to the specific activities of one or more of *Chromobacterium viscosum*, *Pseudomonas fluorescens*, *Burcholderia cepacia*, and *Rhizopus oryzae* as determined by reverse-phase high performance liquid chromatography (RP-HPLC) and described in Example 1. In some embodiments, the lipase has specific activities for DHA, EPA, and/or ARA that are comparable to the specific activities of one or more of Chromobacterium *viscosum* lipase, *Pseudomonas fluorescens* lipase, or *Rhizopus oryzae* lipase. One embodiment of the invention is a nutritional formula that contains less than 5,000 units of lipase (with units assessed in a standard olive oil assay, such as described in *Pharmaceutical Enzymes: Properties and Assay Methods*, R. Ruyssen and A. Lauwers (Eds) Scientific Publishing Company, Ghent, Gelgium (1978)). In other embodiments, the nutritional formula contains less than 3,000 units of lipase. In some embodiments, the nutritional formula contains less than 1,000 units. In certain embodiments, the formula containing less than 5,000, less than 3,000, or less than 1,000 units of lipase is an infant formula or a medical nutritional formula.

Immobilized Lipase

Processes for immobilizing enzymes and other proteins to insoluble supports are well-known and described in the literature. Immobilization of lipase may improve the stability of the enzyme, render it reusable, and allow products to be readily separated from the enzyme without contamination by lipase. In some embodiments, the lipase is covalently bound to a solid support, however, non-covalent binding may also be used. Suitable methods of immobilization of lipase include, for example, adsorption, ionic binding, covalent binding, cross-linking, encapsulation, and entrapment onto hydrophobic or hydrophilic polymeric and inorganic matrices. See Y. Ren et al., *BMC Biotechnol.* 11:63 (2011); V. R. Murty et al., *Biotechnol. Bioprocess Eng.* 7:57-66 (2002). Lipase may be immobilized by binding directly to a support material or through a linker. See, e.g., Stark and Holmberg, *Biotechnol. and Bioeng.* 34(7):942-950 (1989).

Immobilization by adsorption is reversible and typically involves hydrophobic forces. It is simple and inexpensive, but has the disadvantage of incomplete immobilization or leaking enzyme from the insoluble support. Examples of immobilized lipase using this method can be found in E. Lie et al., *Chem. Technol. and Biotechnol.* 50:549-553 (1991) (*Candida cylindracea* lipase, zeolite support); M. Basri et al., *J. Chem. Technol. and Biotechnol.* 59:37-44 (1994) (*Candida rugosa* lipase; polymer support); H. Gunnlaughsdottir et al., *Enzyme and Microbiol. Tech.* 22:360-367 (1998) (*Humicola lanuginose* lipase; glass beads support). Supports suitable for immobilization by adsorption include, e.g., ceramic beads such as Toyonite (Toyo Denka Kogyo Co., Ltd.).

Ionic binding is based on electrostatic interactions between the lipase and differently charged ionic groups on matrices such as e.g., DEAE-cellulose or DEAE-Sephadex on a solid support. Ionic binding causes minimal change to the conformation of the lipase and yields immobilized lipase with high activity in most cases. It should be kept in mind, however, that although the binding force between the enzyme and the support is stronger than when using adsorption, it is not as strong as covalent binding and thus, leaking of lipase from the support may occur.

Covalent binding is based on covalent bonds between a support material and a functional group on an amino acid on the surface of the lipase. The functional groups that may take place in this binding of enzyme to support can be amino, carboxyl, sulfhydryl, hydroxyl, imidazole, or phenolic groups which are not essential for the catalytic activity of the lipase. In order to protect the active site, immobilization can be carried out in the presence of substrate or a competitive inhibitor. A significant advantage to using covalent binding of lipase to a support material is the strength of the bond, i.e., the stability of the immobilization. For an example of lipase immobilized by covalent binding, see S. Emi et al., *European Polymer Journal* 30(5):589-595 (1994). Supports suitable for covalent binding include, e.g., Immobead™ (ChiralVision).

Cross-linking involves joining the lipase to itself to form a three-dimensional structure or joining the lipase to a solid structure using a crosslinking agent. For example, lipase may be cross-linked to chitosan beads. See S. H. Chiou et al., *Prep. Biochem. Biotechnol.* 37(3):265-275 (2007). Immobilization of lipase by encapsulation usually involves the formation of a porous coating or semi-permeable membrane around the lipase so that the lipase is contained inside the porous material, but triglycerides and esters may pass freely through. Immobilization of lipase by entrapment involves restricting the movement of the enzyme by trapping it in a lattice structure. Alginate beads may be used for this type of immobilization. I. Bushan et al., *J. Bioactive and Compatible Polymers* 23(6):552-562 (2008). Synthetic and natural polymers may also be used. See also, G. Fernandez-Lorente et al., *J. Am. Oil Chem. Soc.* (published online 14 Dec. 2010) and G. Fernandez-Lorente et al., *J. Am. Oil Chem. Soc.* 88:1173-1178 (2011).

In certain embodiments, the formulas, methods, and devices of the invention will utilize lipase that has been crystallized and cross-linked for increased stability as described in U.S. Pat. No. 6,541,606 (Margolin), either with or without another form of immobilization, such as encapsulation.

In some embodiments, lipase is immobilized to magnetic nanoparticles (MNPs). These MNPs may be coated by linkers or polymers containing amino or epoxy functional groups to which the lipases are reacted. One suitable coating for MNPs is, e.g., polydopamine. See, e.g., Y. Ren et al., *BMC Biotechnology* 11:63 (2011). The use of MNPs for lipase immobilization has advantages such as biocompatibility, supermagnetism, small size, and low toxicity. The magnetic properties of the nanoparticles facilitate removal of the lipase from solution and also provides another means for attaching the MNP-lipase to a solid support.

In some embodiments, the immobilized lipase is a microbial lipase. In some embodiments, the immobilized lipase is selected from bacterial lipases. In some embodiments, the immobilized lipase is one or more lipases selected from *Chromobacterium viscosum*, *Pseudomonas fluorescens*, *Burcholderia cepacia*, and *Rhizopus oryzae*.

In certain embodiments, the lipase (whether immobilized or not) is added to formula for 1, 2, 3, 4, 5, 10, 20, 30 minutes or more. The hydrolysis of LC-PUFA triglycerides and esters is measured by RP-HPLC. In certain embodiments, the percent hydrolysis of LC-PUFA triglycerides and esters is 10%, 20%, 30%, 40%, 50%, 60%, 70%, 80%, 90%, or 100% by 30 minutes. In embodiments, the percent hydrolysis of LC-PUFA triglycerides and esters is 10%, 20%, 30%, 40%, 50%, 60%, 70%, 80%, 90%, or 100% by 20 minutes. In embodiments, the percent hydrolysis of LC-PUFA triglycerides and esters is 10%, 20%, 30%, 40%, 50%, 60%, 70%, 80%, 90%, or 100% by 10 minutes. In certain embodiments, the lipase is *Rhizopus oryzae* lipase.

Devices Comprising Immobilized Lipase

According to various embodiments, the present disclosure provides devices and methods for preparing nutritional products. The devices and methods can be used to expose infant formula or other nutritional products to lipases prior to consumption. The lipases will accordingly breakdown fats and oils with subsequent release of free fatty acids and monoglycerides. The devices and methods will allow convenient means for preparing formula or other nutritional products. In some embodiments, the devices and methods allow infants or others who consume the products to avoid consuming exogenous lipase. In some embodiments, the devices and methods allow for production of formulas that contain monoglycerides and/or free fatty acids but do not contain any significant amount of lipase (as determined by ELISA).

FIGS. 1, 2A-2C, 3A-3C, 4A-4B, 5A-5B, 9A-9C, 10A-10C, 11A-11C, 12, 13A-13B, 14, 15, 16, 17A-17B, 18, 19, 20, and 21 illustrate devices according to various embodiments of the present disclosure. As shown in FIG. 1, devices 100 of the present disclosure can include a container 110 configured to hold infant formula 120 or other liquid nutritional products. As described in detail below, the container 110 can include lipases that are immobilized such that formula 120 that is fed to the infant through a nasogastric tube 114 or other feeding mechanism (e.g., a baby bottle) does not contain lipases in any appreciable amount. For example, the lipases can be immobilized on or in structures 150 found along the wall or otherwise within the container such that the lipases are in fluid contact with formula 120 within the container. Further, as is discussed with reference to various embodiments below, formula can be added to the container 110, in various ways to allow enzymatic treatment of lipases within the container 110. For example, fluid can be fed through a tube 112 or poured into the container, and can be subsequently passed through a nasogastric tube or other device for feeding.

Throughout this disclosure, the devices and methods will be referred to for use in treating or preparing nutritional formula, such as, e.g., infant formula and medical nutritional formula. It will be appreciated that the devices and methods can be used to treat or prepare any type of nutritional formula for which it may be beneficial to provide lipase treatment prior to consumption. Such products can include any nutritional formula to be consumed by someone with pancreatic insufficiency or other reduced ability to hydrolyze long-chain triglycerides or esterified long-chain PUFAs.

FIGS. 2A-2C and 3A-3C illustrate more detailed devices, according to various embodiments. As shown, the devices 200-202, 300-302 can include a container 210, 310 for holding liquid formula. The container 210, 310 can include a variety of different types and configurations. For example, the container 210, 310 can include a glass or plastic jar or vial, a bag (e.g, silicone or other flexible material like an IV saline bag), a cylindrical container such as a syringe barrel, or other container that is sized and shaped to hold a desired amount of formula or other product.

As noted, the devices of the present disclosure can allow formula to be exposed to lipases to obtain the desired enzymatic effects, while allowing the formula to then be conveniently consumed without consuming lipases. Accordingly, in various embodiments, lipases are immobilized within the container 210, 310 such that, when the formula is removed (e.g., through a nasogastric tube, nipple for a baby bottle, or by transferring the formula to another container), the lipases remain in the container 210, 310 or can be removed from the formula prior to consumption. In other embodiments, lipases are immobilized within the container 210, 310, e.g., on removable solid supports, such that the lipases can be easily removed from the container, while leaving the formula in the container for later consumption.

Figure 2A:
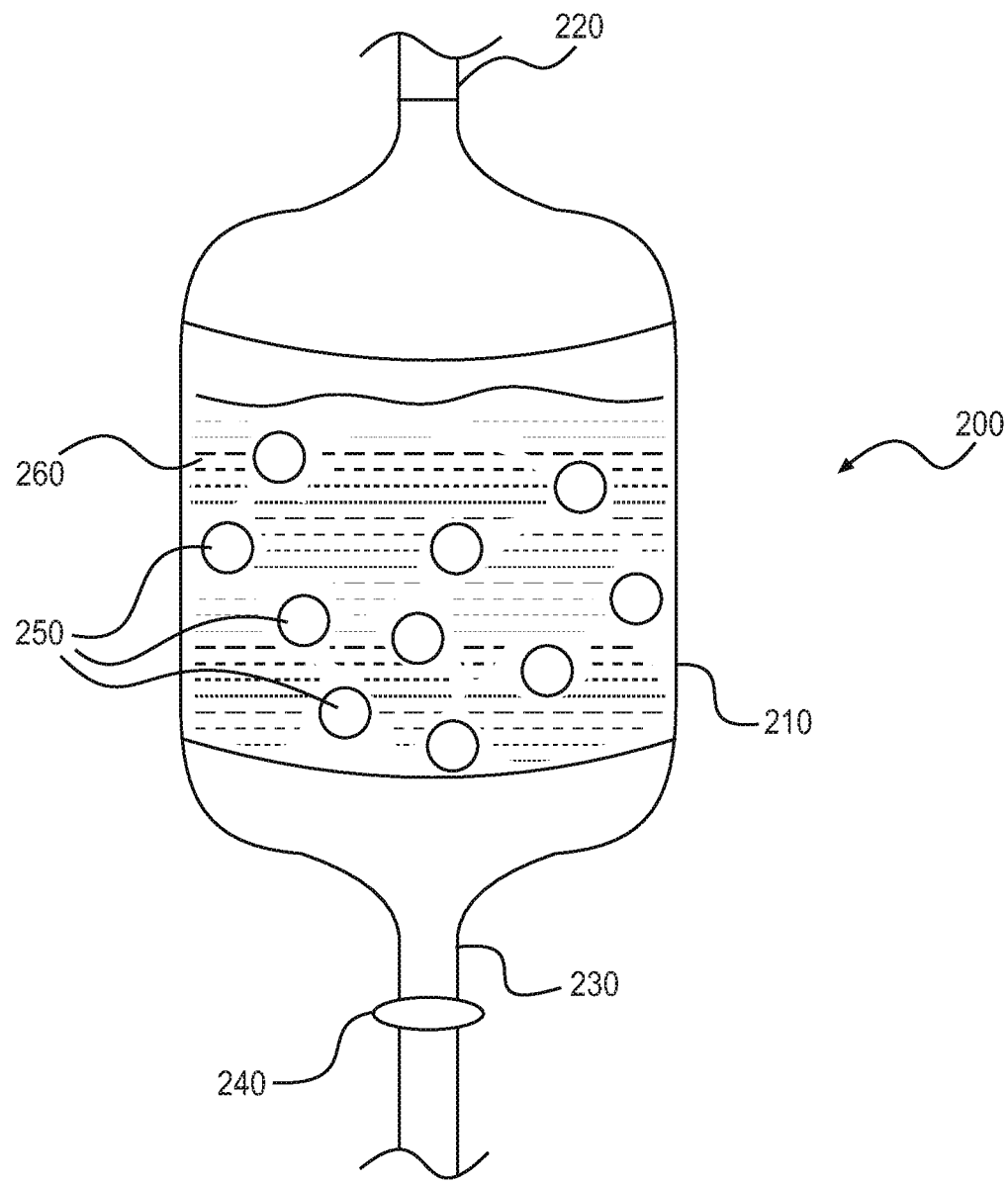
FIG. 2A illustrates a device for treating formula, according to certain embodiments.
Figure 2B:
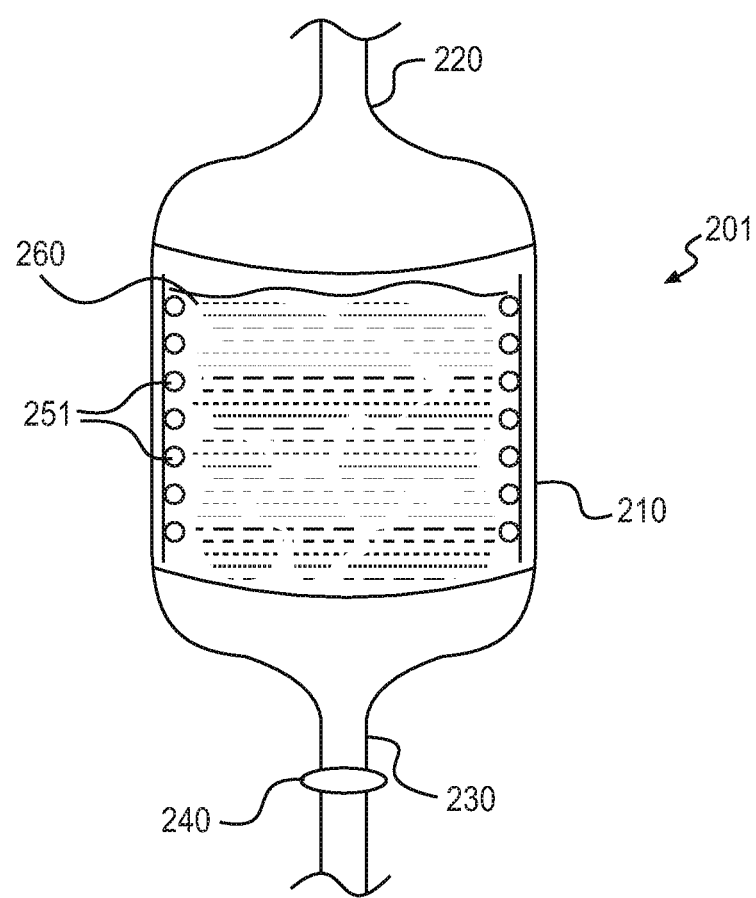
FIG. 2B illustrates a device for treating formula, according to certain embodiments.
Figure 2C:
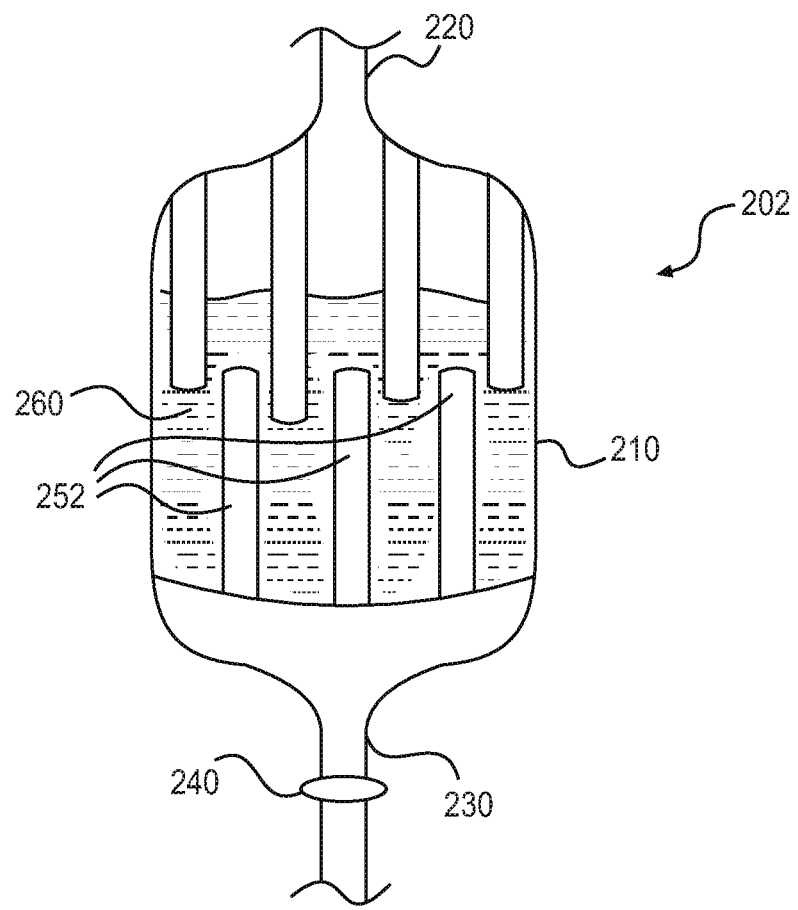
FIG. 2C illustrates a device for treating formula, according to certain embodiments.

FIGS. 2A-2C show one configuration for the container 210, along with certain embodiments for immobilizing lipases within the container 210. As noted, the container 210 can include a variety of different materials, sizes and shapes. In addition, the container 210 can include one or more access ports 220, 230 for controlling flow of formula 260 into and out of the container.

Lipases can be immobilized within the container 210 in a variety of ways. For example, lipases can be immobilized or contained within structures 250, 252 located inside the container 210 (FIGS. 2A and 2C). Additionally, or alternatively, lipases 251 can be immobilized on or contained within the wall of the container 210 (FIG. 2B). Accordingly, as formula 260 is placed inside the container, the formula 260 comes into contact with the lipases to produce the desired enzymatic effects.

Figure 4A:
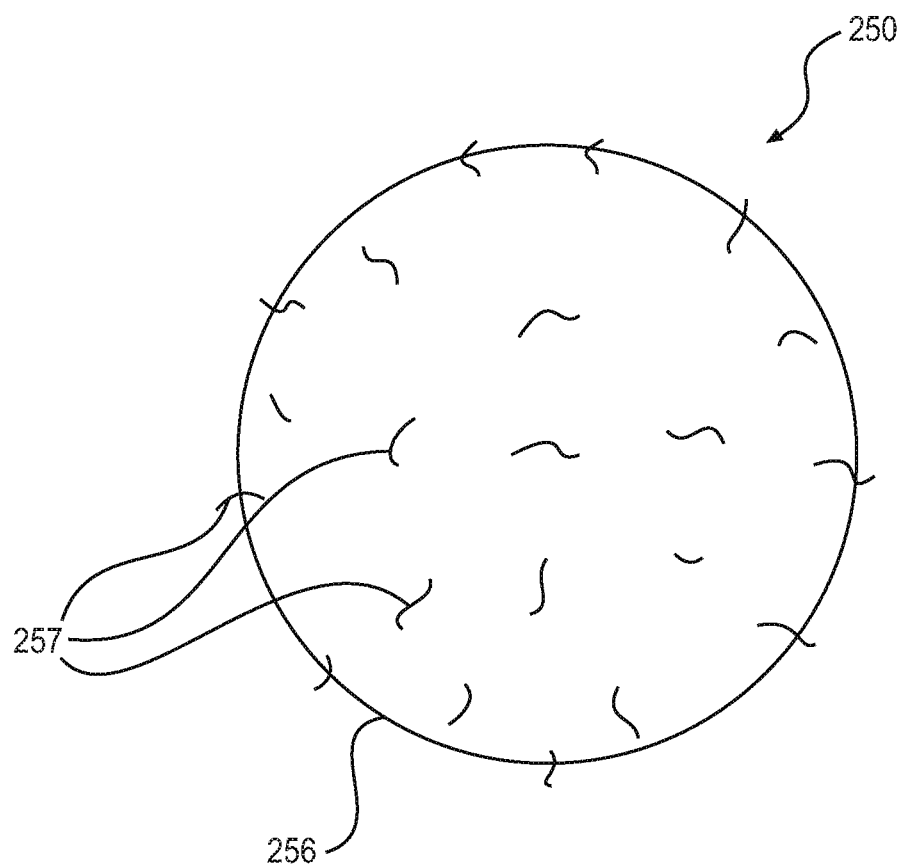
FIG. 4A illustrates a device for treating formula, according to certain embodiments.

As noted, lipases can be immobilized within the container by binding the lipases to structures 250, 252 within the container and/or to walls 251 of the container. The structures within the container can have a variety of configurations. For example, in certain embodiments, the structures can include beads, balls, or any other structure that may themselves be mobile within the container such that the structures flow within the formula. For example, as shown in FIG. 4A, the structures 250 can include beads or balls having a surface wall 256 to which lipases 257 can be bond. Further, it will be understood that the structures 250, 252 can have a variety of different shapes or configurations (e.g., cuboid, ovoid, rod-like).

The structures 250, 252 and/or configuration of the wall of container 210 can be configured to provide a desired surface area such that formula is able to come in contact with a sufficient amount of lipase during an acceptable time period. For example, the structures 250, 252 can include numerous beads 250 (FIG. 2A) or rod-like structures 252 (FIG. 2C) to provide a high surface area for binding a sufficient amount of lipase. Alternatively, if longer time periods are available to incubate the formula with the lipases before consumption and/or lipases with high enzymatic activity are used, smaller amounts of lipase may be suitable.

In various embodiments, the structures 250, 252 and/or container are constructed such that, as formula 260 is removed from the container for consumption or storage, the lipase is not kept within the formula 260. For example, the beads 250 or rod-like structures can be sized such that they will not pass through a relatively small access port 230. Alternatively, or additionally, the structures can be attached to the container wall and/or the container can include a screen or filter that is sized to prevent movement of the structures with the formula 260. Further, the structures 250, 252 can have other properties that facilitate their separation from formula. For example, the structures 250 can be formed of magnetic beads that can be removed by binding to a magnetic filter.

Figure 4B:
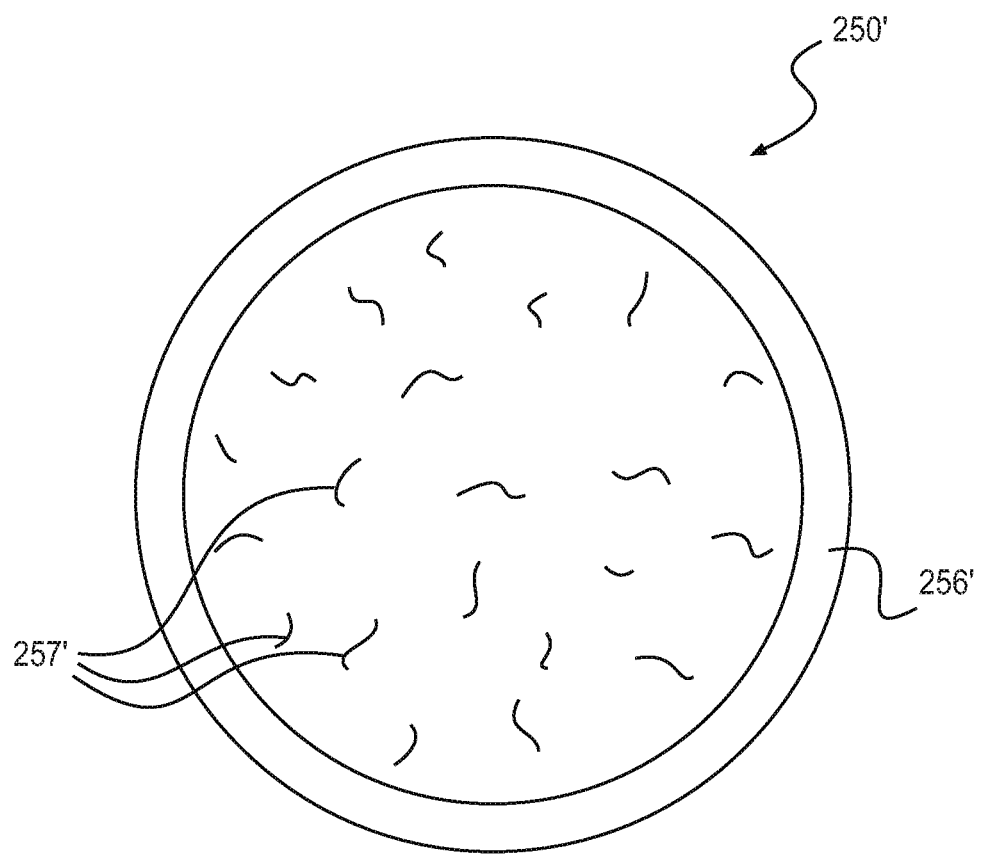
FIG. 4B illustrates a device for treating formula, according to certain embodiments.

In some embodiments, rather than immobilizing lipases by attachment to structures within the container 210 and/or container wall, the lipases 257' are contained within the structures 250, 252 and/or the container wall 251. FIG. 4B illustrates one such an embodiment. As shown, the structures 250' can include beads or other shapes having a wall 256'. The wall may be formed of a semi-permeable materials that allows ingress and egress of formula 260 but not lipases 257'. Such encapsulation may similarly be used for other structures (e.g., 252) and/or for the container wall such that the surface of the wall has a semi-permeable material, within which lipases may be contained.

The container may similarly have surface configurations that provide for increased amounts of lipase, and/or increased contact of lipases with the formula 260. For example, the wall of the container may have ridges or other surface modifications to increase the surface area. Further, rather than including a single open space, the container may include variations in the flow path, e.g., a long winding path to allow prolonged or longer exposure to lipases and/or a collection of channels or tubes to which lipases are immobilized and through which formula may flow. See, e.g., FIG. 1, element 150 and FIG. 21, element 2101.

In certain embodiments, the container may be manufactured and prepackaged with lipases in any of the embodiments described herein. During use, the container may be opened, and formula may be placed into the container to contact the lipases for a sufficient time to produce the desired enzymatic effects. In other embodiments, structures such as beads 250 or rod-like structures have lipases immobilized to their surfaces or contained/encapsulated within can be packaged and distributed, and those structures can be placed into a separate container containing formula. In some embodiments, it may be beneficial to shake or agitate the container comprising immobilized lipase and formula for a period of time.

As noted, formula 260 can be placed into the container 210 via various access ports. For example, the container can include a top access port 220 and/or a bottom access port 230. The ports 220, 230 can be used for ingress and egress of formula respectively. In addition, a single port can be used, or multiple ports may be used. The ports can comprise a structure configured to engage other devices that may be used for feeding or transfer of fluids. For example, the ports can include a connector such as a luer-lock connection, threads, and/or a conduit or tube that can engage a nasogastric tube. In addition, the ports can be configured to engage a baby bottle, baby bottle nipple, or any other structure to facilitate transfer of fluid to another container or to assist in feeding. Further, one or both ports 220, 230 can include a valve 140 (FIG. 1), 240 (FIG. 2A) or other fluid flow control mechanism.

Figure 3A:
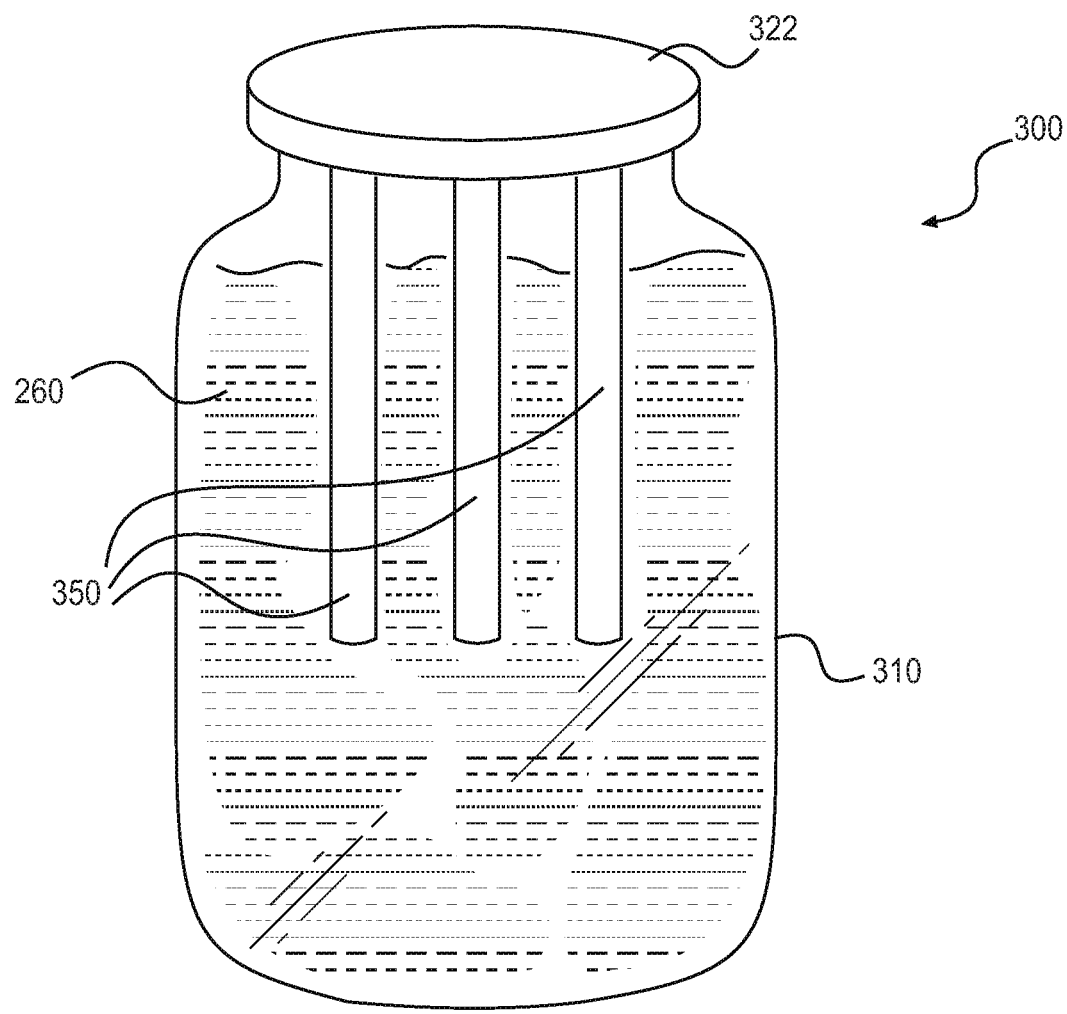
FIG. 3A illustrates a device for treating formula, according to certain embodiments.
Figure 3B:
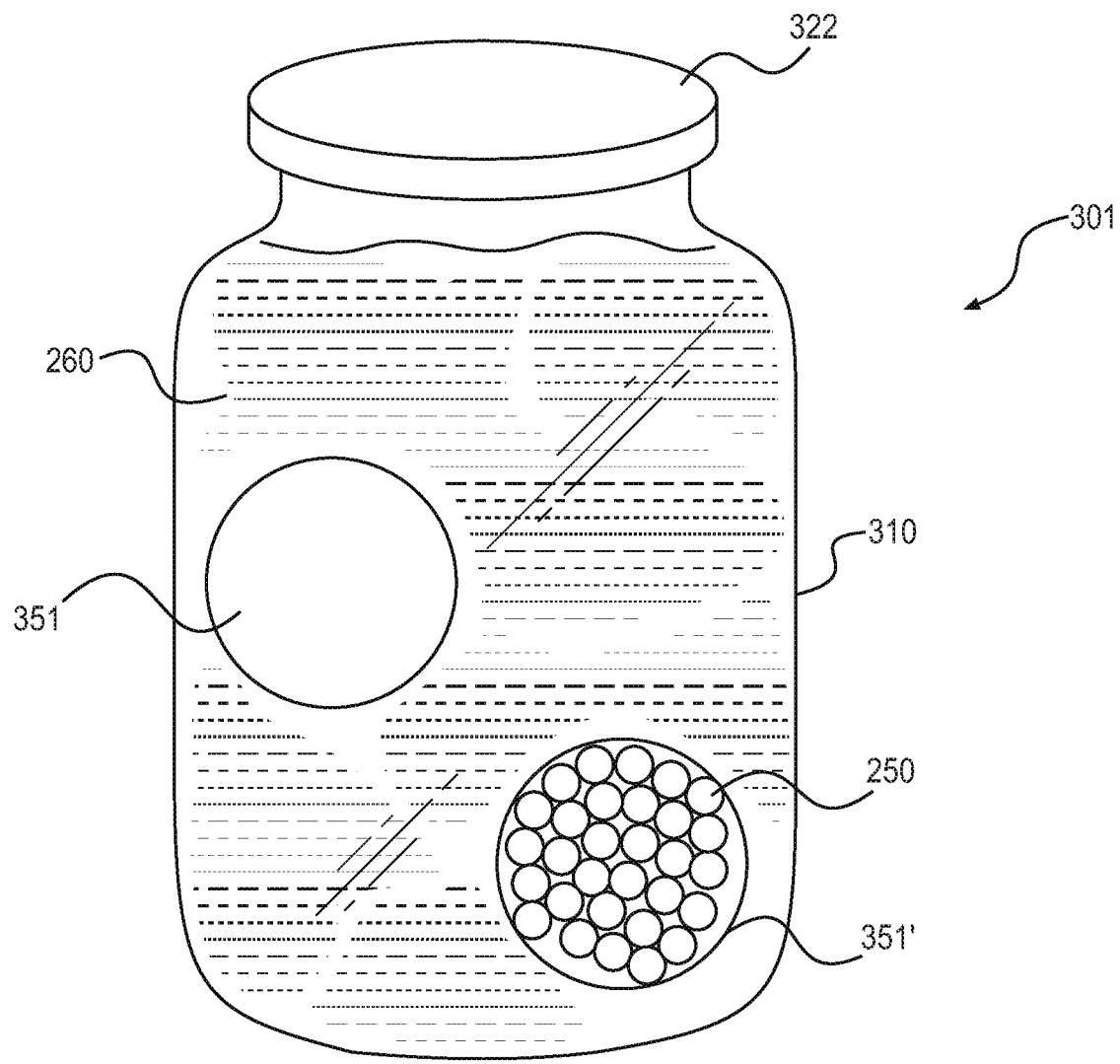
FIG. 3B illustrates a device for treating formula, according to certain embodiments.
Figure 3C:
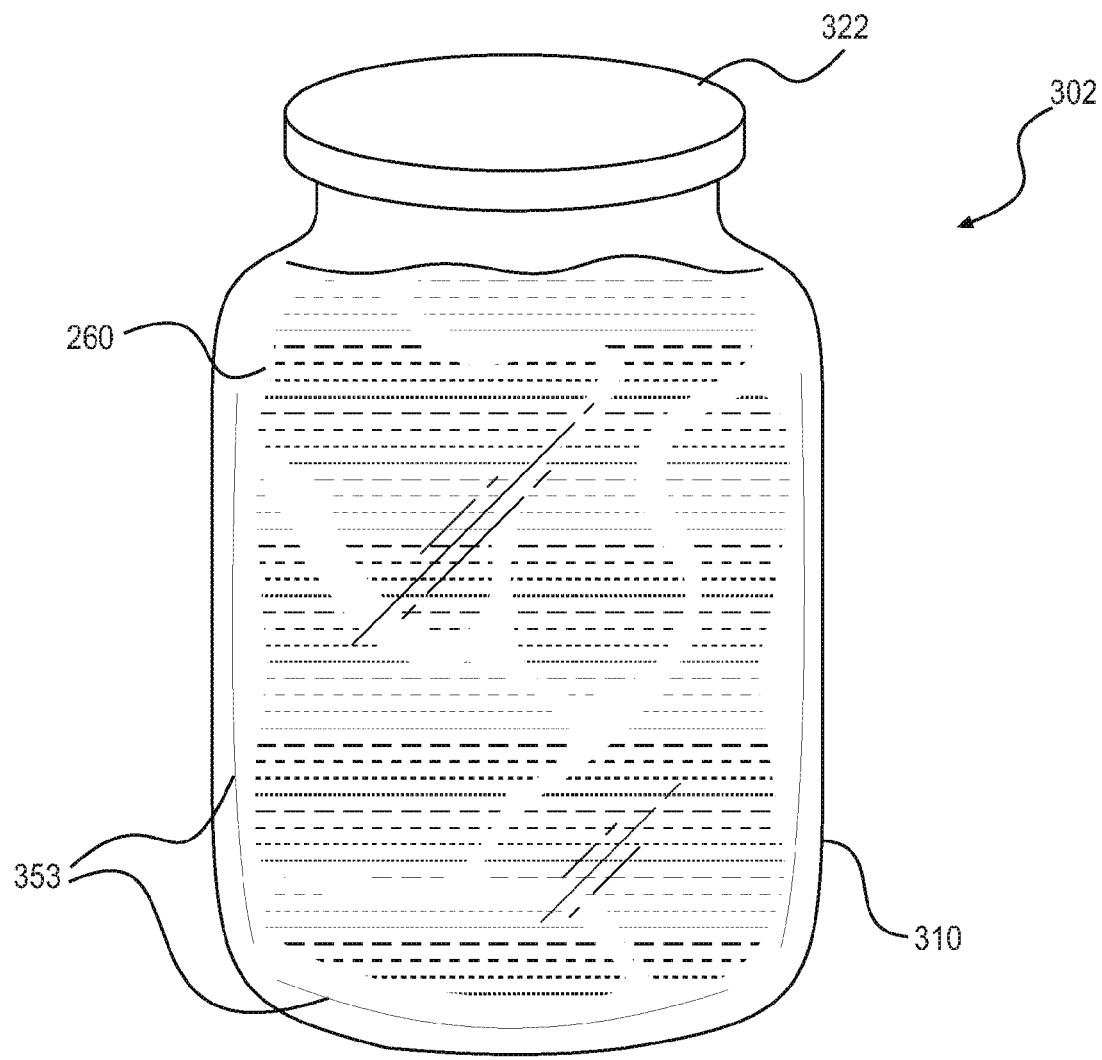
FIG. 3C illustrates a device for treating formula, according to certain embodiments.

FIGS. 3A-3C illustrate devices of the present disclosure, according to certain embodiments. As shown, the devices 300-302 include a container 310 for receiving formula 260. In addition, the container 310 can include a cap 322 or other closure device, such as a threaded top for a jar or bottle. Similar to the embodiments shown in FIGS. 2A-2C, the devices can include structures 350, 351, 351', and 353 that include lipases immobilized to their surfaces and/or encapsulated therein.

The embodiments of FIGS. 3A-3C can provide for more rapid separation of formula from the structures containing lipases. For example, as shown in FIG. 3A, the rod-like structures 350 can contain lipases, and after enzymatic treatment of formula, the cap 322 can be removed to simultaneously remove the structures 350 and lipases. Further, the cap 322 can be replaced with another cap, bottle nipple, or other fluid connection. Similarly, structures having other configurations, like the balls or beads 351, 351' (FIG. 3B), can be sized for easy removal from the formula 260. For example, as shown, beads 351, 351' are sized such that they can be easily removed manually or by filtration. Further, the container 310 can provide lipases that are immobilized to or contained within its inner surface 353, and after enzymatic treatment, formula 260 can be transferred to another container, or consumed by replacing the cap 322 with a bottle nipple or other connection to a feeding system.

Alternatively, or additionally, the structures 350, 351, 351' can have a permeable outer wall with additional components providing immobilized lipases contained therein. For example, structure 351' (FIG. 3B), illustrates one embodiment wherein the structure 351' has a permeable outer wall enclosing numbers beads 250. The outer wall can include a mesh or other configuration that allows for easy movement of formula into and out of the structure 351' to provide contact with the beads 250. Further, the beads can provide lipases, which can be immobilized to their surfaces or encapsulated therein, as described in various embodiments above.

As noted above, the structures containing lipases can be manufactured and distributed as prepackaged components along with the container 310. Alternatively, or additionally, the structures can be packaged and distributed separately from the container. For example, a cap 322 containing rod-like structures 350 or beads 351, 351', or otherwise having lipase contained therein or immobilized to it, can be manufactured and distributed. The cap may be configured for connection with standard baby bottles, water bottles, or other container or device that may contain formula.

Figure 5A:
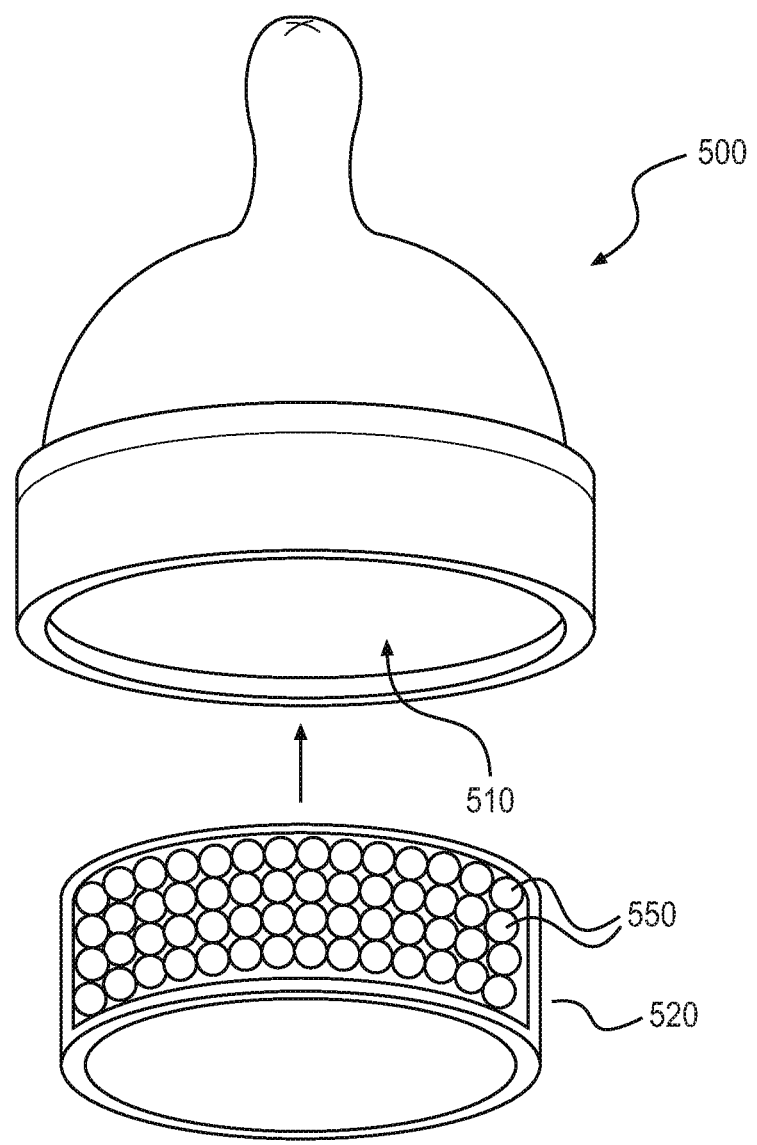
FIG. 5A illustrates a device for treating formula, according to certain embodiments.

In other embodiments, lipases may be provided such that the lipases contact formula as the formula is placed into a container and/or during feeding or removal from a container. For example, FIG. 5A illustrates one device 500, according to exemplary embodiments. The device 500 can include a standard bottle nipple, and lipases can be immobilized to an inner surface 510 of the nipple rim or nipple itself. As such, formula will come into contact with the lipases during normal use. Similarly, lipases can be contained in or on other structures that may be used for feeding, such as a fluid tube of a nasogastric feeding device.

Figure 5B:
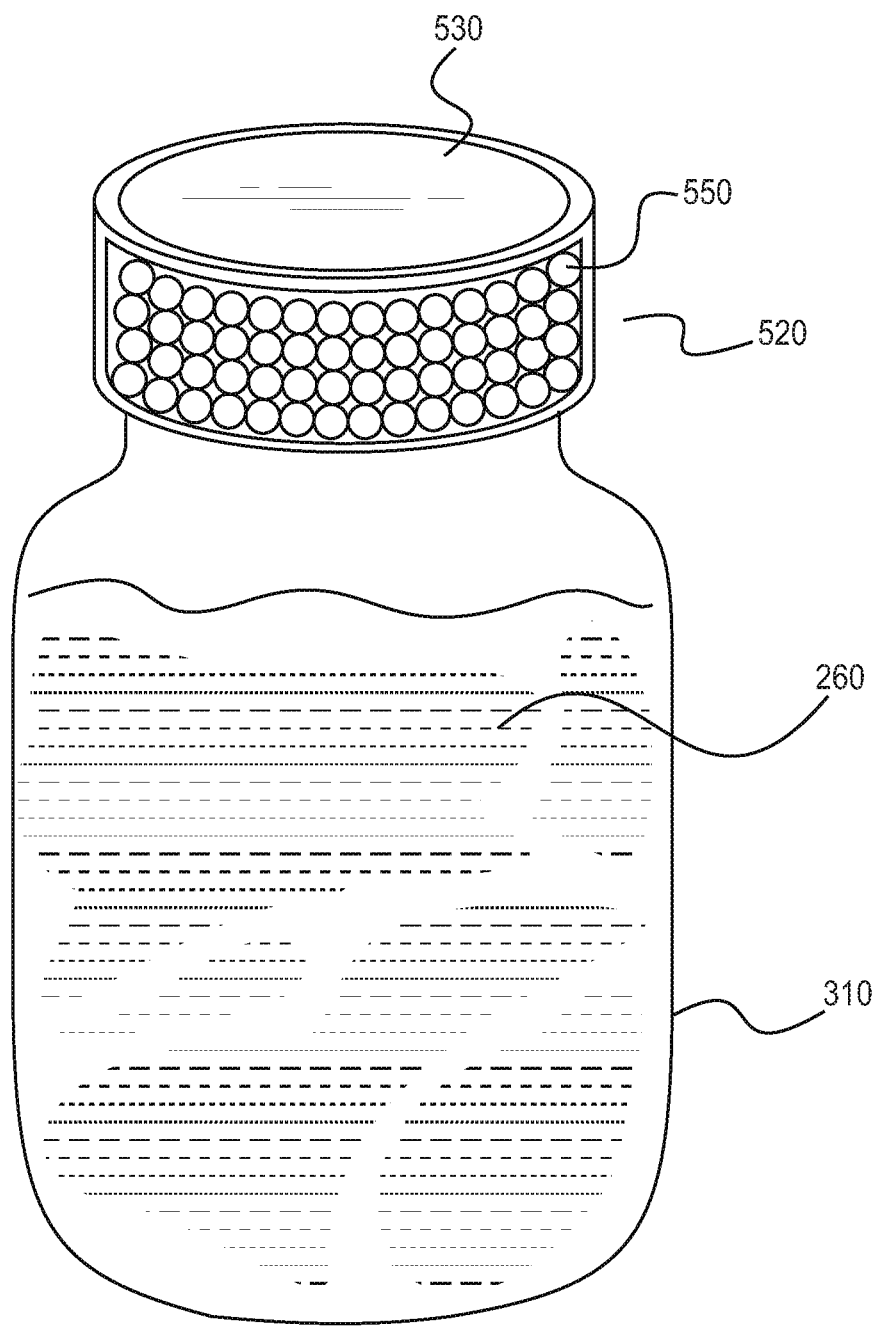
FIG. 5B illustrates a device for treating formula, according to certain embodiments.

Alternatively, the lipases can be provided in a separate element configured to allow contact of formula with the lipases during normal fluid flow. For example, in one embodiment, the lipases can be contained within a housing 520 configured for engagement with a bottle closure such as a nipple (FIG. 5A) or a bottle cap/top (FIG. 5B). The housing 520 can include a permeable walls that allows formula to flow through its volume and contact lipases provided therein.

The lipases contained within the housing 520 can be provided in various forms. For example, in some embodiments, the lipases are immobilized on beads 550 within the housing 520 by bonding or encapsulation, as described previously. Further, the housing 520 can include an open mesh or other configuration that allows formula to flow through it. For example, with the bottle configuration shown in FIG. 5A, an open mesh or flow path through housing 520 will allow formula to contact lipases as the formula exits a bottle during feeding. Alternatively, as shown in FIG. 5B, formula can be poured into or out of the top 530 of the housing to allow contact of formula with lipases during filling or emptying of the container 310. The top 530 and/or any other portion of the housing 520 can be formed of a variety of materials. For example, the housing 520 can be formed of a membrane that allows controlled fluid flow. Further, the top 530 may be formed of a semi-permeable membrane that allows flow of liquid (formula) therethrough, but does not allow passage of lipases. Accordingly, the membrane forming the top 530 can serve to immobilize the lipases within the container 310 without otherwise binding or immobilizing the lipases within the container 310.

In various embodiments, the devices described above can include modifications to improve or otherwise control lipase activity. For example, the containers 110, 210, 310 can include stirring systems to allow continuous movement of formula during an incubation period, thereby allowing the lipases to come into contact with fatty acids found throughout the fluid volume. Further, the devices can include systems to control temperature to improve or control lipase activity.

Certain embodiments of the invention provide a container containing nutritional formula and a lipase. In some embodiments, the lipase is in contact with the nutritional formula in the container. In other embodiments, the lipase and the nutritional formula are not in contact in the container. In some embodiments, the nutritional formula and the lipase are contained in separate compartments within the container. In some embodiments, the nutritional formula is in dry form. In some embodiments, the nutritional formula is in liquid form. In some embodiments, the lipase is brought into contact with the nutritional formula by releasing the lipase into the compartment containing the nutritional formula. In some embodiments, the lipase is brought into contact with the nutritional formula by transferring the lipase and the nutritional formula into another container (e.g., by emptying the lipase compartment and the nutritional formula compartment into the other container). In some embodiments, liquid is added to the other container before or after transferring the lipase and the nutritional formula into the other container.

The devices according to the present disclosure can have a number of different shapes and/or configurations. For example, FIGS. 9A-9C, 10A-10C, 11A-11C, 12, 13A-13B, 14, 15, 16, 17A-17B, 18, 19, 20, 21 illustrate various additional shapes and configurations. In each of the configurations described with respect to those figures, lipases may be immobilized using any of the methods described above (e.g., by immobilizing lipases on structures such as beads within a device, and/or by immobilizing lipases within or on a wall or other surface of a device). Further, the specific configuration may be selected to provide a variety of different features, such as surface area, volume, amount of lipases, and/or exposure time of materials to enzymes.

The devices illustrated in FIGS. 9A-9C, 10A-10C, 11A-11C, 12, 13A-13B, 14, 15, 16, 17A-17B, 18, 19, 20, 21 can be configured to allow contact of lipases in a variety of ways. For example, in various embodiments, a portion or all of the device can be inserted within a container that includes formula in order to allow contact between the formula and lipases. In other embodiments, the device is configured for in-line treatment of formula.

Figure 9A:
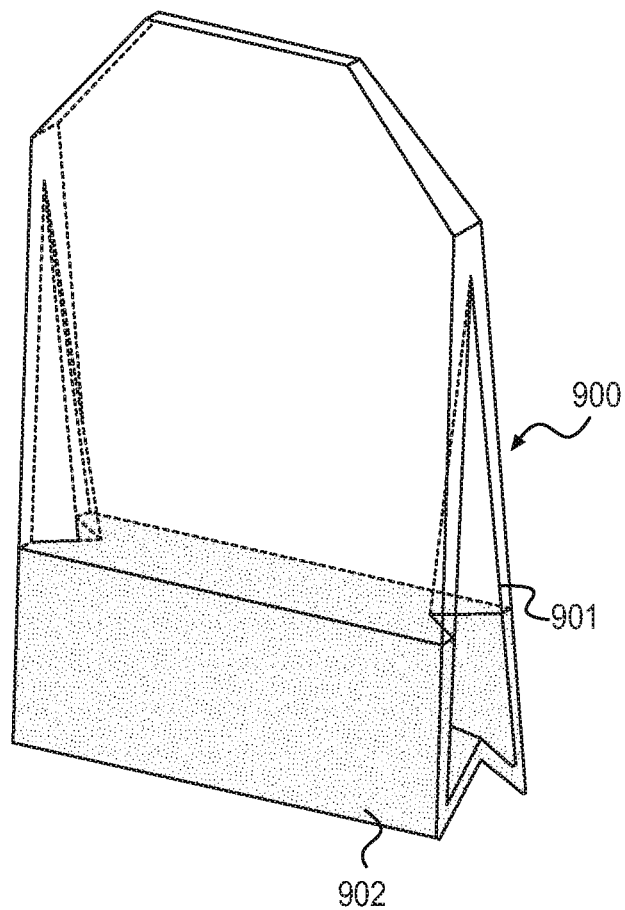
FIG. 9A illustrates a device for treating formula, according to certain embodiments.
Figure 9C:
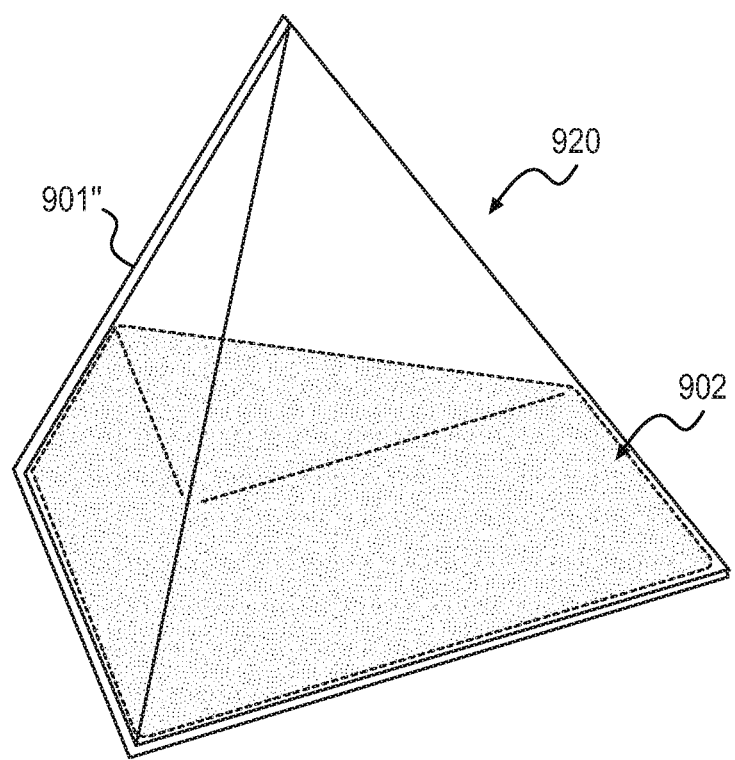
FIG. 9C illustrates a device for treating formula, according to certain embodiments.
Figure 12:
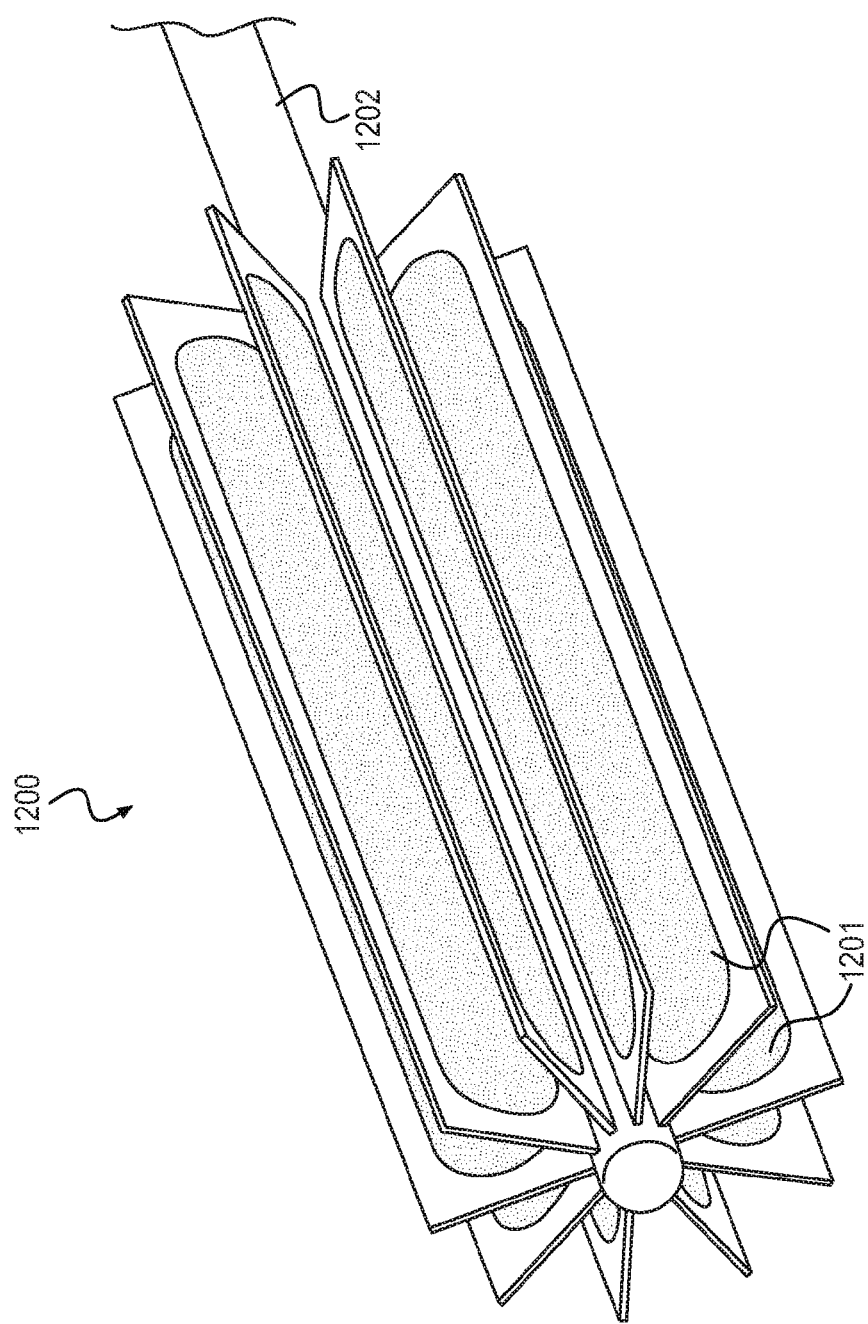
FIG. 12 illustrates a device for treating formula, according to certain embodiments.
Figure 13A:
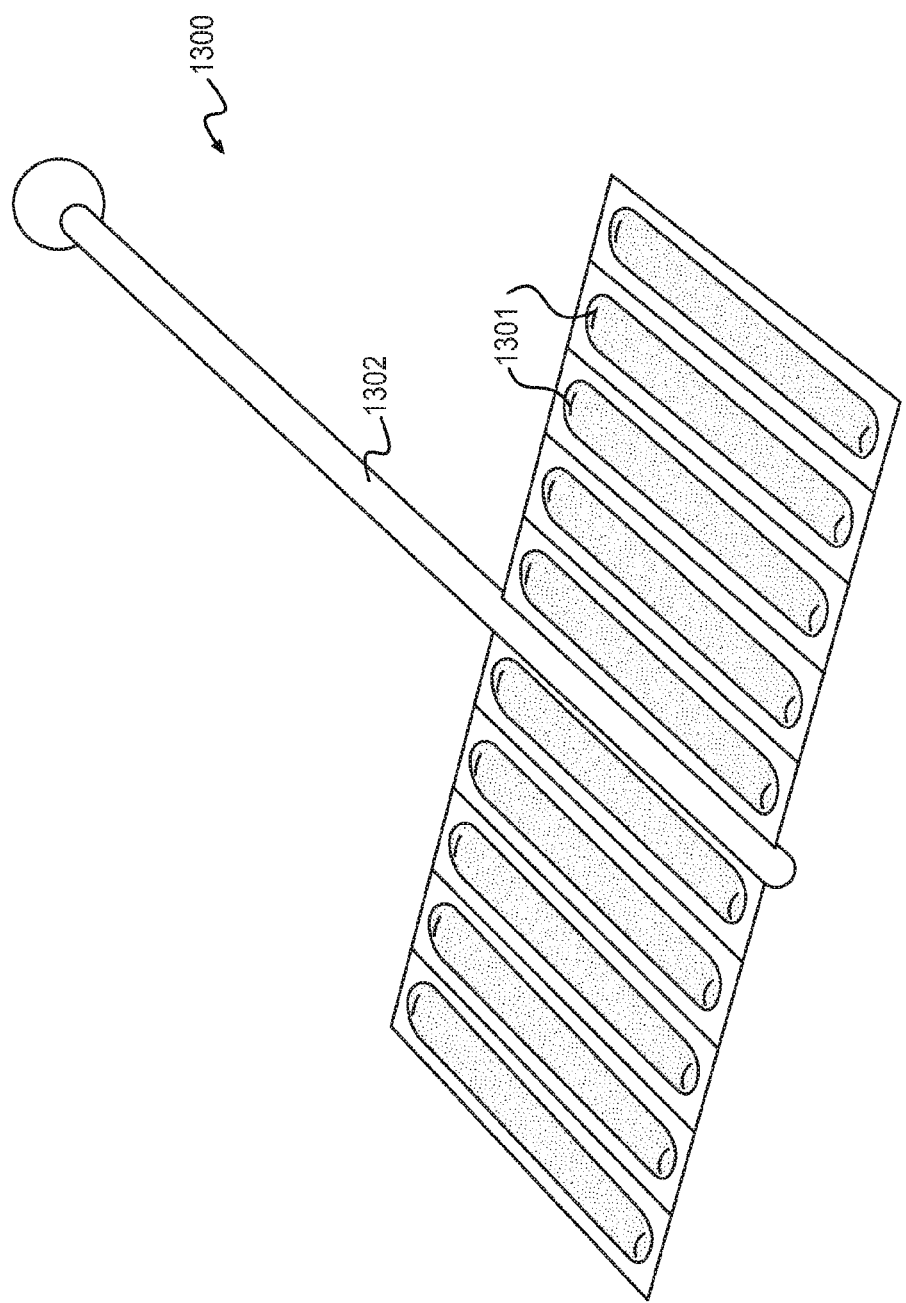
FIG. 13A illustrates a device for treating formula, according to certain embodiments.
Figure 13B:
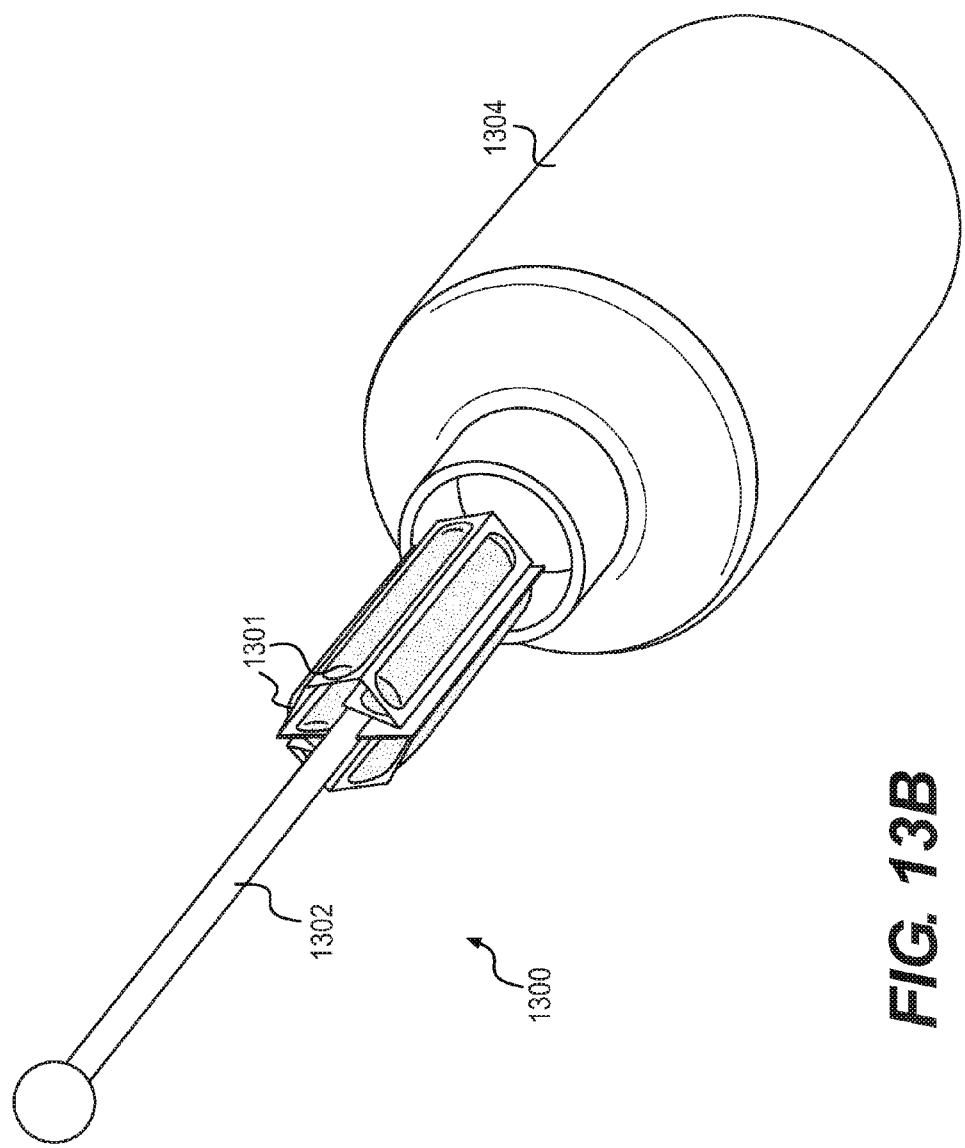
FIG. 13B illustrates a device for treating formula, according to certain embodiments.
Figure 14:
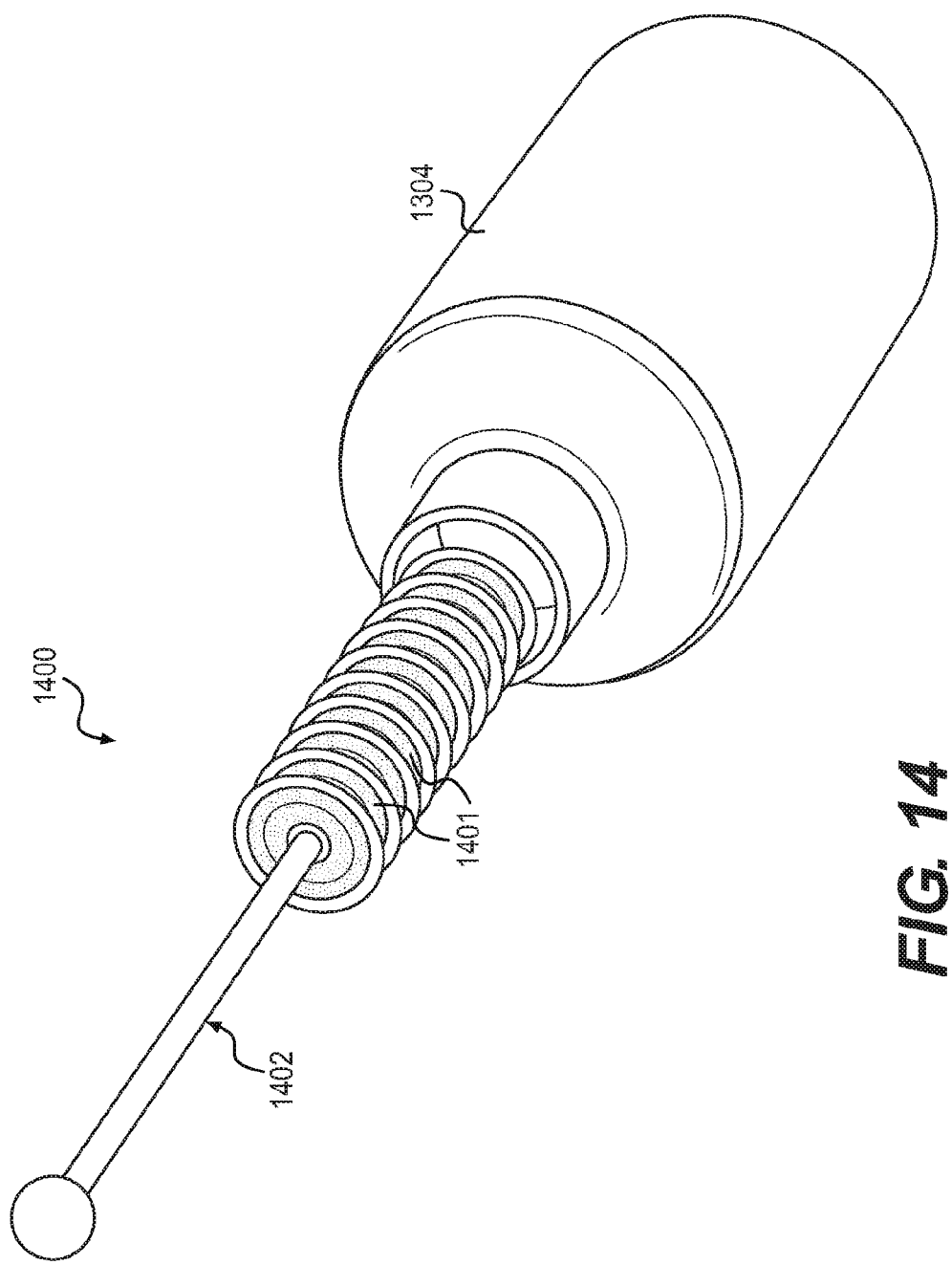
FIG. 14 illustrates a device for treating formula, according to certain embodiments.
Figure 15:
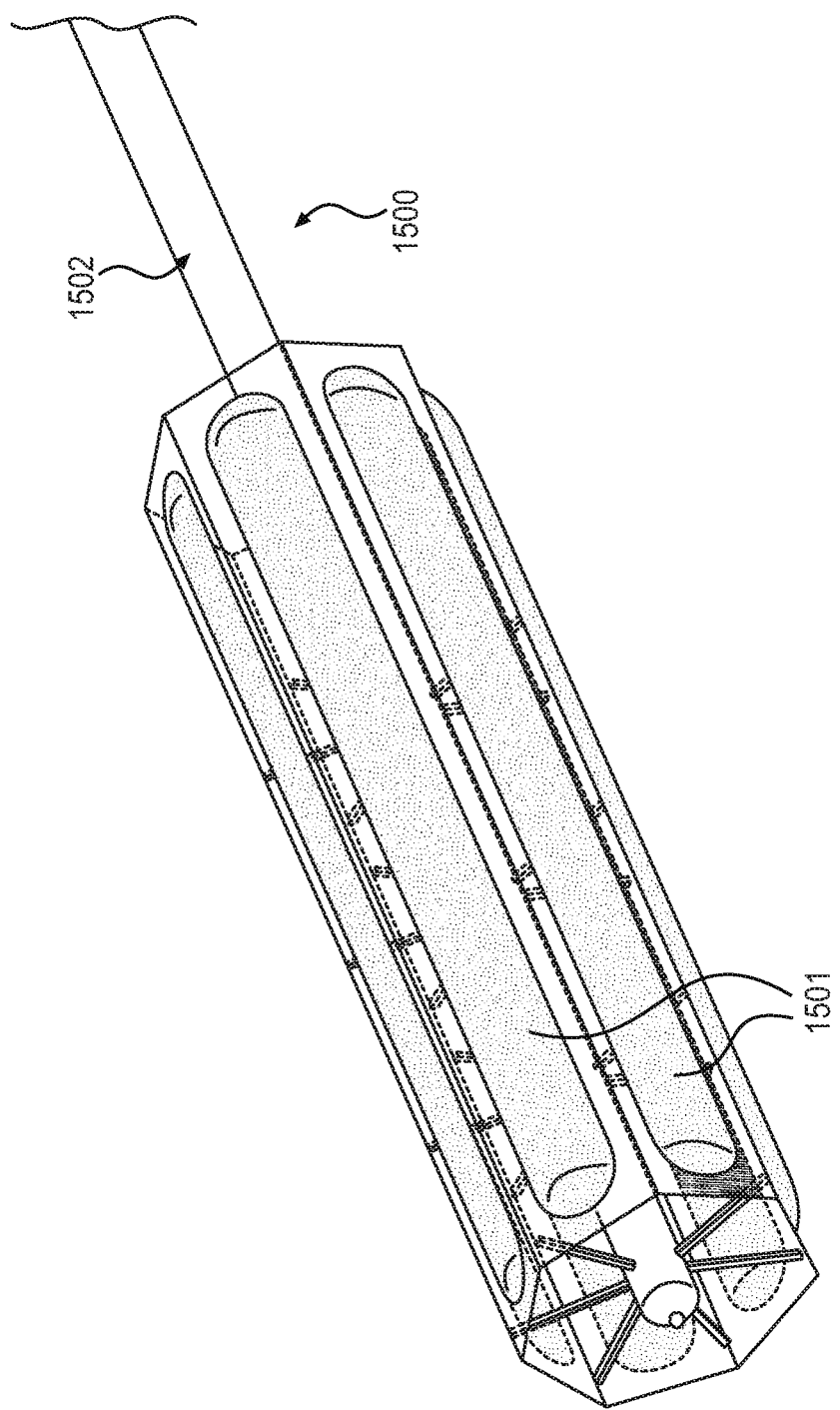
FIG. 15 illustrates a device for treating formula, according to certain embodiments.
Figure 16:
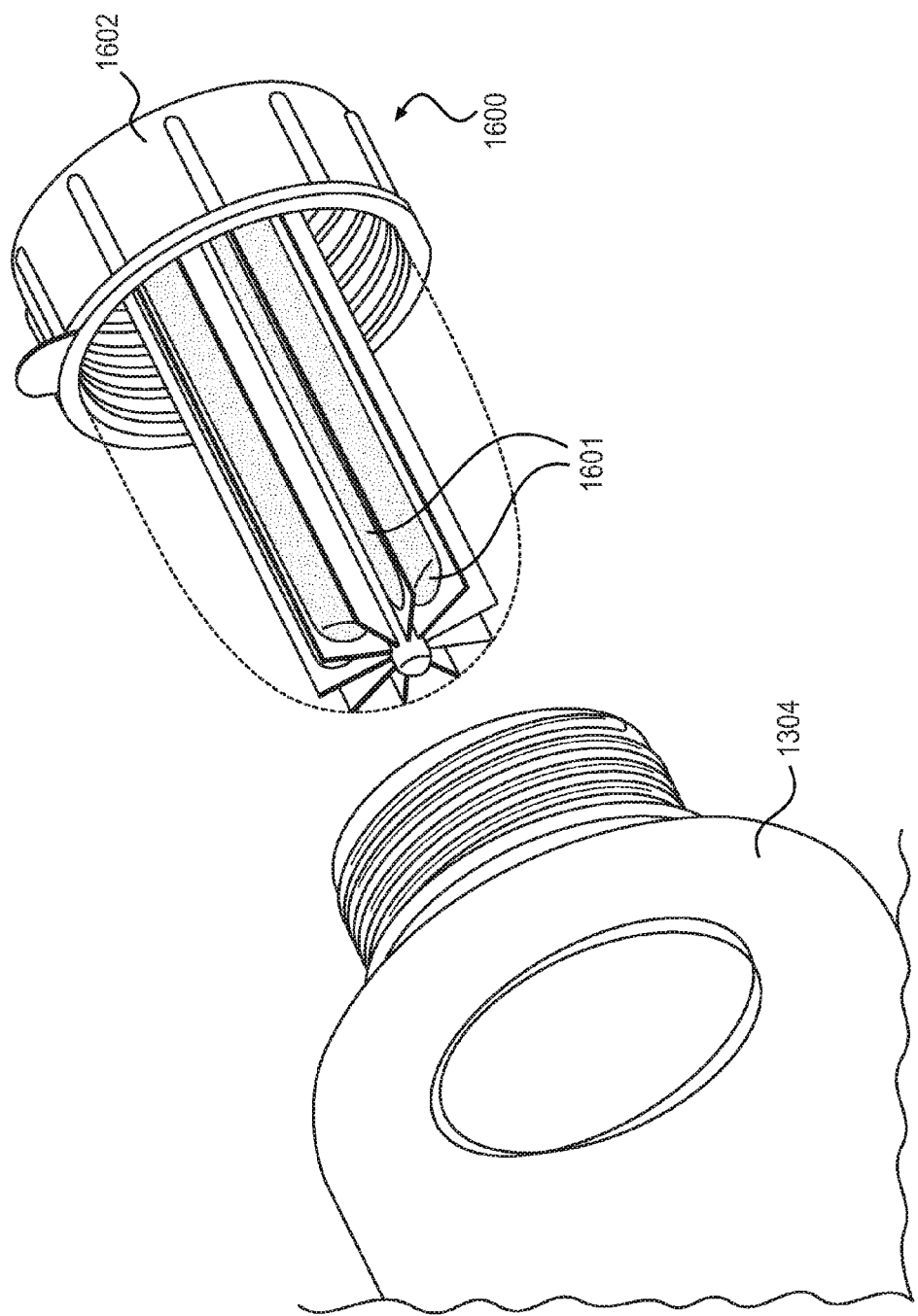
FIG. 16 illustrates a device for treating formula, according to certain embodiments.
Figure 17B:
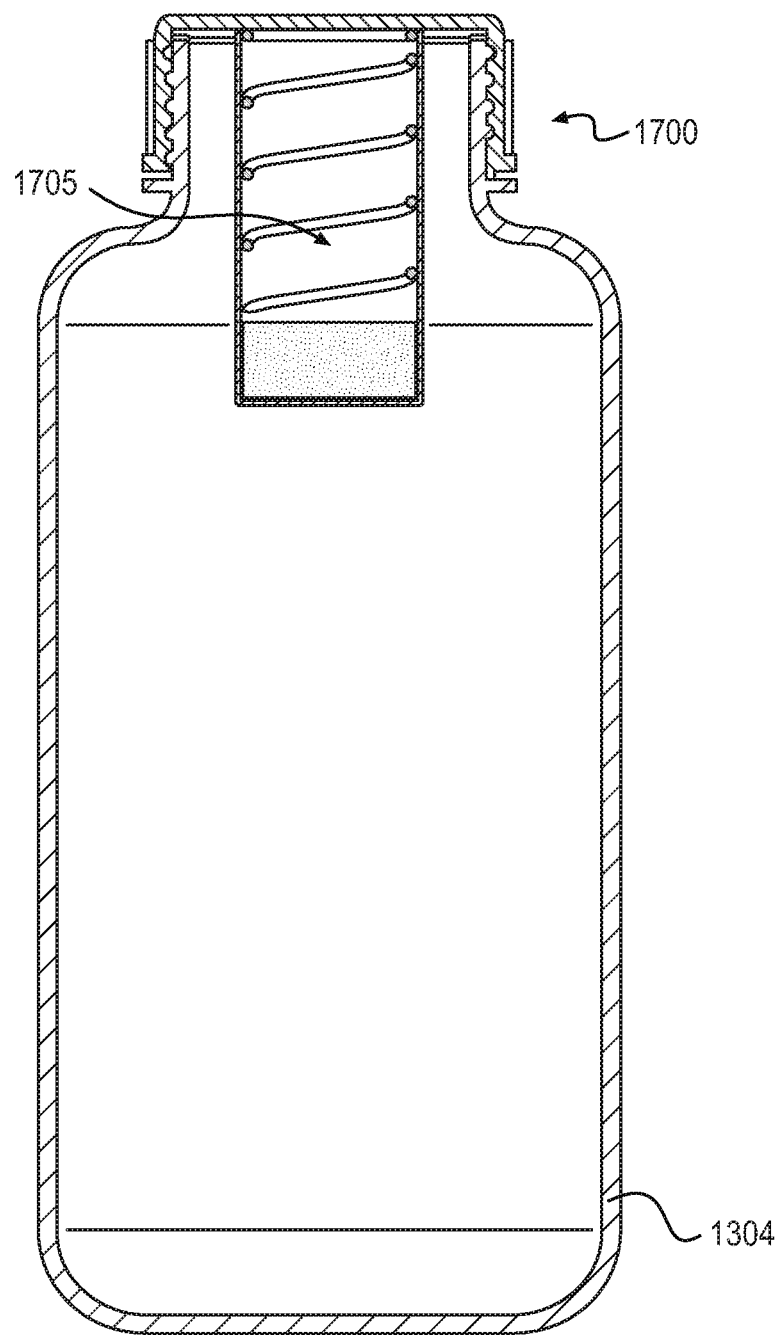
FIG. 17B illustrates a partial cut-away view of a device for treating formula, according to certain embodiments.
Figure 18:
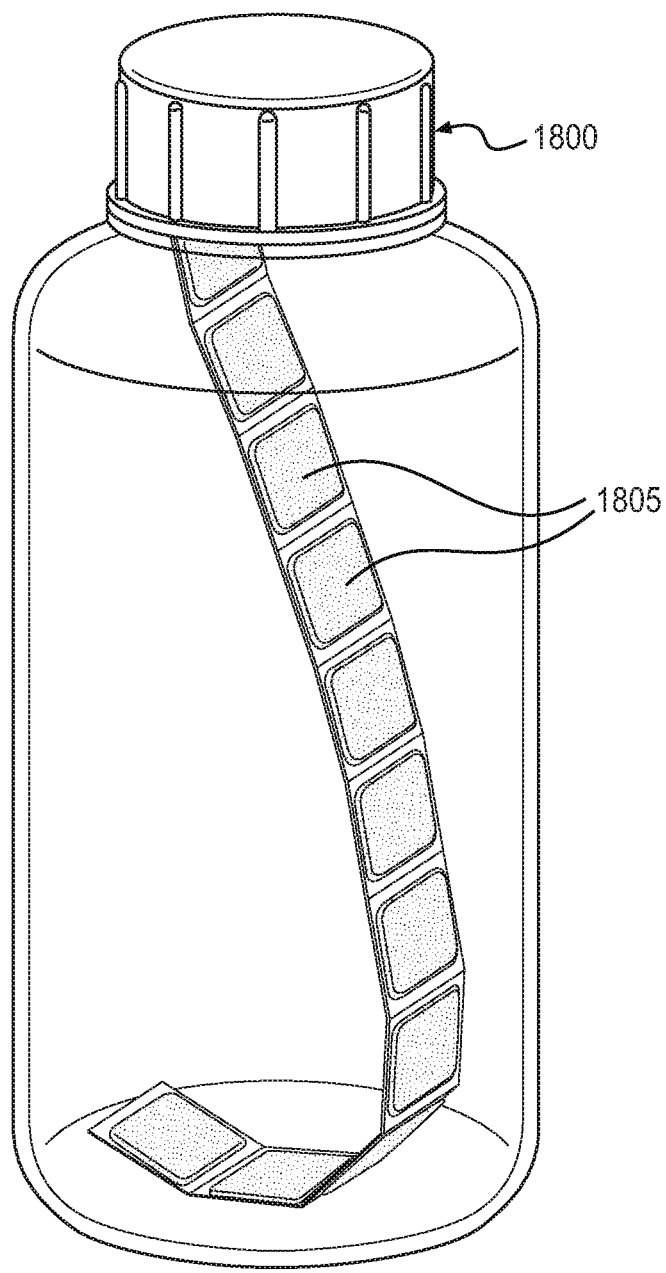
FIG. 18 illustrates a device for treating formula, according to certain embodiments.
Figure 19:
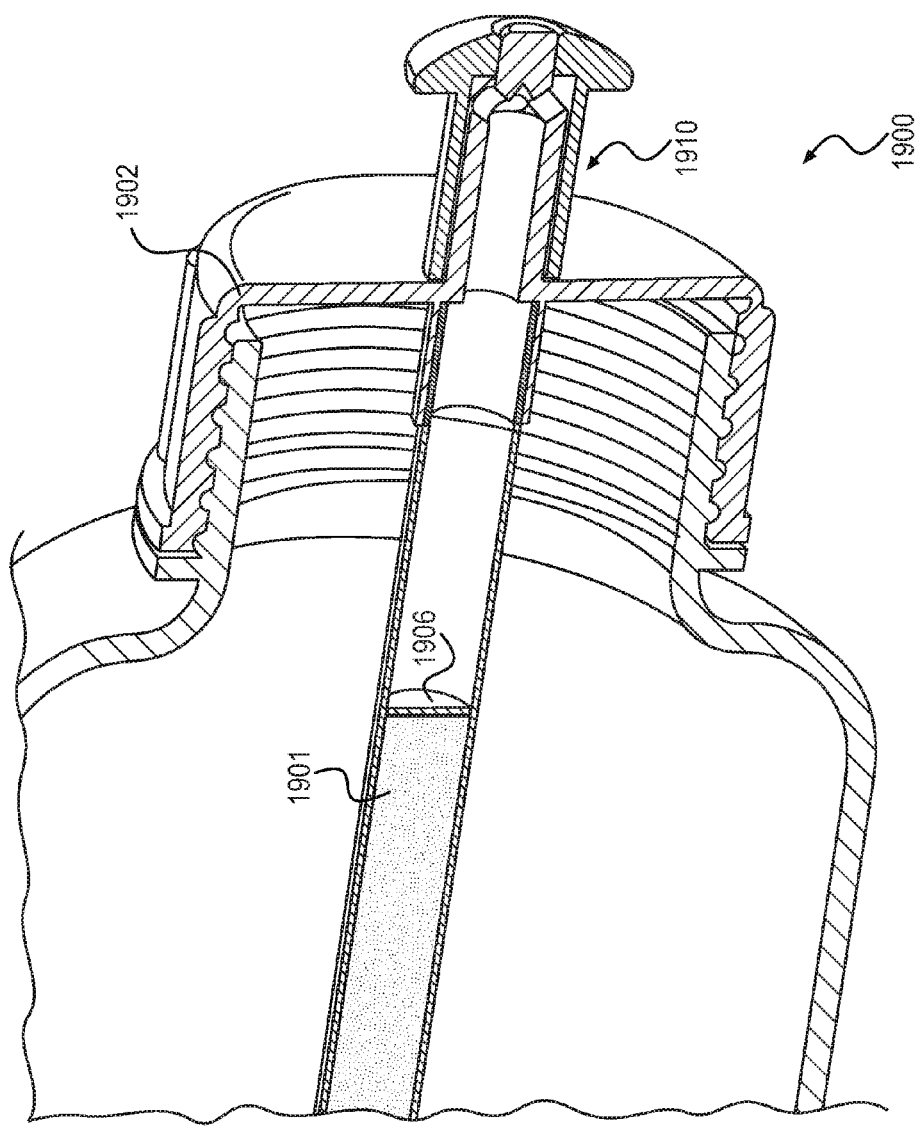
FIG. 19 illustrates a partial cut-away view of a device for treating formula, according to certain embodiments.
Figure 20:
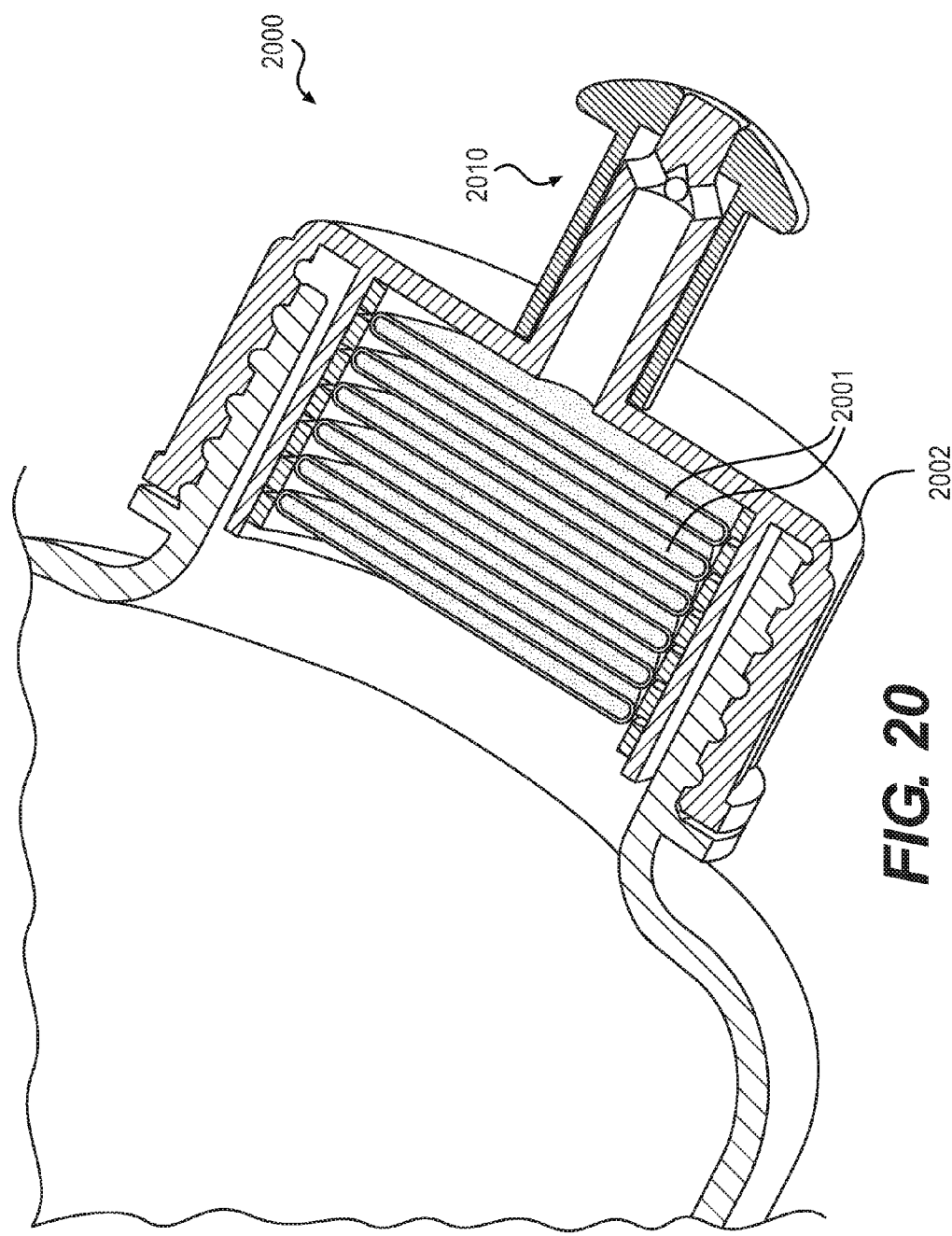
FIG. 20 illustrates a partial cut-away view of a device for treating formula, according to certain embodiments.

FIGS. 9A-9C illustrate various configurations for devices that may be placed within a container to treat formula. As shown, the device 900, 920 (FIGS. 9A and 9C) can have a variety of different shapes formed of an outer wall 901, 901" that encloses lipases. As indicated above, the lipases 902 can be immobilized in a variety of different ways, including by attachment to beads. Furthermore, the devices 910 (FIG. 9B) can include more than one pocket or opening 903 formed in one or more walls 901'. The specific configuration, number of pockets or openings, as well as amount of lipase and/or volume of the device may be varied depending on the intended use and/or to control the rate of lipase activity.

In certain embodiments, the device may be configured to allow a change in its size and or shape. For example, FIGS. 10A-10C illustrate a device 1000, which may be compressed, e.g., for storage in a container 1001 before use. When desired, the container 1001 can be opened, and the wall 1003 of the device can be expanded to produce a desired ratio of lipase volume 1002 to container volume. In some embodiments, the device 1000 includes a coil or spring 1004 to provide structural support and/or to help the device maintain a desired shape and/or volume.

In some embodiments, the device can include a rod-like extension to facilitate placement and removal of lipase within a volume of formula. For example, FIGS. 11A-11C, 12, 13A-13B, 14, and 15 illustrate various exemplary configurations for devices with a rod-like extension. As shown, the device 1100, 1100', 1100", 1200, 1300, 1400, 1500 can include either one or multiple pockets or openings 1101, 1201, 1301, 1401, 1501 positioned in various configurations near a distal region of the rod-like extension 1102, 1202, 1302, 1402, 1502. In some embodiments, as shown for example, in FIGS. 13A-13B, the orientation of the pockets or openings 1301 can be adjustable, e.g., to allow insertion within a narrow opening during use and/or to minimize storage space.

In various embodiments, lipase may be attached to a portion of a cap or closure for a bottle or jar, such that when the cap or closure is placed on the bottle or jar, the lipase may contact fluids contained within the bottle or jar. For example, any of the devices shown herein may be attached to a surface of a cap or closure to allow contact with formula container in a bottle or jar. Various configurations of devices 1600, 1700, 1800, 1900, 2000 including lipase attached to a cap or closure 1602, 1702, 1802, 1902, 2002 are illustrated in FIGS. 16, 17A-17B, 18, 19, and 20. As shown, the lipases can be contained within pockets or openings 1601, 1705, 1805, 1901, 2001 having a variety of shapes or configurations. Further, in some embodiments, the cap or closure 1902, 2002 can include an opening 1910, 2010 for inserting or removing fluid from a container, and such openings 1910, 2010 can include a connector for a fluid tube, e.g., a luer-type connector.

Figure 21:
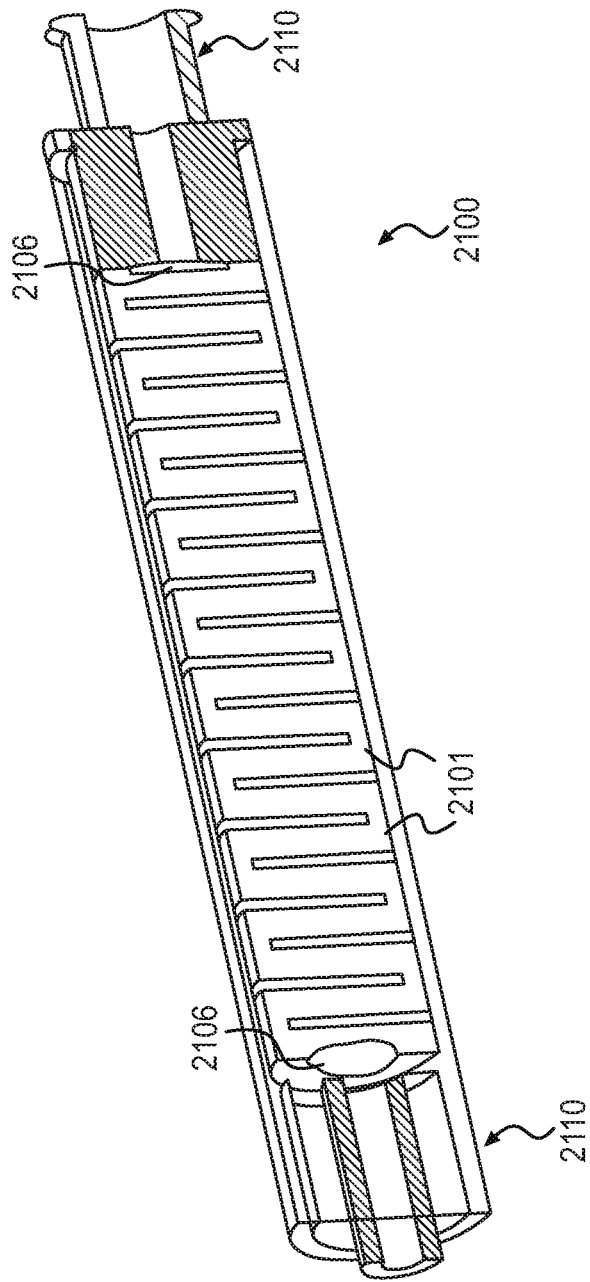
FIG. 21 illustrates a partial cut-away view of a device for treating formula, according to certain embodiments.

In some embodiments, it may be desirable to treat formula as the formula flows through a tube (e.g., during feeding, as shown in FIG. 1, or during transfer from one container to another). FIG. 21 illustrates another device 2100 for in-line treatment of lipases. The device 2100 can include a pocket or opening 2101 containing lipases, which may be immobilized, as discussed above. Further, the pocket or opening 2101 may have a tortuous or curved path to allow for longer contact times between the lipases and formula. In addition, the device 2100 may include openings 2110 at both ends to allow connection to tubes or conduits for ingress and egress of formula.

In various embodiments, the devices may include a material that acts as a screen or mesh to prevent lipases from entering the formula to be ingested by a patient. For example, the devices shown in FIGS. 19 and 21 can include one or more meshes or screens 1906, 2106 to prevent lipases immobilized on beads or other structures from moving into formula to be ingested.

In some embodiments, lipases can be immobilized within or on a component of a container such that the lipases are not in contact with formula until further steps are taken. For example, in one embodiment, lipases may be contained within or on a portion of a cap or closure, and the cap or closure may include a mechanism for releasing immobilized lipases into the container. For example, lipases may be contained on or within beads or other structures (see, e.g., element 1805 in FIG. 18), that are further attached to or contained within the cap; and when desired, the lipases may be dropped into the container (e.g., by twisting the cap or removing a barrier/attachment mechanism). Similarly, lipases may be attached to or contained with a wall of the container or other structure and immobilized on beads or other materials, and the lipases can be allowed to contact formula only when desired (e.g., by releasing lipases into the container or removing a barrier over the lipases).

Figure 6B:
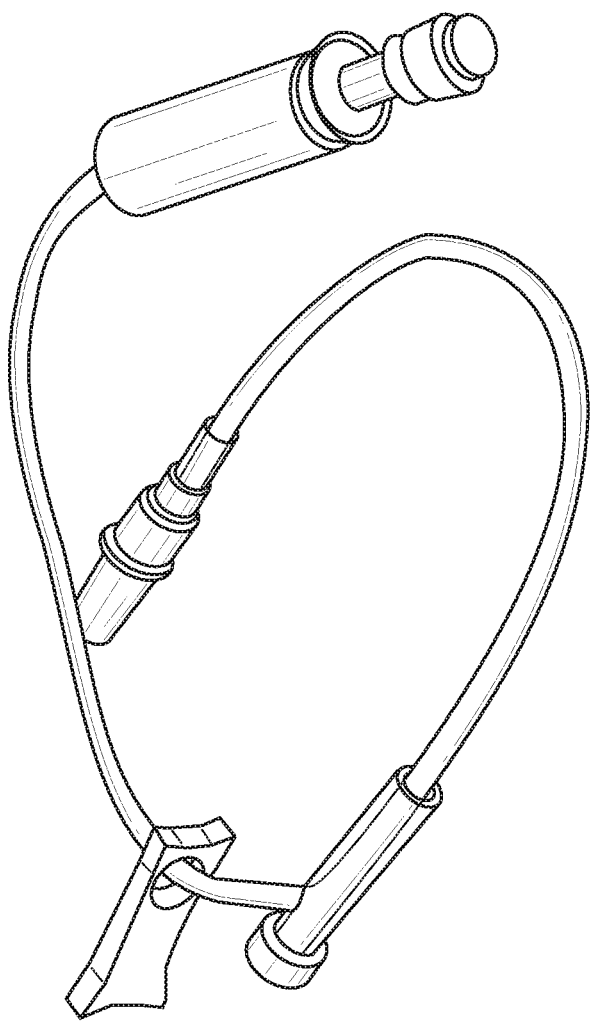
FIG. 6B illustrates a device for treating and administering nutritional formula according to certain embodiments.
Figure 6A:
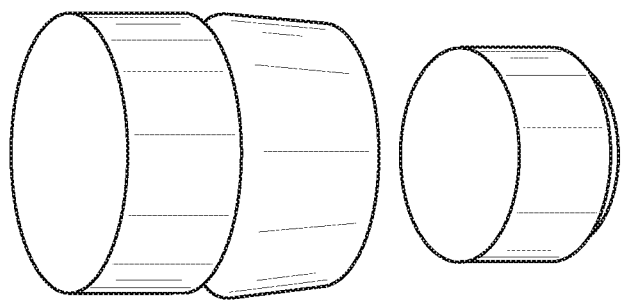
FIG. 6A is a photograph of a vial of *Rhizopus oryzae* lipase immobilized on polymer beads.
Figure 6D:
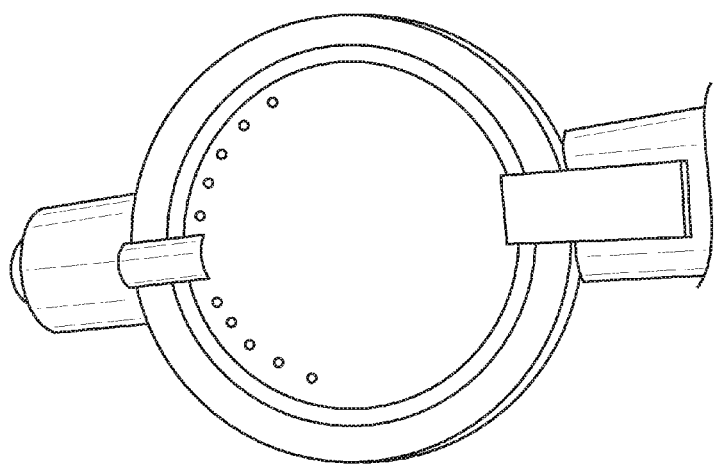
FIG. 6D illustrates a close up of the device depicted in FIG. 6C.
Figure 6C:
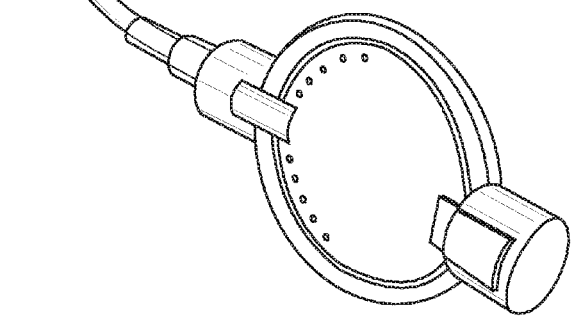
FIG. 6C illustrates a device for treating and administering nutritional formula according to certain embodiments.

FIG. 6A is a photograph of a vial containing *Rhizopus oryzae* lipase immobilized on polymer beads. The immobilized lipase is in dry granular form which may be added to the container or chamber of a device according to the invention, such as the device depicted in FIGS. 6B-D. The immobilized lipase may be trapped in the chamber of the device, while still allowing the flow of formula through and out of the chamber by simply providing a filter at the egress end of the chamber that contains pores sufficiently large to allow formula to pass but retains the immobilized lipase within the chamber. Alternatively, lipase may be immobilized by, e.g., coating the inner channels or chamber of the device so that the formula is exposed to the lipase as it passes through the chamber. The immobilized lipase in such a device may be used for continuous feeding for extended periods because of the increased stability and reusability of the lipase.

Nutritional Formulas

Certain embodiments of the invention provide nutritional formulas. In some embodiments, the nutritional formula is an infant formula. In some embodiments, the nutritional formula is a medical nutritional formula. In some embodiments, a nutritional formula is exposed to lipase prior to ingestion. In some embodiments, this exposure allows pre-hydrolysis of at least some lipids in the nutritional formula. Thus, in some embodiments, a nutritional formula is an "as-fed" formula, i.e., the liquid formula as composed just prior to ingestion by the subject, which differs in composition from the formula as sold by the manufacturer. The term "nutritional formula" does not encompass compositions existing within the body of a subject after ingestion.

In some embodiments, the nutritional formula comprises long-chain fatty acids. In some embodiments, the nutritional formula comprises one or more LC-PUFAs, such as DHA, ARA, and EPA. In some embodiments, the nutritional formula comprises DHA. In some embodiments, the nutritional formula comprises ARA. In some embodiments, the nutritional formula comprises DHA and ARA. In some embodiments, the nutritional formula comprises DHA, ARA, and EPA.

In some embodiments, more than 5% of the total long-chain fatty acids in the nutritional formula are in the form of monoglycerides and/or free fatty acids. In some embodiments, more than 5% of the total LC-PUFA in the nutritional formula is in the form of monoglycerides and/or free fatty acids. In some embodiments, more than 5% of the DHA is in the form of a monoglyceride and/or a free fatty acid. In some embodiments, more than 5% of the ARA is in the form of a monoglyceride and/or a free fatty acid. In some embodiments, more than 5% of the EPA is in the form of a monoglyceride and/or a free fatty acid.

In some embodiments, more than 10%, more than 15%, more than 20%, more than 30%, more than 40%, more than 50%, more than 60%, more than 70%, more than 80%, more than 85%, more than 90%, more than 95%, or 100% of the total long-chain fatty acids in the nutritional formula are in the form of monoglycerides and/or free fatty acids. In some embodiments, more than 10%, more than 15%, more than 20%, more than 30%, more than 40%, more than 50%, more than 60%, more than 70%, more than 80%, more than 85%, more than 90%, more than 95%, or 100% of the total LC-PUFA in the nutritional formula is in the form of monoglycerides and/or free fatty acids. In some embodiments, more than 10%, more than 15%, more than 20%, more than 30%, more than 40%, more than 50%, more than 60%, more than 70%, more than 80%, more than 85%, more than 90%, more than 95%, or 100% of the DHA is in the form of a monoglyceride and/or a free fatty acid. In some embodiments, more than 10%, more than 15%, more than 20%, more than 30%, more than 40%, more than 50%, more than 60%, more than 70%, more than 80%, more than 85%, more than 90%, more than 95%, or 100% of the ARA is in the form of a monoglyceride and/or a free fatty acid. In some embodiments, more than 10%, more than 15%, more than 20%, more than 30%, more than 40%, more than 50%, more than 60%, more than 70%, more than 80%, more than 85%, more than 90%, more than 95%, or 100% of the EPA is in the form of a monoglyceride and/or a free fatty acid. In some embodiments, more than 10%, more than 15%, more than 20%, more than 30%, more than 40%, more than 50%, more than 60%, more than 70%, more than 80%, more than 85%, more than 90%, more than 95%, or 100% of both the DHA and the ARA is in the form of a monoglyceride and/or a free fatty acid. In a particular embodiment, more than 90% of both the DHA and the ARA is in the form of a monoglyceride and/or a free fatty acid. In a particular embodiment, more than 95% of both the DHA and the ARA is in the form of a monoglyceride and/or a free fatty acid.

In some embodiments, at least 10%, at least 15%, at least 20%, at least 30%, at least 40%, at least 50%, at least 60%, at least 70%, at least 80%, at least 85%, at least 90%, at least 95%, or 100% of the total long-chain fatty acids in the nutritional formula are in the form of monoglycerides and/or free fatty acids. In some embodiments, at least 10%, at least 15%, at least 20%, at least 30%, at least 40%, at least 50%, at least 60%, at least 70%, at least 80%, at least 85%, at least 90%, at least 95%, or 100% of the total LC-PUFA in the nutritional formula is in the form of monoglycerides and/or free fatty acids. In some embodiments, at least 10%, at least 15%, at least 20%, at least 30%, at least 40%, at least 50%, at least 60%, at least 70%, at least 80%, at least 85%, at least 90%, at least 95%, or 100% of the DHA is in the form of a monoglyceride and/or a free fatty acid. In some embodiments, at least 10%, at least 15%, at least 20%, at least 30%, at least 40%, at least 50%, at least 60%, at least 70%, at least 80%, at least 85%, at least 90%, at least 95%, or 100% of the ARA is in the form of a monoglyceride and/or a free fatty acid. In some embodiments, at least 10%, at least 15%, at least 20%, at least 30%, at least 40%, at least 50%, at least 60%, at least 70%, at least 80%, at least 85%, at least 90%, at least 95%, or 100% of the EPA is in the form of a monoglyceride and/or a free fatty acid. In some embodiments, at least 10%, at least 15%, at least 20%, at least 30%, at least 40%, at least 50%, at least 60%, at least 70%, at least 80%, at least 85%, at least 90%, at least 95%, or 100% of both the DHA and the ARA is in the form of a monoglyceride and/or a free fatty acid. In a particular embodiment, at least 90% of both the DHA and the ARA is in the form of a monoglyceride and/or a free fatty acid. In a particular embodiment, at least 95% of both the DHA and the ARA is in the form of a monoglyceride and/or a free fatty acid.

In some embodiments of the invention, the approximate serving size of a nutritional formula of the invention is about 100-110 mL for premature infant formula, 90-150 mL (e.g., 148 mL) for term infant formula, 230-500 mL (e.g., 235-250 mL) for enteral feeds, and 230-250 mL for child formulas and adult formulas. In some embodiments, each serving contains about 10-35 mg of ARA free fatty acids and monoglycerides (as would be obtained from complete hydrolysis of TG-ARA in currently available preterm and term infant formulas) or about 40-50 mg of ARA free fatty acids and monoglycerides (as would be obtained from complete hydrolysis of TG-ARA in a currently available adult formula). In some embodiments, each serving contains about 7-20 mg of DHA free fatty acids and monoglycerides (as would be obtained from complete hydrolysis of TG-DHA in currently available preterm and term infant formulas) or about 10-40 mg of DHA free fatty acids and monoglycerides (as would be obtained from complete hydrolysis of TG-DHA in currently available child and adult formulas). In some embodiments, an adult serving of 230-250 mL contains about 1,100 mg of EPA free fatty acids and monoglycerides and about 240 mg of DHA free fatty acids and monoglycerides (as would be obtained from complete hydrolysis of TG-EPA and TG-DHA in some currently available adult formula, such as ProSure®. In some embodiments of the invention, however, the ability to pre-hydrolyze TG-LCPUFAs before ingestion allows formula to be made with higher levels of LC-PUFAs than in currently available formulas. Accordingly, in some embodiments the amount of free fatty acids and/or monoglycerides of ARA and/or DHA exceeds the amounts that could be obtained from complete hydrolysis of TG-LCPUFAs in currently available formulas. In some embodiments, a serving of a nutritional formula of the invention contains 50-100 mg of LC-PUFA free fatty acids and/or monoglycerides. In some embodiments, a serving of a nutritional formula of the invention contains 100-200 mg of LC-PUFA free fatty acids and/or monoglycerides. In some embodiments, a serving of a nutritional formula of the invention contains 200-300 mg of LC-PUFA free fatty acids and/or monoglycerides. In some embodiments, a serving of a nutritional formula of the invention contains 250-

500 mg of LC-PUFA free fatty acids and/or monoglycerides. In some embodiments, a serving of a nutritional formula of the invention contains 500-1000 mg of LC-PUFA free fatty acids and/or monoglycerides. In some embodiments, a serving of a nutritional formula of the invention contains 1-2 grams of LC-PUFA free fatty acids and/or monoglycerides. In some embodiments, a serving of a nutritional formula of the invention contains 2-3 grams of LC-PUFA free fatty acids and/or monoglycerides.

In some embodiments, the nutritional formula comprises fats, carbohydrates, and proteins (or amino acids). In some embodiments, an infant formula of the invention comprises one, more than one, or all of the following: nonfat milk, lactose, vegetable oil (e.g., one or more of palm olein, coconut, soy, and high oleic sunflower oils), whey protein concentrate, sugars, LC-PUFAs, vitamins, and minerals. In some embodiments, the nutritional formula comprises fats composed of medium-chain fatty acids and fats composed of long-chain fatty acids. In some embodiments, the nutritional formula comprises fats composed of n-6 fatty acids and fats composed of n-3 fatty acids. In some embodiments, the nutritional formula comprises LA and ALA.

In some embodiments, a nutritional formula of the invention does not comprise added lipase. In some embodiments, a device and/or a method of the present invention is used to expose a nutritional formula to a lipase, but the nutritional formula is separated from the lipase before feeding, such that the as-fed nutritional formula does not comprise added lipase. A nutritional formula that does not comprise added lipase refers to a formula in which lipase is not detectable or is present only at very low levels, due, e.g., to leaching of immobilized lipase from a solid support into the formula. In some embodiments, a nutritional formula comprises no more than 0.02% (w/w) lipase, no more than 0.01% (w/w) lipase, no more than 0.005% (w/w) lipase, no more than 0.002% (w/w) lipase, no more than 0.001% (w/w) lipase, no more than 0.0005% (w/w) lipase, no more than 0.0002% (w/w) lipase, or no more than 0.0001% (w/w) lipase. In some embodiments, a nutritional formula comprises less than 0.02% (w/w) lipase, less than 0.01% (w/w) lipase, less than 0.005% (w/w) lipase, less than 0.002% (w/w) lipase, less than 0.001% (w/w) lipase, less than 0.0005% (w/w) lipase, less than 0.0002% (w/w) lipase, or less than 0.0001% (w/w) lipase.

In some embodiments, the nutritional formula comprises a lipase. In some embodiments, the lipase is selected from *Chromobacterium viscosum* lipase, *Pseudomonas fluorescens* lipase, *Burcholderia cepacia* lipase, and *Rhizopus oryzae* lipase. In some embodiments, the lipase is selected from *Chromobacterium viscosum* lipase, *Pseudomonas fluorescens* lipase, and *Rhizopus oryzae* lipase. In some embodiments, the lipase is *Chromobacterium viscosum* lipase. In some embodiments, the lipase is *Pseudomonas fluorescens* lipase. In some embodiments, the lipase is *Rhizopus oryzae* lipase.

In some embodiments, a serving of the nutritional formula contains less than 5,000 units of lipase (with units assessed in a standard olive assay, such as described in *Pharmaceutical Enzymes: Properties and Assay Methods*, R. Ruyssen and A. Lauwers (Eds) Scientific Publishing Company, Ghent, Belgium (1978)). In other embodiments, a serving of the nutritional formula contains less than 3,000 units of lipase. In some embodiments, a serving of the nutritional formula contains less than 1,000 units. In certain embodiments, the formula containing less than 5,000, less than 3,000, or less than 1,000 units of lipase per serving is an infant formula or a medical nutritional formula.

In some embodiments, the nutritional formula contains 0.01 mg to 1 gram of lipase per gram of total fat (whether in free fatty acid, monoglyceride, ester, or triglyceride form) in the nutritional formula. In some embodiments, the nutritional formula contains 0.1 to 500 mg of lipase per gram of total fat in the nutritional formula. In some embodiments, the nutritional formula contains 0.1 to 250 mg of lipase per gram of total fat in the nutritional formula. In some embodiments, the nutritional formula contains 0.1 to 200 mg of lipase per gram of total fat in the nutritional formula. In some embodiments, the nutritional formula contains 0.1 to 150 mg of lipase per gram of total fat in the nutritional formula. In some embodiments, the nutritional formula contains 0.1 to 100 mg of lipase per gram of total fat in the nutritional formula. In some embodiments, the nutritional formula contains 0.1 to 50 mg of lipase per gram of total fat in the nutritional formula. In some embodiments, the nutritional formula contains 1 to 50 mg of lipase per gram of total fat in the nutritional formula. In some embodiments, the nutritional formula contains 25 to 75 mg of lipase per gram of total fat in the nutritional formula. In some embodiments, the nutritional formula contains 1 to 100 mg of lipase per gram of total fat in the nutritional formula. In some embodiments, the nutritional formula contains no more than 50 mg of lipase per gram of total fat in the nutritional formula.

In some embodiments, the nutritional formula contains 0.001 to 10 mg of lipase per milligram of total LC-PUFA (whether in free fatty acid, monoglyceride, ester, or triglyceride form) in the nutritional formula. In some embodiments, the nutritional formula contains 0.001 to 5 mg of lipase per milligram of total LC-PUFA in the nutritional formula. In some embodiments, the nutritional formula contains 0.001 to 3 mg of lipase per milligram of total LC-PUFA in the nutritional formula. In some embodiments, the nutritional formula contains 0.001 to 1 mg of lipase per milligram of total LC-PUFA in the nutritional formula. In some embodiments, the nutritional formula contains 0.001 to 0.5 mg of lipase per milligram of total LC-PUFA in the nutritional formula. In some embodiments, the nutritional formula contains 0.001 to 0.1 mg of lipase per milligram of total LC-PUFA in the nutritional formula. In some embodiments, the nutritional formula contains 0.001 to 0.05 mg of lipase per milligram of total LC-PUFA in the nutritional formula. In some embodiments, the nutritional formula contains 0.01 to 0.1 mg of lipase per milligram of total LC-PUFA in the nutritional formula. In some embodiments, the nutritional formula contains 0.02 to 0.08 mg of lipase per milligram of total LC-PUFA in the nutritional formula. In some embodiments, the nutritional formula contains 0.04 to 0.06 mg of lipase per milligram of total LC-PUFA in the nutritional formula. In some embodiments, the nutritional formula contains no more than 0.1 mg of lipase per milligram of total LC-PUFA in the nutritional formula.

In some embodiments, the nutritional formula contains 0.001 to 10 mg of lipase per milligram of total DHA (whether in free fatty acid, monoglyceride, ester, or triglyceride form) in the nutritional formula. In some embodiments, the nutritional formula contains 0.001 to 5 mg of lipase per milligram of total DHA in the nutritional formula. In some embodiments, the nutritional formula contains 0.001 to 3 mg of lipase per milligram of total DHA in the nutritional formula. In some embodiments, the nutritional formula contains 0.001 to 1 mg of lipase per milligram of total DHA in the nutritional formula. In some embodiments, the nutritional formula contains 0.001 to 0.5 mg of lipase per milligram of total DHA in the nutritional formula. In some embodiments, the nutritional formula contains 0.001 to 0.1 mg of lipase per milligram of total DHA in the nutritional formula. In some embodiments, the nutritional formula contains 0.001 to 0.05 mg of lipase per milligram of total DHA in the nutritional formula. In some embodiments, the nutritional formula contains 0.01 to 0.1 mg of lipase per milligram of total DHA in the nutritional formula. In some embodiments, the nutritional formula contains 0.02 to 0.08 mg of lipase per milligram of total DHA in the nutritional formula. In some embodiments, the nutritional formula contains 0.04 to 0.06 mg of lipase per milligram of total DHA in the nutritional formula.

In some embodiments, the nutritional formula contains 0.001 to 10 mg of lipase per milligram of total ARA (whether in free fatty acid, monoglyceride, ester, or triglyceride form) in the nutritional formula. In some embodiments, the nutritional formula contains 0.001 to 5 mg of lipase per milligram of total ARA in the nutritional formula. In some embodiments, the nutritional formula contains 0.001 to 3 mg of lipase per milligram of total ARA in the nutritional formula. In some embodiments, the nutritional formula contains 0.001 to 1 mg of lipase per milligram of total ARA in the nutritional formula. In some embodiments, the nutritional formula contains 0.001 to 0.5 mg of lipase per milligram of total ARA in the nutritional formula. In some embodiments, the nutritional formula contains 0.001 to 0.1 mg of lipase per milligram of total ARA in the nutritional formula. In some embodiments, the nutritional formula contains 0.001 to 0.05 mg of lipase per milligram of total ARA in the nutritional formula. In some embodiments, the nutritional formula contains 0.01 to 0.1 mg of lipase per milligram of total ARA in the nutritional formula. In some embodiments, the nutritional formula contains 0.02 to 0.08 mg of lipase per milligram of total ARA in the nutritional formula. In some embodiments, the nutritional formula contains 0.04 to 0.06 mg of lipase per milligram of total ARA in the nutritional formula.

In some embodiments, the nutritional formula contains 0.001 to 10 mg of lipase per milligram of total EPA (whether in free fatty acid, monoglyceride, ester, or triglyceride form) in the nutritional formula. In some embodiments, the nutritional formula contains 0.001 to 5 mg of lipase per milligram of total EPA in the nutritional formula. In some embodiments, the nutritional formula contains 0.001 to 3 mg of lipase per milligram of total EPA in the nutritional formula. In some embodiments, the nutritional formula contains 0.001 to 1 mg of lipase per milligram of total EPA in the nutritional formula. In some embodiments, the nutritional formula contains 0.001 to 0.5 mg of lipase per milligram of total EPA in the nutritional formula. In some embodiments, the nutritional formula contains 0.001 to 0.1 mg of lipase per milligram of total EPA in the nutritional formula. In some embodiments, the nutritional formula contains 0.001 to 0.05 mg of lipase per milligram of total EPA in the nutritional formula. In some embodiments, the nutritional formula contains 0.01 to 0.1 mg of lipase per milligram of total EPA in the nutritional formula. In some embodiments, the nutritional formula contains 0.02 to 0.08 mg of lipase per milligram of total EPA in the nutritional formula. In some embodiments, the nutritional formula contains 0.04 to 0.06 mg of lipase per milligram of total EPA in the nutritional formula.

In some embodiments, a nutritional formula is prepared by a method disclosed herein. In some embodiments, a nutritional formula is prepared using a device disclosed herein.

Methods of Preparing a Nutritional Formula

According to various embodiments, the present disclosure also provides methods of preparing nutritional formulas. In some embodiments, the nutritional formula is an infant formula. In some embodiments, the nutritional formula is a medical nutritional formula. In some embodiments, the nutritional formula is a nutritional drink for adults (such as a complete nutritional drink, e.g., ENSURE, PEDIASURE).

In some embodiments, a method of preparing a nutritional formula comprises exposing a liquid nutritional composition to a lipase. In some embodiments, the liquid nutritional composition comprises LC-PUFA triglycerides or LC-PUFA esters. In some embodiments, the liquid nutritional composition comprises triglycerides or esters of one or more LC-PUFAs selected from the group consisting of DHA, ARA, and EPA.

In some embodiments, the liquid nutritional composition is exposed to a lipase selected from *Chromobacterium viscosum* lipase, *Pseudomonas fluorescens* lipase, *Burcholderia cepacia* lipase, and *Rhizopus oryzae* lipase. In some embodiments, the lipase is selected from *Chromobacterium viscosum* lipase, *Pseudomonas fluorescens* lipase, and *Rhizopus oryzae* lipase. In some embodiments, the lipase is *Chromobacterium viscosum* lipase. In some embodiments, the lipase is *Pseudomonas fluorescens* lipase. In some embodiments, the lipase is *Rhizopus oryzae* lipase.

Components involved in these methods may be mixed in various orders. In some embodiments, lipase is added to a liquid nutritional composition, thereby exposing lipids in the liquid nutritional composition to the lipase. In some embodiments, a liquid nutritional composition is prepared by adding a potable liquid to a solid or powder form of the nutritional composition. In some embodiments, lipase is present in the solid or powder form of the nutritional composition before the addition of potable liquid. In other embodiments, lipase is added after the liquid nutritional composition is prepared. In some embodiments, the lipase and the solid or powder form of the nutritional composition are added to a potable liquid at the same time.

In some embodiments, the liquid nutritional composition is exposed to lipase for at least one minute, at least 2 minutes, at least 3 minutes, at least 5 minutes, at least 8 minutes, at least 10 minutes, at least 15 minutes, at least 30 minutes, at least 45 minutes, or at least 60 minutes prior to ingestion. In some embodiments, the liquid nutritional composition is exposed to lipase for no more than 30 seconds, no more than 1 minute, no more than 2 minutes, no more than 3 minutes, no more than 5 minutes, no more than 8 minutes, no more than 10 minutes, no more than 15 minutes, no more than 30 minutes, no more than 45 minutes, no more than 60 minutes, no more than 2 hours, no more than 4 hours, no more than 6 hours, no more than 12 hours, or no more than 24 hours.

In some embodiments, the method results in a nutritional formula in which at least 10%, at least 15%, at least 20%, at least 30%, at least 40%, at least 50%, at least 60%, at least 70%, at least 80%, at least 85%, at least 90%, at least 95%, or 100% of the total LC-PUFA in the nutritional formula is in the form of monoglycerides and/or free fatty acids. In some embodiments, at least 10%, at least 15%, at least 20%, at least 30%, at least 40%, at least 50%, at least 60%, at least 70%, at least 80%, at least 85%, at least 90%, at least 95%, or 100% of the DHA is in the form of a monoglyceride and/or a free fatty acid. In some embodiments, at least 10%, at least 15%, at least 20%, at least 30%, at least 40%, at least 50%, at least 60%, at least 70%, at least 80%, at least 85%, at least 90%, at least 95%, or 100% of the ARA is in the form of a monoglyceride and/or a free fatty acid. In some embodiments, at least 10%, at least 15%, at least 20%, at least 30%, at least 40%, at least 50%, at least 60%, at least 70%, at least 80%, at least 85%, at least 90%, at least 95%, or 100% of the EPA is in the form of a monoglyceride and/or a free fatty acid.

For purposes of this application, exposure of a nutritional composition or formula to a lipase refers to the period of time in which a liquid nutritional composition or liquid formula is in contact with a lipase, which may be in solution or immobilized. For purposes of this application, exposure to a lipase ends when the formula is ingested by a subject or when the lipase is removed by separating the liquid formula from a solid support to which the lipase is immobilized. In some embodiments, the liquid nutritional composition is exposed to lipase for no more than 10 minutes, and at least 20% of the DHA in the resulting nutritional formula is in the form of a monoglyceride and/or a free fatty acid. In some embodiments, the liquid nutritional composition is exposed to lipase for no more than 10 minutes, and at least 20% of the ARA in the resulting nutritional formula is in the form of a monoglyceride and/or a free fatty acid. In some embodiments, the liquid nutritional composition is exposed to lipase for no more than 10 minutes, and at least 20% of the total LC-PUFA in the resulting nutritional formula is in the form of a monoglyceride and/or a free fatty acid.

In some embodiments, the liquid nutritional composition is exposed to lipase for no more than 10 minutes, and at least 40% of the DHA in the resulting nutritional formula is in the form of a monoglyceride and/or a free fatty acid. In some embodiments, the liquid nutritional composition is exposed to lipase for no more than 10 minutes, and at least 40% of the ARA in the resulting nutritional formula is in the form of a monoglyceride and/or a free fatty acid. In some embodiments, the liquid nutritional composition is exposed to lipase for no more than 10 minutes, and at least 40% of the total LC-PUFA in the resulting nutritional formula is in the form of a monoglyceride and/or a free fatty acid.

In some embodiments, the liquid nutritional composition is exposed to lipase for no more than 10 minutes, and at least 50% of the DHA in the resulting nutritional formula is in the form of a monoglyceride and/or a free fatty acid. In some embodiments, the liquid nutritional composition is exposed to lipase for no more than 10 minutes, and at least 50% of the ARA in the resulting nutritional formula is in the form of a monoglyceride and/or a free fatty acid. In some embodiments, the liquid nutritional composition is exposed to lipase for no more than 10 minutes, and at least 50% of the total LC-PUFA in the resulting nutritional formula is in the form of a monoglyceride and/or a free fatty acid.

In some embodiments, the liquid nutritional composition is exposed to lipase for no more than 10 minutes, and at least 60% of the DHA in the resulting nutritional formula is in the form of a monoglyceride and/or a free fatty acid. In some embodiments, the liquid nutritional composition is exposed to lipase for no more than 10 minutes, and at least 60% of the ARA in the resulting nutritional formula is in the form of a monoglyceride and/or a free fatty acid. In some embodiments, the liquid nutritional composition is exposed to lipase for no more than 10 minutes, and at least 60% of the total LC-PUFA in the resulting nutritional formula is in the form of a monoglyceride and/or a free fatty acid.

In some embodiments, the liquid nutritional composition is exposed to lipase for no more than 10 minutes, and at least 70% of the DHA in the resulting nutritional formula is in the form of a monoglyceride and/or a free fatty acid. In some embodiments, the liquid nutritional composition is exposed to lipase for no more than 10 minutes, and at least 70% of the ARA in the resulting nutritional formula is in the form of a monoglyceride and/or a free fatty acid. In some embodiments, the liquid nutritional composition is exposed to lipase for no more than 10 minutes, and at least 70% of the total LC-PUFA in the resulting nutritional formula is in the form of a monoglyceride and/or a free fatty acid.

In some embodiments, the liquid nutritional composition is exposed to lipase for no more than 20 minutes, and at least 20% of the DHA in the resulting nutritional formula is in the form of a monoglyceride and/or a free fatty acid. In some embodiments, the liquid nutritional composition is exposed to lipase for no more than 20 minutes, and at least 20% of the ARA in the resulting nutritional formula is in the form of a monoglyceride and/or a free fatty acid. In some embodiments, the liquid nutritional composition is exposed to lipase for no more than 20 minutes, and at least 20% of the total LC-PUFA in the resulting nutritional formula is in the form of a monoglyceride and/or a free fatty acid.

In some embodiments, the liquid nutritional composition is exposed to lipase for no more than 20 minutes, and at least 40% of the DHA in the resulting nutritional formula is in the form of a monoglyceride and/or a free fatty acid. In some embodiments, the liquid nutritional composition is exposed to lipase for no more than 20 minutes, and at least 40% of the ARA in the resulting nutritional formula is in the form of a monoglyceride and/or a free fatty acid. In some embodiments, the liquid nutritional composition is exposed to lipase for no more than 20 minutes, and at least 40% of the total LC-PUFA in the resulting nutritional formula is in the form of a monoglyceride and/or a free fatty acid.

In some embodiments, the liquid nutritional composition is exposed to lipase for no more than 20 minutes, and at least 50% of the DHA in the resulting nutritional formula is in the form of a monoglyceride and/or a free fatty acid. In some embodiments, the liquid nutritional composition is exposed to lipase for no more than 20 minutes, and at least 50% of the ARA in the resulting nutritional formula is in the form of a monoglyceride and/or a free fatty acid. In some embodiments, the liquid nutritional composition is exposed to lipase for no more than 20 minutes, and at least 50% of the total LC-PUFA in the resulting nutritional formula is in the form of a monoglyceride and/or a free fatty acid.

In some embodiments, the liquid nutritional composition is exposed to lipase for no more than 20 minutes, and at least 80% of the DHA in the resulting nutritional formula is in the form of a monoglyceride and/or a free fatty acid. In some embodiments, the liquid nutritional composition is exposed to lipase for no more than 20 minutes, and at least 80% of the ARA in the resulting nutritional formula is in the form of a monoglyceride and/or a free fatty acid. In some embodiments, the liquid nutritional composition is exposed to lipase for no more than 20 minutes, and at least 80% of the total LC-PUFA in the resulting nutritional formula is in the form of a monoglyceride and/or a free fatty acid.

In some embodiments, the liquid nutritional composition is exposed to lipase for no more than 20 minutes, and at least 90% of the DHA in the resulting nutritional formula is in the form of a monoglyceride and/or a free fatty acid. In some embodiments, the liquid nutritional composition is exposed to lipase for no more than 20 minutes, and at least 90% of the ARA in the resulting nutritional formula is in the form of a monoglyceride and/or a free fatty acid. In some embodiments, the liquid nutritional composition is exposed to lipase for no more than 20 minutes, and at least 90% of the total LC-PUFA in the resulting nutritional formula is in the form of a monoglyceride and/or a free fatty acid.

In some embodiments, the liquid nutritional composition is exposed to lipase for no more than 30 minutes, and at least 20% of the DHA in the resulting nutritional formula is in the form of a monoglyceride and/or a free fatty acid. In some embodiments, the liquid nutritional composition is exposed to lipase for no more than 30 minutes, and at least 20% of the ARA in the resulting nutritional formula is in the form of a monoglyceride and/or a free fatty acid. In some embodiments, the liquid nutritional composition is exposed to lipase for no more than 30 minutes, and at least 20% of the total LC-PUFA in the resulting nutritional formula is in the form of a monoglyceride and/or a free fatty acid.

In some embodiments, the liquid nutritional composition is exposed to lipase for no more than 30 minutes, and at least 40% of the DHA in the resulting nutritional formula is in the form of a monoglyceride and/or a free fatty acid. In some embodiments, the liquid nutritional composition is exposed to lipase for no more than 30 minutes, and at least 40% of the ARA in the resulting nutritional formula is in the form of a monoglyceride and/or a free fatty acid. In some embodiments, the liquid nutritional composition is exposed to lipase for no more than 30 minutes, and at least 40% of the total LC-PUFA in the resulting nutritional formula is in the form of a monoglyceride and/or a free fatty acid.

In some embodiments, the liquid nutritional composition is exposed to lipase for no more than 30 minutes, and at least 60% of the DHA in the resulting nutritional formula is in the form of a monoglyceride and/or a free fatty acid. In some embodiments, the liquid nutritional composition is exposed to lipase for no more than 30 minutes, and at least 60% of the ARA in the resulting nutritional formula is in the form of a monoglyceride and/or a free fatty acid. In some embodiments, the liquid nutritional composition is exposed to lipase for no more than 30 minutes, and at least 60% of the total LC-PUFA in the resulting nutritional formula is in the form of a monoglyceride and/or a free fatty acid.

In some embodiments, the liquid nutritional composition is exposed to lipase for no more than 30 minutes, and at least 70% of the DHA in the resulting nutritional formula is in the form of a monoglyceride and/or a free fatty acid. In some embodiments, the liquid nutritional composition is exposed to lipase for no more than 30 minutes, and at least 70% of the ARA in the resulting nutritional formula is in the form of a monoglyceride and/or a free fatty acid. In some embodiments, the liquid nutritional composition is exposed to lipase for no more than 30 minutes, and at least 70% of the total LC-PUFA in the resulting nutritional formula is in the form of a monoglyceride and/or a free fatty acid.

In some embodiments, the liquid nutritional composition is exposed to lipase for no more than 30 minutes, and at least 80% of the DHA in the resulting nutritional formula is in the form of a monoglyceride and/or a free fatty acid. In some embodiments, the liquid nutritional composition is exposed to lipase for no more than 30 minutes, and at least 80% of the ARA in the resulting nutritional formula is in the form of a monoglyceride and/or a free fatty acid. In some embodiments, the liquid nutritional composition is exposed to lipase for no more than 30 minutes, and at least 80% of the total LC-PUFA in the resulting nutritional formula is in the form of a monoglyceride and/or a free fatty acid.

In some embodiments, the lipase remains in the nutritional formula when it is fed to the subject. In other embodiments, the lipase is removed from the liquid nutritional composition before it is fed to the subject. In some embodiments, the lipase is removed by exposing the liquid nutritional composition comprising the lipase to a solid support immobilized to a molecule that binds to the lipase, thereby binding the lipase to the solid support, and separating the liquid nutritional composition from the solid support. Since the lipase is immobilized to the solid support, separating the liquid nutritional composition from the solid support has the effect of removing the lipase from the liquid nutritional composition. In some embodiments, the lipase is immobilized to a solid support before it is exposed to the liquid nutritional composition, and the lipase is removed by separating the liquid nutritional composition from the solid support. In some embodiments, the lipase is immobilized to at least a portion of an interior face of a chamber or to a solid support contained within the chamber, and the liquid nutritional composition is temporarily exposed to the lipase by passing through the chamber. In some embodiments, the chamber is a column. In some embodiments, the liquid nutritional composition is exposed to a container containing lipase immobilized to a solid support, and at least a portion of the inner surface of the container consists of a material that is permeable to triglycerides and esters but is not permeable to the solid support.

In some embodiments, the method produces a nutritional formula that does not comprise added lipase. In some embodiments, a nutritional formula is exposed to a lipase, but the nutritional formula is separated from the lipase before feeding, such that the as-fed nutritional formula does not comprise added lipase. A nutritional formula that does not comprise (or contain) added lipase refers to a formula in which lipase is not detectable or is present only at very low levels, due, e.g., to leaching of immobilized lipase from a solid support into the formula. In some embodiments, a nutritional formula comprises no more than 0.02% (w/w) lipase, no more than 0.01% (w/w) lipase, no more than 0.005% (w/w) lipase, no more than 0.002% (w/w) lipase, no more than 0.001% (w/w) lipase, no more than 0.0005% (w/w) lipase, no more than 0.0002% (w/w) lipase, or no more than 0.0001% (w/w) lipase. In some embodiments, a nutritional formula comprises less than 0.02% (w/w) lipase, less than 0.01% (w/w) lipase, less than 0.005% (w/w) lipase, less than 0.002% (w/w) lipase, less than 0.001% (w/w) lipase, less than 0.0005% (w/w) lipase, less than 0.0002% (w/w) lipase, or less than 0.0001% (w/w) lipase.

In some embodiments, the method comprises exposing the nutritional formula to less than 5,000 units of lipase per serving (with units assessed in a standard olive assay, such as described in *Pharmaceutical Enzymes: Properties and Assay Methods*, R. Ruyssen and A. Lauwers (Eds) Scientific Publising Company, Ghent, Gelgium (1978)). In other embodiments, the nutritional formula is exposed to less than 3,000 units of lipase per serving. In some embodiments, the nutritional formula is exposed to less than 1,000 units of lipase per serving. In certain embodiments, the formula exposed to less than 5,000, less than 3,000, or less than 1,000 units of lipase per serving is an infant formula or a medical nutritional formula.

In some embodiments, a method of the invention exposes the nutritional formula to 0.01 mg to 1 gram of lipase per gram of total fat (whether in free fatty acid, monoglyceride, ester, or triglyceride form) in the nutritional formula. In some embodiments, a method of the invention exposes the nutritional formula to 0.1 to 500 mg of lipase per gram of total fat in the nutritional formula. In some embodiments, a method of the invention exposes the nutritional formula to 0.1 to 250 mg of lipase per gram of total fat in the nutritional formula. In some embodiments, a method of the invention exposes the nutritional formula to 0.1 to 200 mg of lipase per gram of total fat in the nutritional formula. In some embodiments, a method of the invention exposes the nutritional formula to 0.1 to 150 mg of lipase per gram of total fat in the nutritional formula. In some embodiments, a method of the invention exposes the nutritional formula to 0.1 to 100 mg of lipase per gram of total fat in the nutritional formula. In some embodiments, a method of the invention exposes the nutritional formula to 0.1 to 50 mg of lipase per gram of total fat in the nutritional formula. In some embodiments, a method of the invention exposes the nutritional formula to 1 to 50 mg of lipase per gram of total fat in the nutritional formula. In some embodiments, a method of the invention exposes the nutritional formula to 25 to 75 mg of lipase per gram of total fat in the nutritional formula. In some embodiments, a method of the invention exposes the nutritional formula to 1 to 100 mg of lipase per gram of total fat in the nutritional formula. In some embodiments, a method of the invention exposes the nutritional formula to no more than 50 mg of lipase per gram of total fat in the nutritional formula.

In some embodiments, the method exposes the nutritional formula to 0.001 to 10 mg of lipase per milligram of total LC-PUFA (whether in free fatty acid, monoglyceride, ester, or triglyceride form) in the nutritional formula. In some embodiments, the nutritional formula is exposed to 0.001 to 5 mg of lipase per milligram of total LC-PUFA in the nutritional formula. In some embodiments, the nutritional formula is exposed to 0.001 to 3 mg of lipase per milligram of total LC-PUFA in the nutritional formula. In some embodiments, the nutritional formula is exposed to 0.001 to 1 mg of lipase per milligram of total LC-PUFA in the nutritional formula. In some embodiments, the nutritional formula is exposed to 0.001 to 0.5 mg of lipase per milligram of total LC-PUFA in the nutritional formula. In some embodiments, the nutritional formula is exposed to 0.001 to 0.1 mg of lipase per milligram of total LC-PUFA in the nutritional formula. In some embodiments, the nutritional formula is exposed to 0.001 to 0.05 mg of lipase per milligram of total LC-PUFA in the nutritional formula. In some embodiments, the nutritional formula is exposed to 0.01 to 0.1 mg of lipase per milligram of total LC-PUFA in the nutritional formula. In some embodiments, the nutritional formula is exposed to 0.02 to 0.08 mg of lipase per milligram of total LC-PUFA in the nutritional formula. In some embodiments, the nutritional formula is exposed to 0.04 to 0.06 mg of lipase per milligram of total LC-PUFA in the nutritional formula. In some embodiments, the nutritional formula is exposed to no more than 0.1 mg of lipase per milligram of total LC-PUFA in the nutritional formula.

In some embodiments, the method exposes the nutritional formula to 0.001 to 10 mg of lipase per milligram of total DHA (whether in free fatty acid, monoglyceride, ester, or triglyceride form) in the nutritional formula. In some embodiments, the nutritional formula is exposed to 0.001 to 5 mg of lipase per milligram of total DHA in the nutritional formula. In some embodiments, the nutritional formula is exposed to 0.001 to 3 mg of lipase per milligram of total DHA in the nutritional formula. In some embodiments, the nutritional formula is exposed to 0.001 to 1 mg of lipase per milligram of total DHA in the nutritional formula. In some embodiments, the nutritional formula is exposed to 0.001 to 0.5 mg of lipase per milligram of total DHA in the nutritional formula. In some embodiments, the nutritional formula is exposed to 0.001 to 0.1 mg of lipase per milligram of total DHA in the nutritional formula. In some embodiments, the nutritional formula is exposed to 0.001 to 0.05 mg of lipase per milligram of total DHA in the nutritional formula. In some embodiments, the nutritional formula is exposed to 0.01 to 0.1 mg of lipase per milligram of total DHA in the nutritional formula. In some embodiments, the nutritional formula is exposed to 0.02 to 0.08 mg of lipase per milligram of total DHA in the nutritional formula. In some embodiments, the nutritional formula is exposed to 0.04 to 0.06 mg of lipase per milligram of total DHA in the nutritional formula.

In some embodiments, a method of preparing a nutritional formula comprises exposing a liquid nutritional composition to a device as described herein.

Example 1: Specific Activities of Lipases for DHA and ARA

To evaluate the enzymatic activity of various lipases on DHA and/or ARA triglycerides, experiments were performed in a two mL glass vial (with magnetic stir bar) containing 0.1M Tris buffer, pH 7.7 and the substrate DHA or ARA triglycerides. The reaction was initiated by adding lipase solutions. Lipases were obtained from commercial sources as follows: *Rhizopus oryzae* (Amano DF-15, Amano Enzymes Inc., Nagoya, Japan), *Chromobacterium viscosum* (EMD CalBiochem, EMD Biosciences, Billerica, Mass.), and *Pseudomonas fluoresens* (Amano AK, Amano Enzymes Inc., Nagoya, Japan). Other lipases are also available from commercial sources, such as *Candida rugosa* (Amano AY 30 or Amano 30, Amano Enzymes Inc., Nagoya, Japan), *Aspergillus niger* (Amano DS, Amano Enzymes Inc., Nagoya, Japan), *Penicillium camembertii* (Amano 50, Amano Enzymes Inc., Nagoya, Japan), *Rhizomucor miehei* (L4277, Sigma-Aldrich), *Asperigillus oryzae* (62285, Sigma-Aldrich), and *Burcholderia cepacia* (534641, Sigma-Aldrich). Lipase solutions were prepared from these commercially available lipases without additional purification, except that *B. cepacia* lipase was purified to homogeneity.

The vials were transferred to a water-bath at 37° C. placed on a magnetic stirrer. 50 μl of samples were taken at different time intervals—0, 15, 30, 45, 60, 90, and 120 min and added to a HPLC vial containing 950 μl of running buffer (30% 10 mM ammonium phosphate buffer, pH 3.0 and 70% acetonitrile). The samples were then analyzed for either DHA free acid or ARA free acid by reverse phase high performance liquid chromatography (RP-HPLC) using an Agilent HPLC1100 series and a C8 RP column and monitoring at 215 and 220 nm. The free acid peaks were identified according to retention times using commercially available standards: DHA triglyceride (Nu-check Prep, Inc. Lot No. T-310-D7-V), ARA triglyceride (Nu-check Prep, Inc. Lot No. T-295-JY14-V), DHA free acid form (Nu-check Prep, Inc. Lot No. U-84A-AU20-U), and ARA free acid form (Nu-check Prep, Inc. Lot No. U-71A-N11-U). The specific activities of a panel of lipases in this assay for DHA and ARA are summarized in Table 1. In the inventors' hands, *Chromobacterium viscosum* (CV), *Burcholderia cepacia* (BC), *Pseudomonas fluoresens* (PF), and *Rhizopus oryzae* (RO) had substantially higher specific activity toward DHA and/or ARA compared to the other lipases tested, including *Candida rugosa* (CR).

TABLE 1

Specific activities of lipases for DHA and ARA

| Enzyme | DHA produced, Πmol/min/mg | ARA produced, Πmol/min/mg |
|---|---|---|
| CV | 27.73 | 23.207 |
| PF | 4.66 | 2.599 |
| RO | 9.83 | 6.297 |
| CR | 0.01 | 0.205 |

TABLE 1-continued

Specific activities of lipases for DHA and ARA

| Enzyme | DHA produced, Πmol/min/mg | ARA produced, Πmol/min/mg |
|---|---|---|
| AN | 0.00 | 0.000 |
| PC | 0.00 | 0.000 |
| BC | 55.11 | 13.920 |
| AO | 0.33 | 0.263 |
| RM | 0.14 | 0.03 |

Example 2: Enzymatic Activity of Chromobacterium viscosum and Rhizopus oryzae Lipases for DHA, ARA, and EPA in Infant Formula To evaluate the enzymatic activity of CV and RO lipase on DHA, ARA, and EPA when supplemented to infant formula, milk-based infant formula was prepared by dissolving 10 g of ENFAMIL® powder in 35 mL of water. Infant formula containing substrate EPA, 0.1M Tris buffer, pH 7.7, and substrates 2.7 mg DHA (Nu-check Prep, Inc. Lot No. T-310-D7-V) and 5.4 mg ARA (Nu-check Prep, Inc. Lot No. T-295) were added to a one mL glass vial (with magnetic stir bar). The reaction was initiated by adding enzyme (i.e. lipase); four concentrations of each enzyme were tested. The vials were transferred to a water bath at 37° C. placed on a magnetic stirrer. 50 µl of each sample were taken at different time points—0, 10, 20, 30, 45, and 60 min and added to a HPLC vial containing 950 µl of HPLC running buffer (30% 10 mM ammonium phosphate buffer, pH 3.0 and 70% acetonitrile). The samples were then analyzed for either DHA acid, ARA acid, or EPA acid by RP-HPLC as above.

Figure 7:
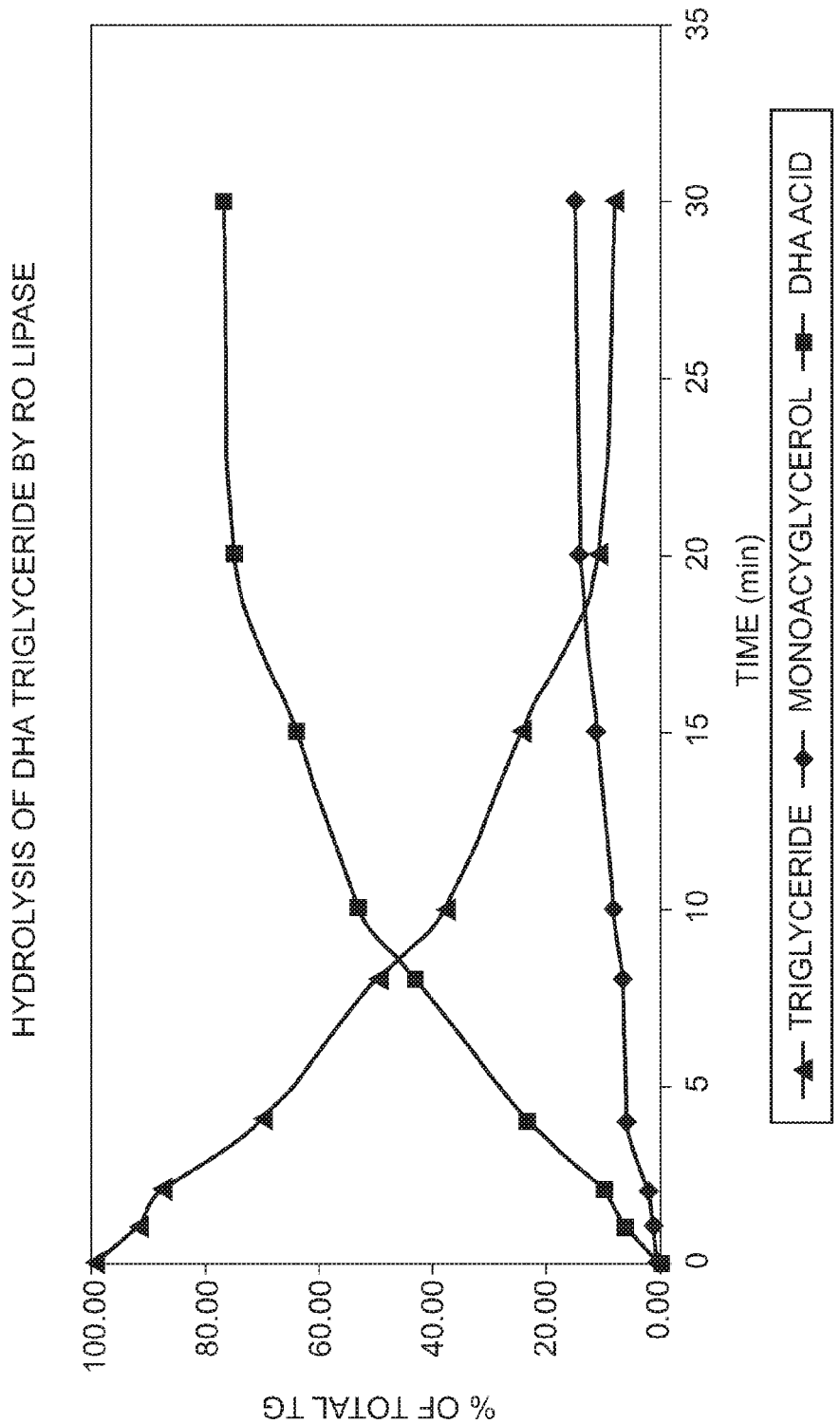
FIG. 7 depicts the hydrolysis of DHA triglyceride by *Rhizopus oryzae* (RO) lipase.
Figure 8:
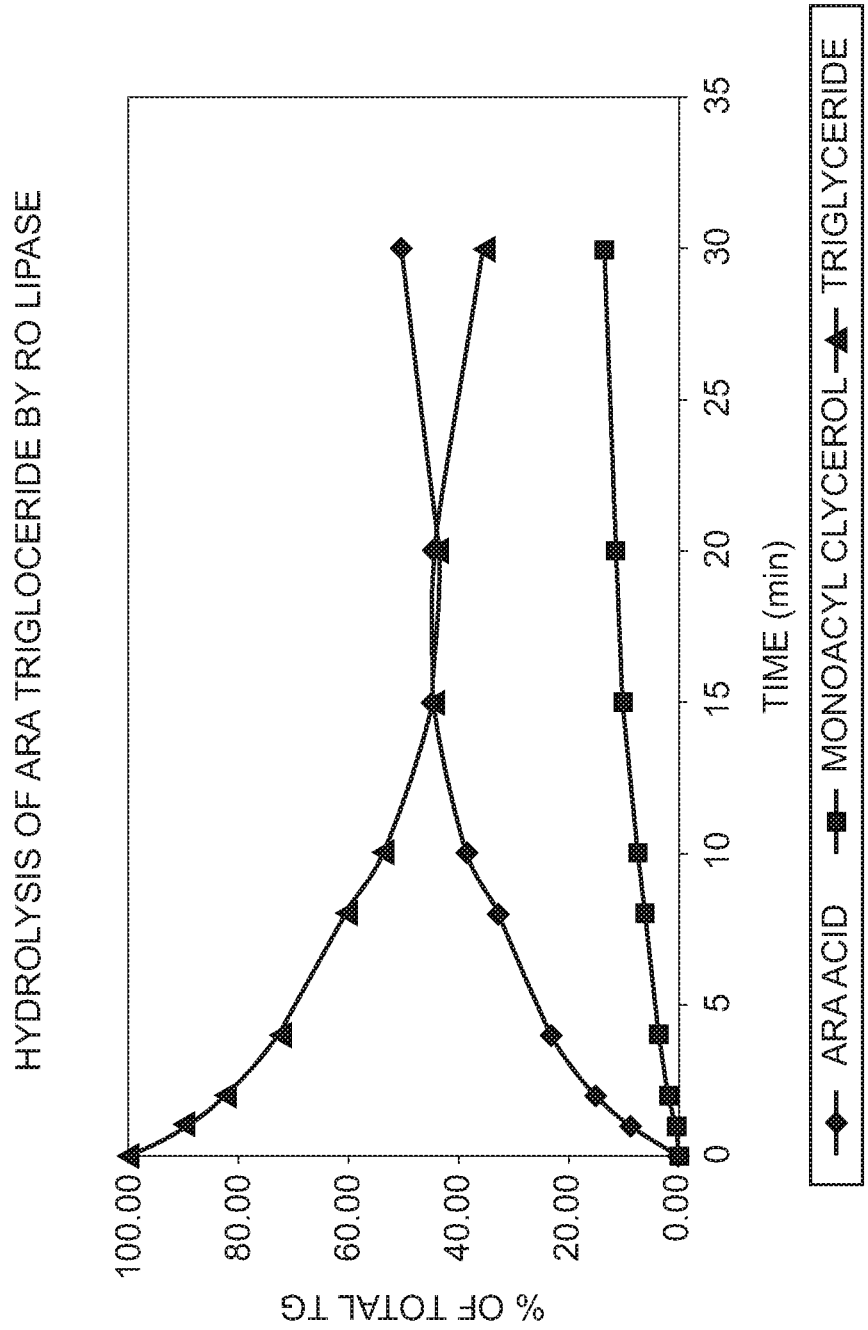
FIG. 8 depicts the hydrolysis of ARA triglyceride by *Rhizopus oryzae* lipase.

The percent of total triglycerides decreased over time as the amount of free acid and monoglyceride increased. For example, when hydrolyzed with RO, the amount of DHA free acid increased with time (FIG. 7). Similarly, when hydrolyzed with RO, the amount of ARA free acid increased with time (FIG. 8).

The specific activities of each of the lipases in this assay were calculated based on the amount of free DHA acid, ARA acid, or EPA acid released in the infant formula and are shown in Table 2.

TABLE 2

Specific activities of lipases on TG-DHA, TG-ARA, and TG-EPA in infant formula

| Enzyme | DHA produced, µmol/min/mg | ARA produced, µmol/min/mg | EPA produced, µmol/min/mg |
|---|---|---|---|
| CV | 39.461 | 36.587 | 19.866 |
| RO | 13.062 | 10.940 | 14.156 |

Example 3: Hydrolysis of DHA Triglyceride and ARA Triglyceride Scale Up

Lipases were evaluated for their ability to hydrolyze TG-DHA and TG-ARA when scaled up to an amount that may be used for supplementing infant formula. The infant formula (milk) was prepared by dissolving 162 g of Enfamil powder in 648 mL of tap water (hot water, the temperature was 37° C.). DHA triglyceride (442 mg, final concentration of DHA was 0.54 g, 1.2% of total fat) and ARA triglyceride (885 mg, final concentration ARA 1.08 g, 2.4% of total fat) were accurately weighed from the same source as in Example 2, and were mixed with the infant formula powder before adding the water. The reaction was carried out in a water-bath with constant stirring. Fat hydrolysis was initiated by adding either CV or RO lipase. Formula samples were withdrawn at 0, 15, and 30 minutes and were analyzed for hydrolysis of DHA and ARA by RP-HPLC, as described above. The results are shown in Table 3 below.

TABLE 3

Hydrolysis of TG-DHA and TG-ARA in infant formula

| | Lipase, mg | % Hydrolysis DHA | | % Hydrolysis ARA | |
|---|---|---|---|---|---|
| | | 15 min | 30 min | 15 min | 30 min |
| CV | 9 | 75.17 | 71.32 | 58.97 | 74.38 |
| | 18 | 84.51 | 87.25 | 65.83 | 63.31 |
| RO | 29 | 62.35 | 71.19 | 104.81 | 124.67 |
| | 58 | 73 | 67.77 | 124.22 | 113.08 |

Example 4: Enzymatic Activity of Immobilized Rhizopus oryzae Lipase on TG-DHA or TG-ARA in Infant Formula and Buffer To evaluate the enzymatic activity of immobilized RO lipase on TG-DHA or TG-ARA when supplemented to infant formula, milk-based infant formula was prepared by dissolving 10 g of ENFAMIL® powder in 35 mL of water. The reaction was carried out as follows. Infant formula, 0.1M Tris buffer, pH 7.7, and substrate (TG-DHA or TG-ARA) were added to a one mL glass vial (with magnetic stir bar). The reaction was initiated by adding lipase. The vials were transferred to a water bath at 37° C. placed on a magnetic stirrer. 50 µl of each sample were taken at different time points—0, 10, 20, and 30 min and added to a HPLC vial containing 900 µl of HPLC running buffer (30% 10 mM ammonium phosphate buffer, pH 3.0 and 70% acetonitrile). The samples were then analyzed for either DHA acid or ARA acid by RP-HPLC as described above.

The specific activities of the lipase for hydrolysis of TG-DHA and TG-ARA were calculated based on the amount of free DHA acid or ARA acid released in the infant formula and are shown in Table 4.

TABLE 4

Specific activities of Immobilized RO lipase on TG-DHA or TG-ARA in infant formula and Buffer

| Enzyme | DHA produced, µmol/min/mg | ARA produced, µmol/min/mg |
|---|---|---|
| Immobilized Rhizopus oryzae lipase (RO) | 0.017 (0.004) | 0.020 (0.008) |

Example 5: Animals and Surgical Procedure

5.1 Animals

The experiments were performed on 12 pigs (9+3) from the University herd at Odarslöv; Swedish Agricultural University, Department of Agricultural Biosystems and Technology, weighing approximately 10±2 kg each. Animals were maintained on a 12 hour day-night cycle, with light from 06.00-18.00 (6 am-6 pm) and dark from 18.00-06.00 (6 pm-6 am) hours. The pigs were individually housed in metabolic cages or individual pens equipped with a dry feeding trough, a drinking nipple and a constant heating lamp (150 W). They were allowed to move freely within their pen, and have visual contact with each other.

5.2 Feed

Following surgery and during the pre-treatment period, pigs were fed a standard pig diet ("53908 Växtill 320 P BK", Lantmännen, Sweden) containing 17.5% crude protein, 3.9% crude fibre, 3.5% crude fat, and 5.2% ash together with 5000 IE/kg vitamine A, 500 IE/kg vitamine D, and 85 mg/kg vitamine E. Pigs were fed twice daily (2.0% of body mass per meal) at 09:00-10:00 hr (9 am-10 am) and 17:00-18:00 hr (5 pm-6 pm). For a few days before the start of the experiment, i.e., before the adaptation period, pigs were trained to consume infant formula (NAN Pro 1 Gold Infant Formula, Nestle). Formula was prepared as a 1:4 dilution in tap water instead of 1:7 as recommended by manufacturer to allow proper consumption, since pigs do not like to drink large volumes of liquid. Daily nutrient requirements are 400 kJ/kg body weight, corresponding 40 g of formula powder/kg body weight. Daily feed was divided into 4 portions, starting with the first meal at 9 am and than, every 3 h after with the last meal of day at 6 pm. 100 g of NAN formula contains about 27.7% fat, 9.6% protein, and 57.8% carbohydrates.

5.3 Infant Formula Milk Fortified with DHA and ARA Triglycerides

According to the manufacturer, NAN Pro 1 Gold (Nestle) is a premium whey predominant starter infant formula that is nutritionally complete and specially formulated for healthy infants from birth. It also contains fish oil to help support brain and visual development. (http://www.nestlebaby.com/au/baby_nutrition/products/infant_formula/)

NAN Pro 1 Gold Ingredients:

Milk solids, vegetable oils (contains soy), minerals (calcium citrate, potassium citrate, potassium chloride, magnesium chloride, sodium chloride, sodium sulphate, ferrous sulphate, zinc sulphate, calcium phosphate, copper sulphate, manganese sulphate, potassium iodide, sodium selenate), omega LCPUFAs (DHA from fish oil, AA), emulsifier (soy lecithin), vitamins [sodium ascorbate (vit C), d-l alpha tocopheryl acetate (vit E), niacinamide (niacin), calcium pantothenate, retinyl acetate (vit A), thiamine mononitrate (vit B1), pyridoxine hydrochloride (vit B6), riboflavin (vit B2), folic acid, phylloquinone (vit K1), biotin, cholecalciferol (vit D3)], cyanocobalamin (B 12), L-histidine, taurine, inositol, nucleotides (cytidine 5'-monophosphate, uridine 5'-monophosphate, adenosine 5'-monophosphate, guanosine 5'-monophosphate), L-carnitine, culture (bifidus).

Table 5 below summarizes the lipid composition of human milk and infant formula milk*, together with infant formula and pig formula milk for use in these experiments.

TABLE 5

| | LCPUFA fortified formula milk | | | |
|---|---|---|---|---|
| | Human milk* | Infant term formula | Infant pre-term formula | Pig formula for study in EPI pigs |
| TG g/L | 25-29 | 33-36 | 25 | 50 |
| Cholesterol mg/dL | 9-15 | 0-4 | | 10 |

TABLE 5-continued

| | LCPUFA fortified formula milk | | | |
|---|---|---|---|---|
| | Human milk* | Infant term formula | Infant pre-term formula | Pig formula for study in EPI pigs |
| In % of total FA | | | | |
| Palmitate C16:0 | 20-25 | 8-24 | NA* | NA* |
| Sterate C18:0 | 7-12 | 2-6 | NA* | NA* |
| LA C18:2n-6 | 10-15.5 | 10-29.9 | 4.5 | NA* |
| LNA C18:3n-3 | 0.58-1.44 | 0.08-2 | 0.086 | NA* |
| DHA C22:6n-3 (ω 3) | 0.19-0.42 | 0-0.15 | 0.083 | Up to 1.6%** |
| ARA C20:4n-6 (ω 6) | 0.4-0.54 | 0-0.4 | 0.167* | Up to 3.15%** |

*Data from various women cohorts in Australia, Europe, United States, and Canada between 1990 and 2005. Data from various infant term formulas including Nutrilom (Nutricia, Netherland), Enfamil (Mead Johnson, Canada), Similac (Abbott Ross, US), SMA (Wyeth, US). (JPGN 2010; 51: 380-401)//
**Huang M C, 2007,
$$MCT 9.6
*Final concentration will be measured after experiment is finished The total concentration of TG-DHA and TG-AA in NAN formula is 0.22%, which is below the recommended levels of 1%. Thus, NAN formula was fortified with TG-DHA and TG-AA from fish oil (NuCheck (http://www.nuchekprep.com, ~40% TG-DHA and TG-ARA) to reach a final concentration of 1% TG-DHA and 2% TG-DHA respectively.

5.4 Pancreatic Duct Ligation Surgery for Induction of Exocrine Pancreatic Insufficiency (EPI)

EPI surgery was performed on 12+2 young pigs 6-8 weeks of age. EPI is typically fully developed three to four weeks after the surgery. Development of total pancreatic insufficiency was confirmed by arrested growth (minimal or no increase in body weight) and/or development of steathorrhea.

Example 6: Experimental Design, Procedures 6.1 Study Design

The study contained three periods: adaptation, control, and testing. During the 7-day adaptation period, pigs were trained to drink infant formula fortified with TG-DHA and TG-ARA. During the 7-day control period, pigs continued to be fed infant formula fortified with TG-DHA and TG-ARA. During the 7-day testing period, the pigs were fed infant formula fortified with TG-DHA and TG-ARA, either (a) non-hydrolyzed; (b) pre-hydrolyzed with CV lipase; or (c) pre-hydrolyzed with RO lipase. Formula consumption was measured daily, faeces samples were collected the last 3 days of each study period (72 hr collection), and blood samples were collected on day 7 of the control and testing periods.

6.2 Lipase Dosing

Dose of lipase and pre-hydrolysis time were determined based on in vitro results (Example 3) and daily nutritional requirements of pigs. NAN formula mixed with lipase RO or CV (~1300 U/g total fat) was incubated with shaking for 15 minutes at 37 C.

Proposed formula preparation and lipase mix:
Body weight of pigs ranged from 11-14 kg
Feed requirement: 40 g formula powder/kg body weight;
Daily need 500 g powder/pig
4 meals per day
125 g powder/pig/meal
Meal preparation: 500 g powder+1.5 L water (dilution 1:4)
Add dry powder first
Add TG-PUFA oils (7.5 mL DHA and 15 mL ARA), mix well, and add tap water from water bath at 37 C, mix well
For lipase-treated formula, mix in CV or RO lipase
Add water to final volume
Mix all 15 min in water bath at 37 C
Divide into 4 buckets and feed each pig ~600 mL of formula 6.2.1 Adaptation Period (7-10 days)

Approximately 7-10 days before the Adaptation period, 12 pigs were placed in metabolic cages and trained to drink formula enriched with TG-PUFA. On the first morning of the Adaptation period, body weight was recorded before the morning meal.

6.2.2 Control Period (7 days)

To all selected pigs infant formula was given as the only source of food, 4 times per day. The total daily formula consumption was measured during the entire experiment. On the morning of the first day of the Control period, body weight was recorded before the morning meal. 3×24 hr stool samples were collected from day 5 through day 7. Blood samples were collected on the last day of this period, 1 hr before a meal and 1, 2, and 3 hours later.

6.2.3 Testing Period (7 days)

To all selected pigs TG-PUFA enriched infant formula was given as the only source of food, 4 times per day. The total daily milk consumption was measured during the entire experiment. On the morning of the first day of the Testing period body weight was recorded before morning meal. 3×24 h stool samples were collected from day 5 through day 7. Blood samples were collected on the last day of this period, 1 h before a meal and 1, 2, and 3 h later.

Before the start of this period, pigs were randomized into three groups, based on body weight and willingness to drink formula:

1) One-third of the EPI pigs (n=4) were fed formula pre-hydrolyzed with RO lipase;
2) One-third of the EPI pigs (n=4) were fed formula pre-hydrolyzed with CV lipase; and
3) One-third of the EPI pigs (n=4) were fed formula only.

Preparation of the formula and lipase mix is shown above.

6.3 Criteria for a Positive Response

Significant reduction in fecal LCPUFA, increase in coefficient of fat absorption (% CFA), and increase in concentration of plasma LCPUFA when compared to EPI pigs fed only formula supplemented with 2% TG-ARA and 1% TG-AA.

6.4 Data Analysis

Individual data were recorded at the time they are generated. Statistical analyses were performed using the Student t-test. Differences were considered significant if $p<0.05$.

Example 7: RO and CV Lipases Improve Fatty Acid Absorption in EPI Pigs

Pigs with exocrine pancreatic insufficiency (EPI), a well established surgical model, were used as a model to mimic pre-term or full-term human babies, where exocrine pancreatic function is compromised. The EPI surgical pig model was used essentially as described in Examples 5 and 6 to evaluate the effect on fatty acid absorption of infant formula pre-hydrolyzed with CV lipase or RO lipase as compared to non-hydrolyzed infant formula. EPI pigs were 10 weeks of age (+/−2 weeks), which corresponds to about 6 months of age for a human infant. Pigs were feed Nestle (NAN Pro 1 Gold) infant formula enriched with 2% ARA triglycerides (TG-ARA) and 1% DHA triglycerides (TG-DHA) from fish oil (NuCheck (http://www.nu-chekprep.com, ~40% TG-DHA and TG-ARA). Feeding occurred every 3 hours, 4 times per day. In the group of pigs receiving pre-hydrolyzed formula, the formula was pre-hydrolyzed 15 minutes before feeding by mixing with CV lipase or RO lipase at 37° C. The duration of the experiment was 1 week, followed by analysis of LC-PUFA concentration in faeces, absorption of LC-PUFA in plasma, and accretion of LC-PUFA in tissues (retina, heart, liver, kidney, erythrocytes, brain, and fat).

Figures 22A, 22B, 22C:
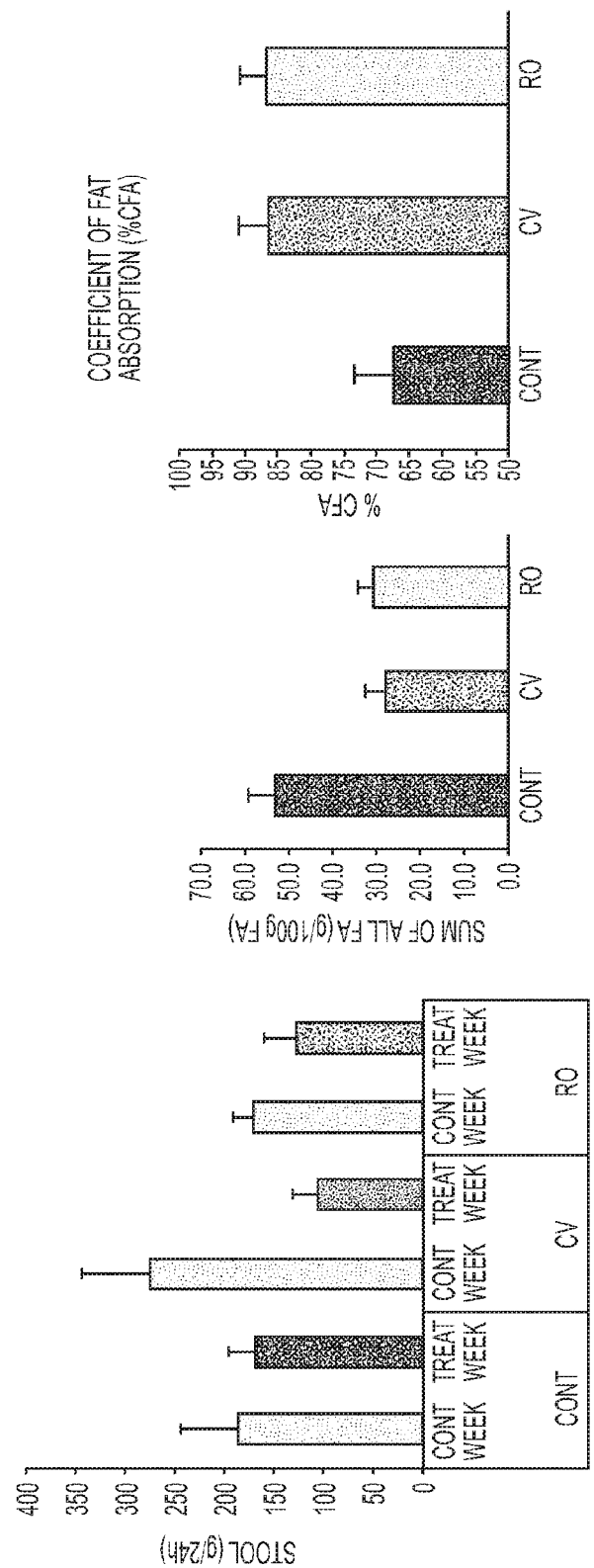
FIG. 22A shows stool weight in EPI pigs during the control week ("Cont week," during which pigs were fed TG-LCPUFA fortified infant formula) vs. the treatment week ("Treat week," during which pigs were fed the same fortified formula either non-hydrolyzed ("CONT"), pre-hydrolyzed with Chromobacterium *viscosum* lipase ("CV"), or pre-hydrolyzed with *Rhizopus oryzae* lipase ("RO")).
FIG. 22B shows total fecal fat content over the last 3 days of the treatment week in the same 3 groups of pigs.
FIG. 22C shows the coefficient of fat absorption (% CFA).
Figure 23A:
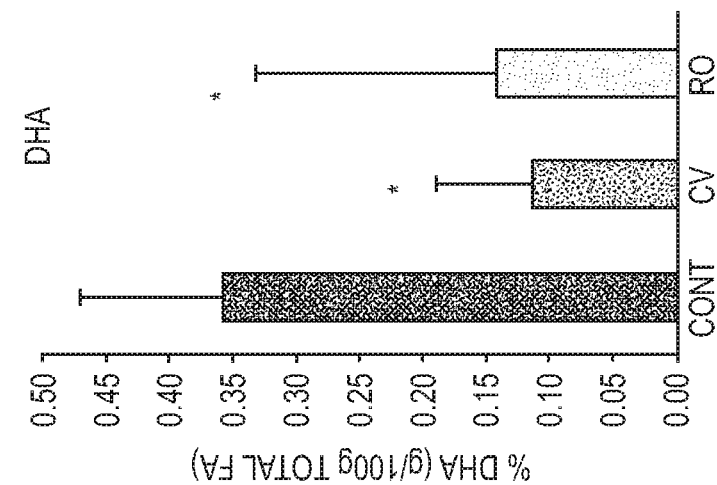
FIGS. 23A-C show the levels of ARA (FIG. 23A), EPA (FIG. 23B), and DHA (FIG. 23C) in the faeces of EPI pigs fed non-hydrolyzed formula ("CONT"), formula pre-hydrolyzed with CV lipase ("CV"), or formula pre-hydrolyzed with RO lipase ("RO"). Asterisks indicate $p<0.001$.
Figure 23B:
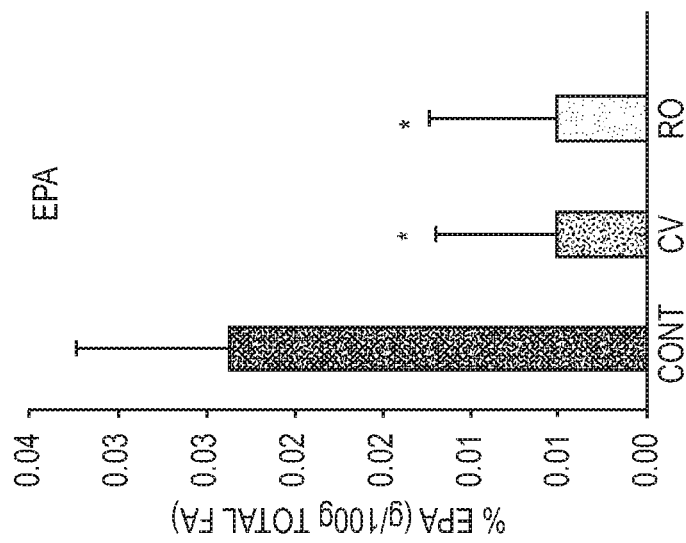
Figure 23C:
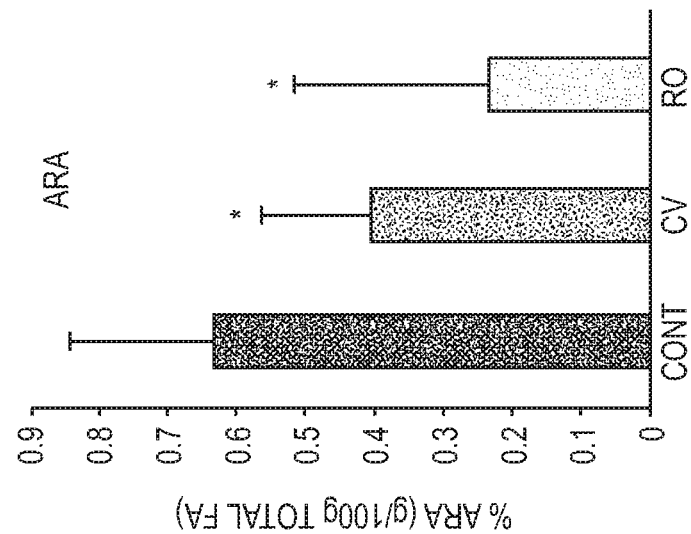

As shown in FIG. 22A, EPI pigs given formula pre-hydrolyzed with CV lipase or RO lipase had significantly reduced stool weight (CV: >60% reduction, $p<0.001$; RO: ~30% reduction, $p<0.05$). Pre-hydrolysis of fat with CV lipase or RO lipase also significantly reduced total fat content in the faeces compared to control EPI pigs (FIG. 22B) and significantly increased the coefficient of fat absorption (% CFA) compared to controls (FIG. 22C), where % CFA=(fat intake (g/24 hr) −fat in faeces (g/24 hr))/(fat intake (g/24 hr)), n=3/arm, $p=0.002$ for CV vs. control, and $p=0.003$ for RO vs. control. As compared to control, pre-hydrolysis with either CV lipase or RO lipase caused significant reductions in faecal ARA, (36% and 65% reductions, respectively), EPA (78% reduction with either enzyme), and DHA (68% and 60% reductions, respectively) (FIG. 23). These data show that pre-hydrolysis of formula with CV or RO lipase reduces faecal levels of total fat, ARA, DHA, and EPA, indicating an improvement in the absorption of omega-3, omega-6, and total fatty acids.

Figure 24B:
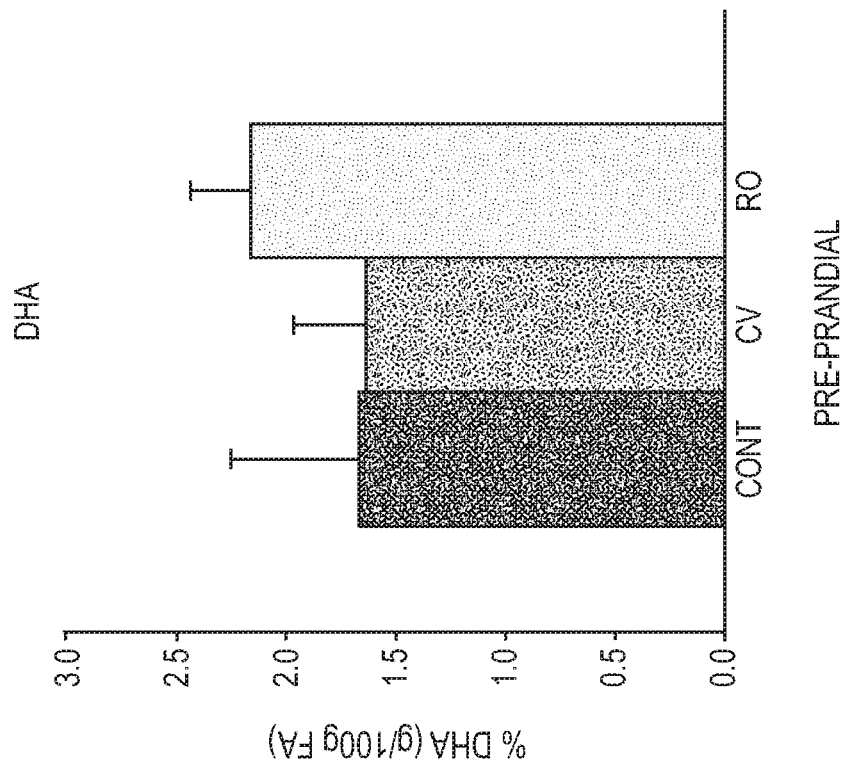
FIGS. 24A and 24B show levels of ARA (FIG. 24A) and DHA (FIG. 24B) in the plasma of EPI pigs following 7 days of feeding with non-hydrolyzed formula ("CONT"), formula pre-hydrolyzed with CV lipase ("CV"), or formula pre-hydrolyzed with RO lipase ("RO"). Asterisks indicate $p<0.05$.
Figure 24A:
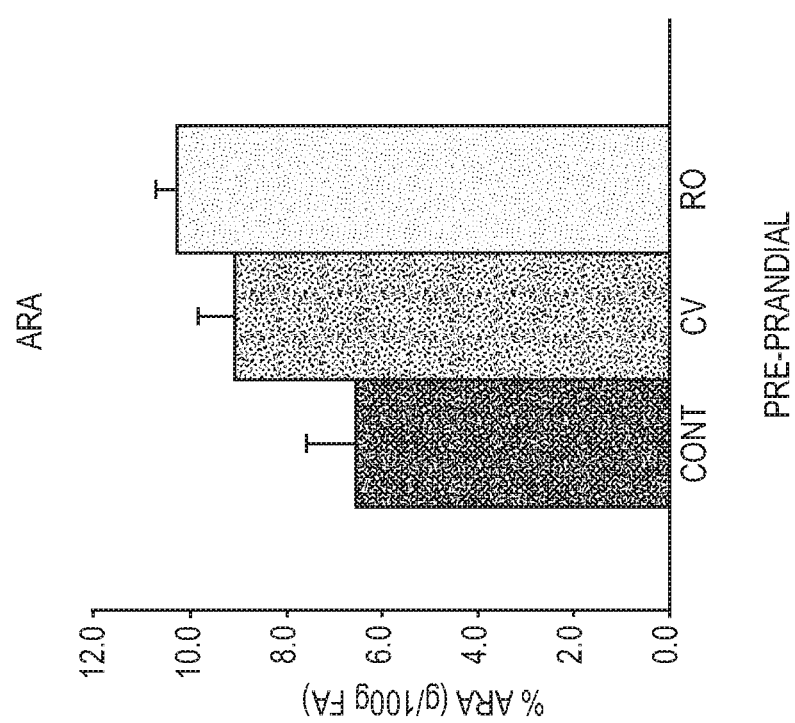
Figure 25B:
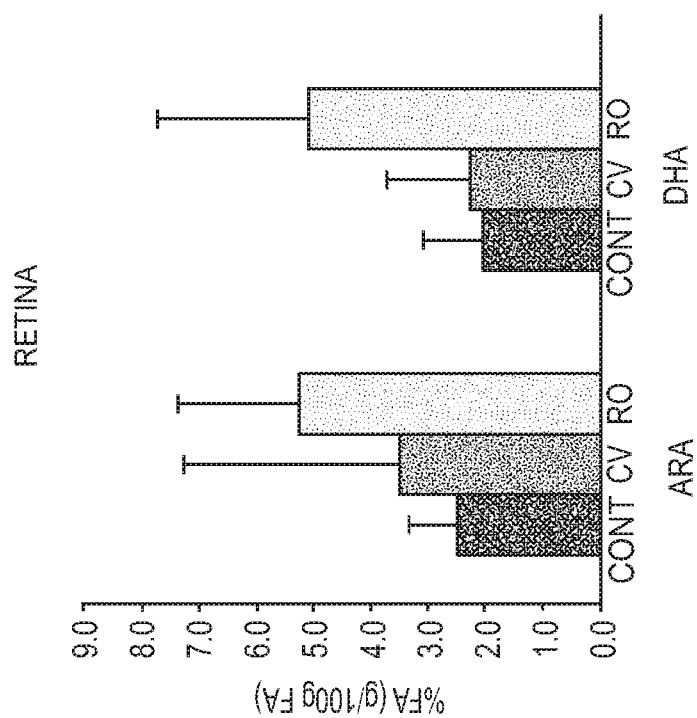
FIGS. 25A and 25B show levels of ARA and DHA in the retina (FIG. 25A) and adipose tissue (FIG. 25B) of EPI pigs following 7 days of feeding with non-hydrolyzed formula ("CONT"), formula pre-hydrolyzed with CV lipase ("CV"), or formula pre-hydrolyzed with RO lipase ("RO"). Asterisks indicate $p<0.05$.
Figure 25A:
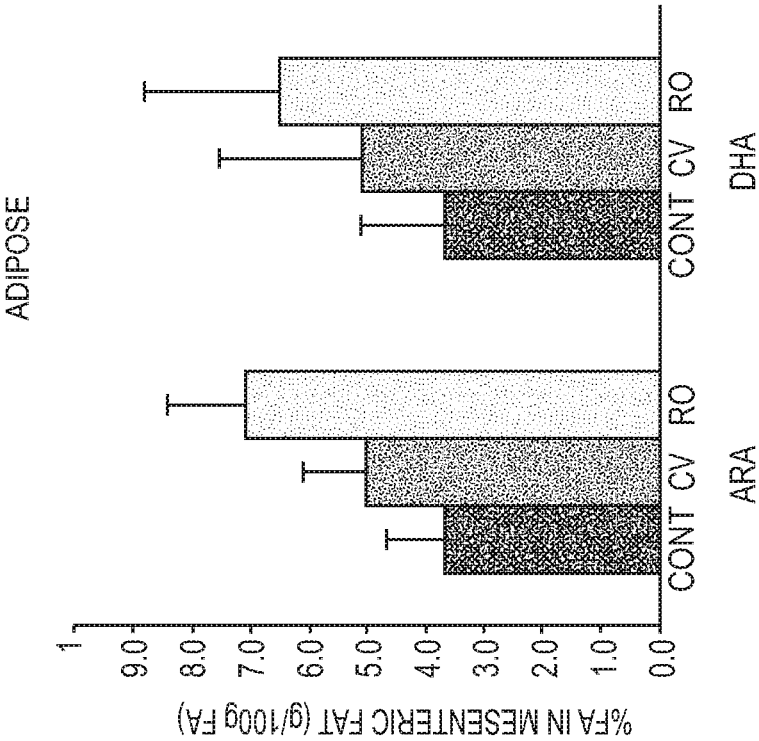
Figure 26B:
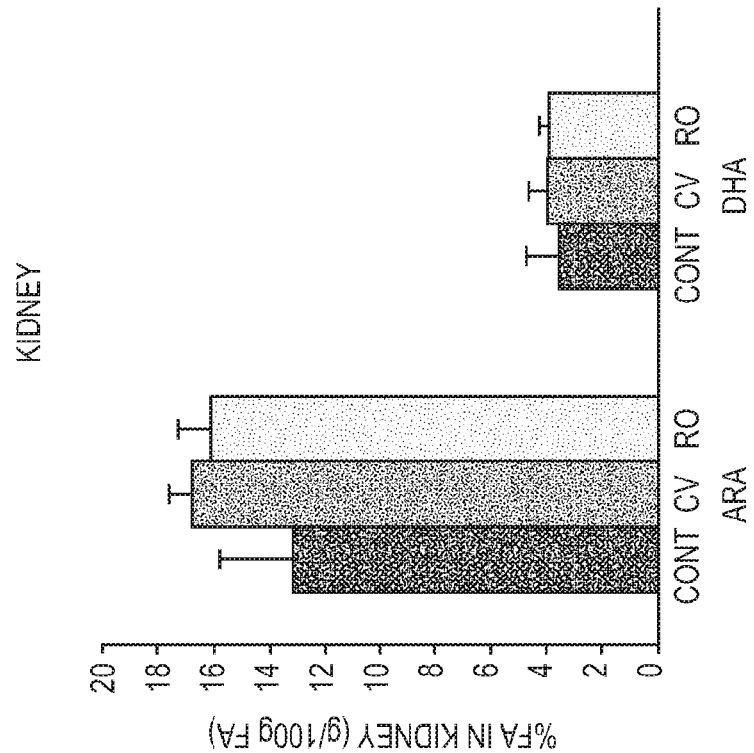
FIGS. 26A and 26B show levels of ARA and DHA in the heart (FIG. 26A) and kidney tissue (FIG. 26B) of EPI pigs following 7 days of feeding with non-hydrolyzed formula ("CONT"), formula pre-hydrolyzed with CV lipase ("CV"), or formula pre-hydrolyzed with RO lipase ("RO"). Asterisks indicate $p<0.05$.
Figure 26A:
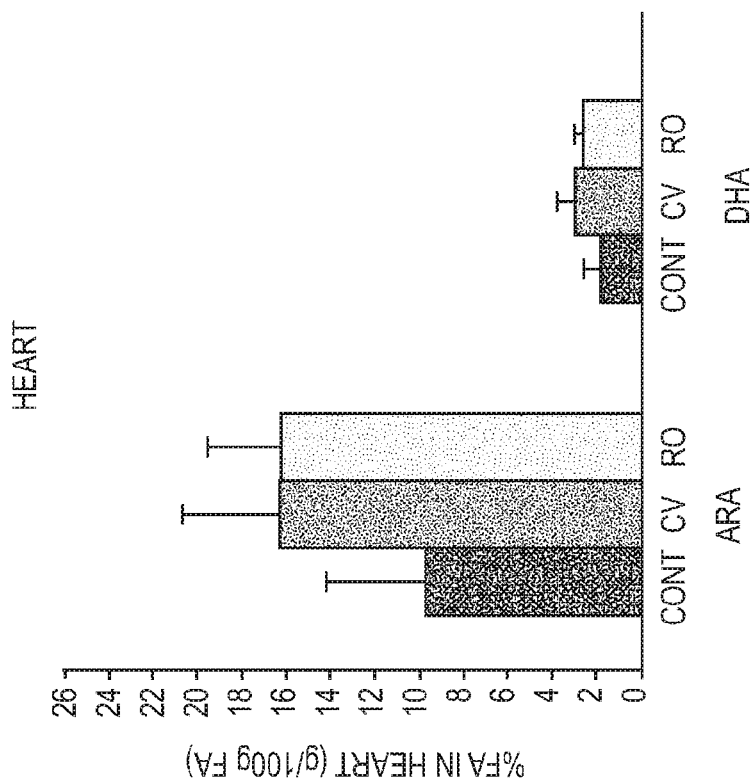
Figure 27A:
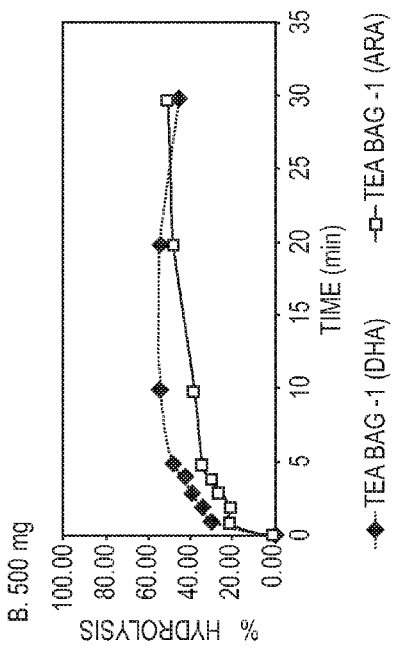
FIGS. 27A-27D show percent hydrolysis of DHA and ARA in Enfalac formula with 100 mg (FIG. 27A), 500 mg (FIG. 27B), 1000 mg (FIG. 27C), or 2000 mg (FIG. 27D) of immobilized RO lipase.
Figure 27B:
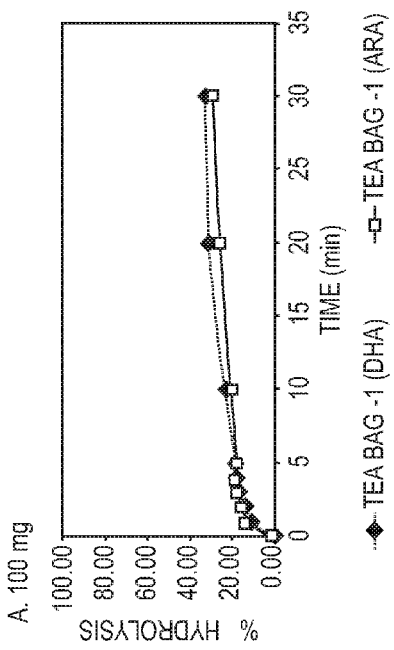
Figure 27C:
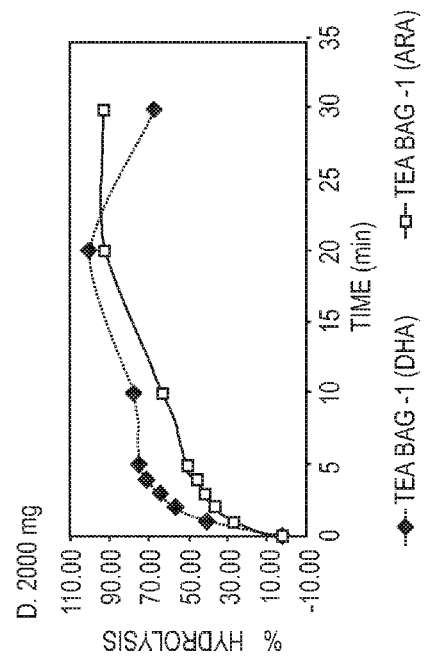
Figure 27D:
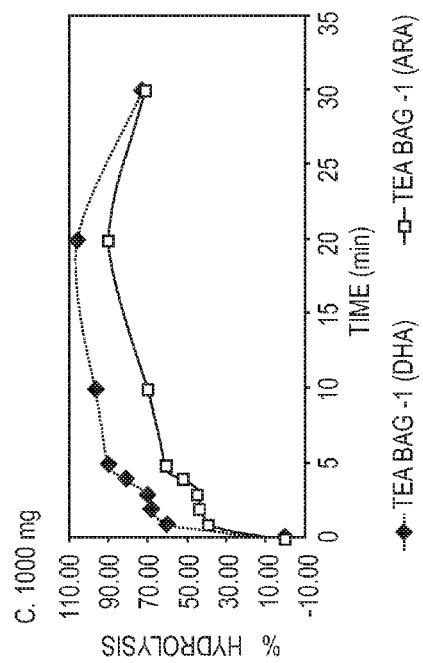

In addition, pigs fed pre-hydrolyzed formula had a significant increases in plasma and tissue levels of ARA and DHA after 7 days of feeding compared to control pigs. For these studies, there were 4 pigs in the Control and CV lipase groups and 3 pigs in the RO lipase group. Pre-prandial plasma samples were taken after overnight fasting following 7 days of treatment. Plasma levels of ARA and DHA were significantly higher (60% and 30%, respectively, $p<0.05$) in pigs fed formula pre-hydrolyzed with RO lipase compared to pigs fed non-hydrolyzed formula (FIG. 24). Plasma levels of ARA were also significantly higher (40%, $p<0.05$) in pigs fed formula pre-hydrolyzed with CV lipase compared to pigs fed non-hydrolyzed formula (FIG. 24). ARA and DHA levels also increased significantly ($p<0.05$) in the retina (FIG. 25A) and adipose tissue (FIG. 25B) of pigs fed formula pre-hydrolyzed with RO lipase compared to pigs fed non-hydrolyzed formula. Retina levels of ARA were also significantly higher ($p<0.05$) in pigs fed formula pre-hydrolyzed with CV lipase compared to pigs fed non-hydrolyzed formula (FIG. 25A). In pigs fed formula pre-hydrolyzed with CV or RO lipase, ARA levels also increased significantly ($p<0.05$) in the heart (FIG. 26A: 60% and 20% increase, respectively) and kidney (FIG. 26B) of pigs compared to pigs fed non-hydrolyzed formula. DHA levels increased significantly (60%, $p<0.05$) in the heart of pigs fed formula pre-hydrolyzed with CV lipase compared to pigs fed non-hydrolyzed formula (FIG. 26A). There were minimal or no changes in liver, erythrocytes, and brain, which may be explained by the relatively short duration of treatment (7 days) in this study.

Example 8: Hydrolysis of TG-DHA and TG-ARA in Infant Formula by Immobilized Lipase in a "Teabag"

*Rhizopus oryzae* (RO) lipase was covalently bound to acrylic beads and contained in a device resembling a teabag. Enfalac infant formula (25 g) was combined with tap water (88 mL) at 37° C. Reactions were carried out in a glass bottle with 100 mL of infant formula and a tea bag containing either 100, 500, 1000, or 2000 mg of immobilized RO lipase. Each reaction was incubated at 37° C. for 30 minutes with inversion. Samples were taken at the following timepoints: 0, 1, 2, 3, 4, 5, 10, 20, and 30 minutes. Samples were analyzed for DHA and ARA by reverse phase high performance liquid chromatography (RP-HPLC).

At each concentration of immobilized RO lipase, the percent hydrolysis of DHA and ARA increased as the amount of immobilized RO lipase increased (FIG. 27). These data demonstrate the feasibility of the tea bag device for pre-hydrolyzing formula with lipase.

Example 9: Hydrolysis of TG-DHA and TG-ARA in Infant Formula by Immobilized Lipase in a Cartridge

*Rhizopus oryzae* (RO) lipase and *Chromobacterium viscosum* (CV) lipase were immobilized onto macroporous acrylic polymer beads (Immobeads™ChiralVision). Approximately 200 mg of RO lipase were used per gram of beads. A sample of CV lipase-coated beads was irradiated (CVI) to determine the effect of irradiation on potency of immobilized lipase. Approximately 1.7 g of each bead preparation (RO, CV, and CVI) were packed into columns with bed volumes of approximately 5 mL. Infant formula containing DHA and ARA triglycerides was passed over the column at a flow rate of 75 mL/hr. The column eluate was analyzed for DHA and ARA hydrolysis by HPLC. The percent hydrolysis of DHA and ARA triglycerides by CV, CVI, and RO lipases is shown in Table 6.

TABLE 6

Hydrolysis of TG-DHA and TG-ARA using immobilized lipase cartridge

| | Column packing | % Hydrolysis TG-DHA | % Hydrolysis TG-ARA |
|---|---|---|---|
| CV | 5 mL | 92.50 | 41.00 |
| CVI | 5 mL | 71.90 | 34.50 |
| RO | 5 mL | 98.79 | 94.85 |

Example 10: RO Lipase Versus Pancreatin

Figures 28A, 28B:
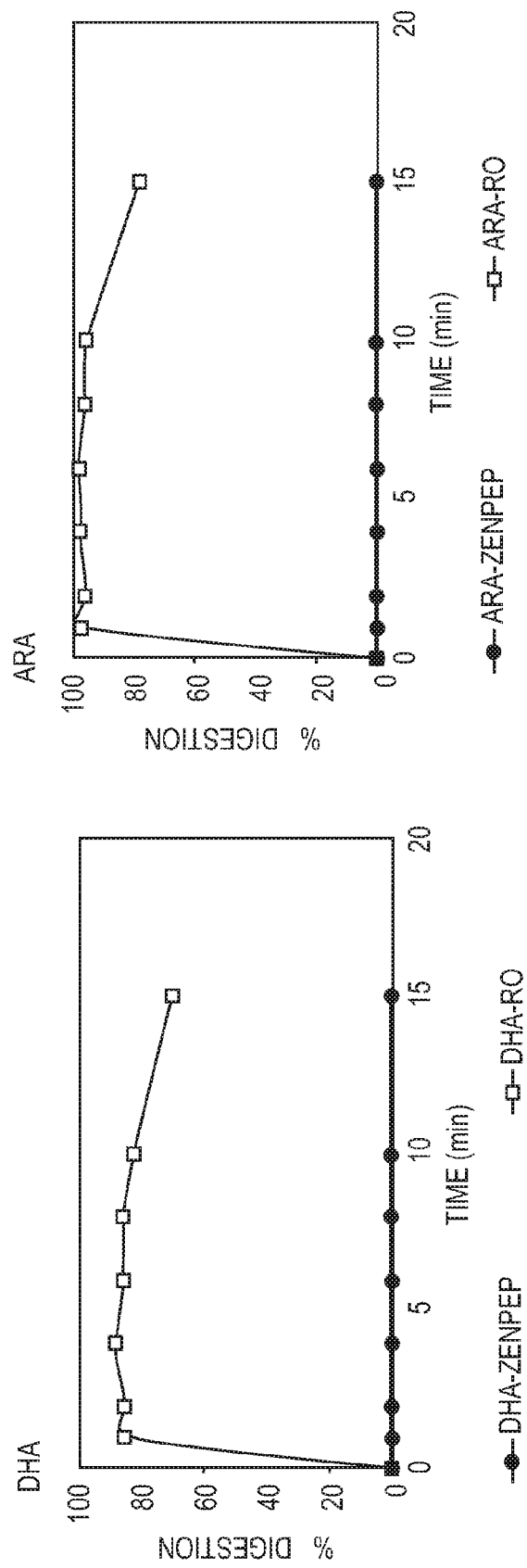
FIGS. 28A and 28B show percent hydrolysis of DHA (FIG. 28A) and ARA (FIG. 28B) with RO lipase or pancreatin.

*Rhizopus oryzae* (RO) lipase displayed far greater activity toward DHA and ARA triglycerides than porcine pancreatin (Zenpep®), which contains a mixture of pancreatic lipases, proteases, and amylases. 1.4 mL of infant formula was mixed with 100 uL of lipase (either pancreatin or RO lipase) and 100 uL each of triglycerides of DHA and ARA. Reactions were incubated at 37° C. for 15 minutes. Samples were taken at time points 0, 1, 2, 4, 6, 8, 10, and 15 minutes and analyzed by RP-HPLC for DHA and ARA. DHA (FIG. 28A) and ARA (FIG. 28B) triglycerides were hydrolyzed by RO lipase over time but were not hydrolyzed by pancreatin.

Figure 29:
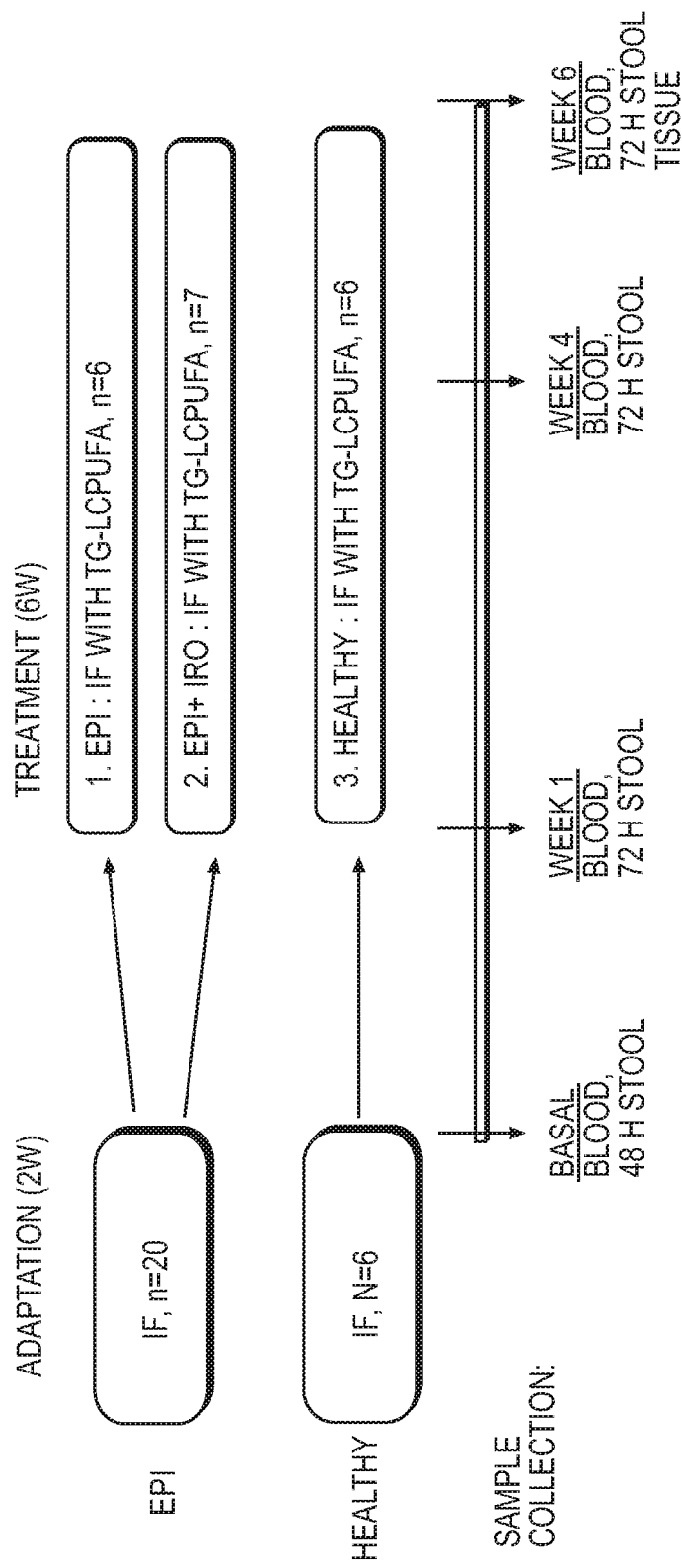
FIG. 29 depicts the study design for the 6-week pig study described in Example 10.

Example 11: 6-Week Pig Study: Long-Term Feeding of Pigs with Formula Pre-Hydrolyzed by Immobilized Lipase Six healthy pigs and twenty pigs with surgically-induced exocrine pancreatic insufficiency (EPI) (see Example 5) were subjected to a two-week adaptation/control period followed by a six-week testing period (FIG. 29). During the adaptation period, all pigs were fed NAN Pro 1 Gold infant formula (Nestle) ("IF"). During the testing period, the healthy pigs ("Healthy") and six of the pigs with EPI ("EPI") were fed infant formula fortified with TG-LCPUFA (see Examples 5 and 6); seven of the pigs with EPI were fed TG-LCPUFA-fortified infant formula that had been pre-hydrolyzed with immobilized RO enzyme using a "teabag" device ("EPI+iRO"). The remaining pigs were withdrawn from the study for various reasons, e.g., failure to surgically induce complete EPI.

For pre-hydrolysis, 2 liters of NAN Pro 1 Gold (Nestle) infant formula were prepared by mixing 1.5 liters of water at 37 C with 500 g of powdered formula fortified with 50 mg/kg TG-DHA and 100 mg/kg TG-ARA (see Example 5, Section 5.3). Five teabag-like devices containing RO lipase immobilized on beads (1 gram of immobilized lipase in each "teabag") were added to the 2 liters of formula and mixed at room temperature for 15 minutes using a magnetic stirrer at constant mixing speed. This corresponds to 9,000 units (as measured against olive oil) of immobilized RO lipase per 150 grams of total fat in the fortified formula (60 U/g total fat). Before hydrolysis, the fortified formula contained 17.4 mmol/liter of non-esterified fatty acids. After hydrolysis, the formula contained 107.6 mmol/liter of non-esterified fatty acids.

Food consumption was measured daily. Blood and stool samples were collected at the end of the adaptation period ("basal"), and after weeks 1, 4, and 6 of the treatment period. For the basal sample, faeces were collected for 48 hours (2×24 h). For the week 1, 4, and 6 samples, faeces were collected for 72 hours (3×24 h). At the completion of the treatment period, organs and tissues were collected for absorption and safety studies.

Pre-hydrolyzed formula was well tolerated with no treatment-related changes in food intake, growth, organs (by gross examination), or general well being. There was no fatty liver development based on gross liver examination when the pigs were sacrificed at the end of the 6-week study.

Figures 30A, 30B:
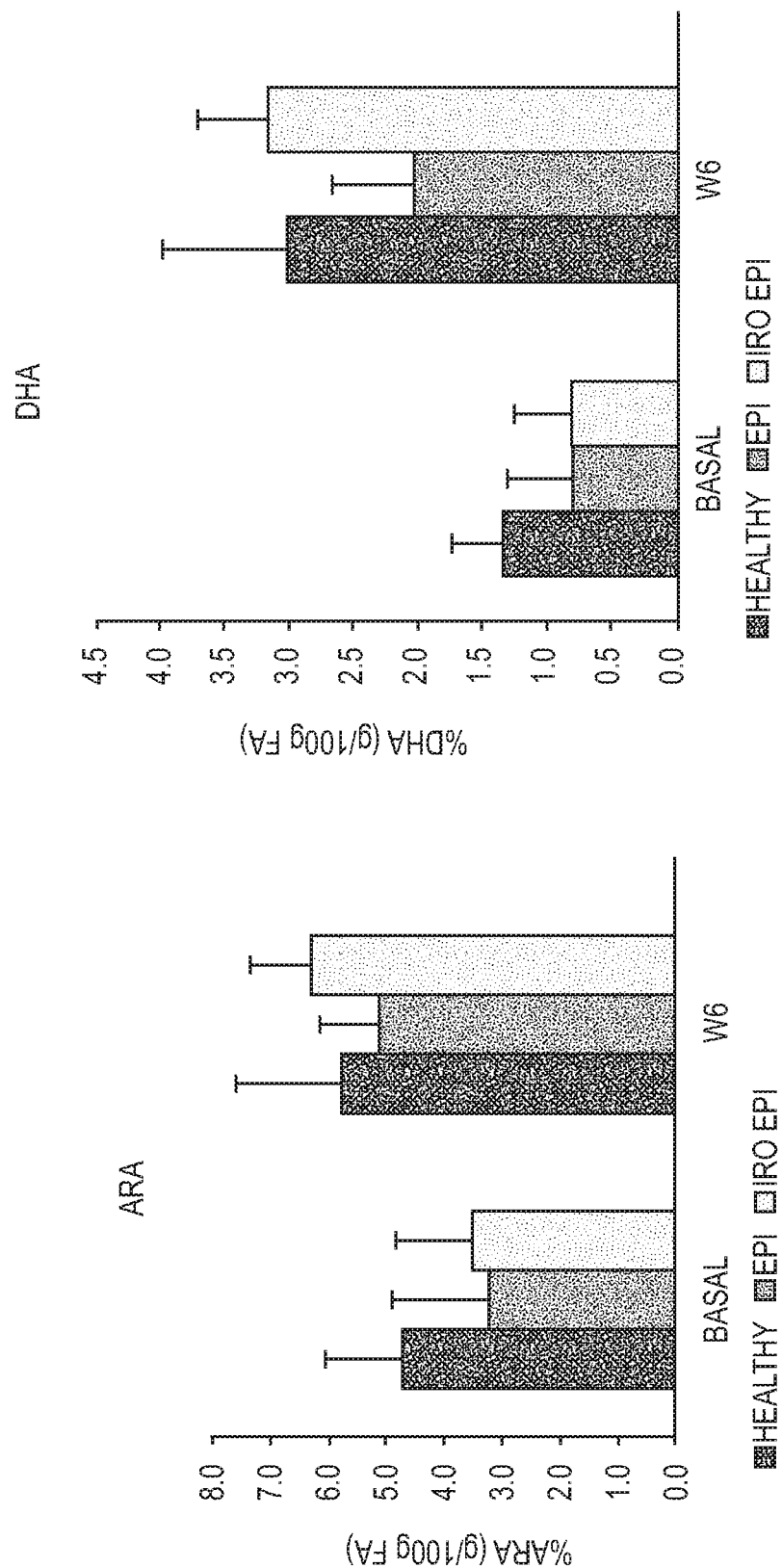
FIGS. 30A and 30B show levels of ARA (FIG. 30A) and DHA (FIG. 30B) in erythrocytes collected from healthy pigs fed TG-LCPUFA-fortified infant formula ("Healthy"), pigs with surgically-induced exocrine pancreatic insufficiency fed TG-LCPUFA-fortified infant formula ("EPI"), and pigs with surgically-induced exocrine pancreatic insufficiency fed TG-LCPUFA-fortified infant formula that had been pre-hydrolyzed by immobilized RO lipase ("EPI+iRO").

After six weeks, there was a statistically-significant increase in ARA (FIG. 30A) and DHA levels (FIG. 30B) in erythrocytes (20% and 36%, respectively) in EPI pigs fed pre-hydrolyzed formula (EPI+iRO), as compared to EPI pigs fed the TG-LCPUFA-fortified formula without prehydrolysis (EPI). Erythrocyte levels of ARA and DHA did not differ significantly between healthy pigs and EPI pigs fed pre-hydrolyzed formula for six weeks.

As shown in Table 7, there was a statistically-significant increase in plasma levels of triglycerides, cholesterol, HDL, and LDL in EPI pigs fed pre-hydrolyzed formula for six weeks. Plasma levels of triglycerides, cholesterol, HDL, and LDL did not differ significantly between healthy pigs and EPI pigs fed pre-hydrolyzed formula for six weeks.

TABLE 7

| Group | Triglycerides | Cholesterol | HDL | LDL |
| --- | --- | --- | --- | --- |
| Healthy | 4.13 ± 0.68 | 0.51 ± 0.25 | 2.04 ± 0.31 | 1.27 ± 0.33 |
| EPI | 2.69 ± 0.56 | 0.22 ± 0.07 | 1.46 ± 0.41 | 0.69 ± 0.35 |
| EPI + iRO | 4.09 ± 1.47* | 0.44 ± 0.19* | 1.93 ± 0.46* | 1.13 ± 0.54* |

(All values in mmol/L. Asterisks indicate $p < 0.05$ for the difference between EPI and EPI + iRO.)

As shown in Table 8, pigs fed pre-hydrolyzed formula for six weeks had increased plasma levels of vitamins A and E, but no significant difference for vitamin D. There was a statistically significant difference ($p<0.05$) in the plasma level of vitamin E between the EPI and EPI+iRO groups. For vitamin A, there was a statistically significant difference ($p<0.05$) between the EPI and healthy groups but not between the EPI+iRO and healthy groups.

TABLE 8

| Group | Alpha-tocopherol mg/mL Vitamin E | Retinol mg/mL Vitamin A | 25-OH-D3 ng/mL Vitamin D |
| --- | --- | --- | --- |
| Healthy | 6.6 ± 1.4 | 0.34 ± 0.06 | 9.4 ± 2.0 |
| EPI | 0.8 ± 0.4 | 0.18 ± 0.06 | 10.4 ± 3.6 |
| EPI + IRO | 1.5 ± 0.9* | 0.26 ± 0.17 | 10.2 ± 4.1 |

We claim:

1. An enteral feeding device for providing a nutritional formula comprising monoglycerides and free fatty acids by exposing a nutritional composition comprising long-chain polyunsaturated fatty acid (LC-PUFA) triglycerides and/or LC-PUFA esters to lipase prior to ingestion, the device comprising:
a container defining an interior for receiving the nutritional composition;
at least one opening fluidly connected to the container, wherein the at least one opening is dimensioned for connection to a feeding tube;
a structure in fluid communication with the interior of the container; and
a lipase immobilized by covalent binding to the structure so that the nutritional composition is exposed to the lipase when the nutritional composition is received within the container;
wherein the covalent binding limits the amount of lipase that leaches into the nutritional composition when the nutritional composition is exposed to the lipase.

2. The device of claim 1, comprising two openings fluidly connected to the container, wherein each of the openings is dimensioned for connection to the feeding tube.

3. The device of claim 1, further comprising a feeding tube attached to the at least one opening.

4. The device of claim 1, wherein the structure comprises particles contained within the container.

5. The device of claim 4, wherein the particles comprise balls or beads.

6. The device of claim 4, wherein the particles are magnetic.

7. The device of claim 1, further comprising a valve.

8. The device of claim 1, wherein the lipase is selected from the group consisting of *Chromobacterium viscosum* lipase, *Pseudomonas fluorescens* lipase, and *Rhizopus oryzae* lipase.

9. The device of claim 1, wherein the container is configured so that when the nutritional formula exits the container, the lipase remains in the container.

10. The device of claim 1, further comprising a screen or filter to prevent the lipase from exiting the device with the nutritional formula.

11. An enteral feeding device for providing a nutritional formula comprising monoglycerides and free fatty acids by exposing a nutritional composition comprising long-chain polyunsaturated fatty acid (LC-PUFA) triglycerides and/or LC-PUFA esters to lipase prior to ingestion, the device comprising:
a container defining a fluid inlet, a fluid outlet, and an interior for receiving the nutritional composition in fluid communication with the fluid inlet and the fluid outlet;
a plurality of particles disposed within the interior, wherein lipase is covalently bound to the plurality of particles so that, when the nutritional composition passes through the container of the enteral feeding device, the nutritional composition is exposed to the lipase to produce the nutritional formula and no more than 0.1 milligram of lipase per milligram of LC-PUFA exposed to the lipase leaches into the nutritional formula.

12. The device of claim 11, wherein the fluid outlet is configured to connect to a feeding tube.

13. The device of claim 12, further comprising a feeding tube connected to the fluid outlet.

14. The device of claim 12, wherein the fluid inlet is configured to connect to a feeding tube.

15. The device of claim 11, wherein the plurality of particles comprise balls or beads.

16. The device of claim 11, wherein the plurality of particles are magnetic.

17. The device of claim 11, further comprising a valve.

18. The device of claim 11, wherein the lipase is selected from the group consisting of *Chromobacterium viscosum* lipase, *Pseudomonas fluorescens* lipase, and *Rhizopus oryzae* lipase.

19. The device of claim 11, wherein the container is configured so that when the nutritional formula exits the container, the lipase remains in the container.

20. The device of claim 11, further comprising a screen or filter arranged relative to the fluid outlet.

21. An enteral feeding device comprising:
a container defining a fluid inlet, a fluid outlet, and an interior for receiving a nutritional composition in fluid communication with the fluid inlet and the fluid outlet;
a plurality of particles disposed within the interior, wherein lipase is covalently bound to the plurality of particles so that, when the nutritional composition passes through the container, long-chain polyunsaturated fatty acid (LC-PUFA) triglycerides and/or LC-PUFA esters within the nutritional composition are exposed to the lipase to produce a nutritional formula, and no more than 0.1 milligram of lipase per milligram of LC-PUFA exposed to the lipase exits the enteral feeding device with the nutritional formula.

22. The device of claim 21, wherein the lipase is configured to hydrolyze the LC-PUFA within the nutritional composition to produce monoglycerides and free fatty acids in the nutritional formula.

23. The device of claim 21, wherein at least one of the fluid inlet and the fluid outlet is configured to connect to a feeding tube.

24. The device of claim 21, further comprising a feeding tube connected to at least one of the fluid inlet and the fluid outlet.

\* \* \* \* \*